(12) United States Patent
Zadina et al.

(10) Patent No.: US 10,919,939 B2
(45) Date of Patent: *Feb. 16, 2021

(54) MU OPIOID RECEPTOR AGONIST ANALOGS OF THE ENDOMORPHINS

(71) Applicants: The Administrators of the Tulane Educational Fund, New Orleans, LA (US); United States Department of Veterans Affairs, Washington, DC (US)

(72) Inventors: James E. Zadina, Metairie, LA (US); Laszlo Hackler, Metairie, LA (US)

(73) Assignees: The Administrators of the Tulane Educational Fund, New Orleans, LA (US); United States Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/477,907

(22) Filed: Apr. 3, 2017

(65) Prior Publication Data
US 2017/0362276 A1 Dec. 21, 2017

Related U.S. Application Data

(63) Continuation of application No. 14/974,249, filed on Dec. 18, 2015, now abandoned, which is a continuation-in-part of application No. 14/268,057, filed on May 2, 2014, now abandoned, which is a continuation of application No. 13/477,423, filed on May 22, 2012, now Pat. No. 8,716,436, which is a continuation-in-part of application No. PCT/US2011/043306, filed on Jul. 8, 2011.

(60) Provisional application No. 61/363,039, filed on Jul. 9, 2010.

(51) Int. Cl.
| | |
|---|---|
| *C07K 7/64* | (2006.01) |
| *G01N 33/94* | (2006.01) |
| *C07K 7/56* | (2006.01) |
| *C07K 14/665* | (2006.01) |
| *A61K 38/00* | (2006.01) |
| *C07K 7/06* | (2006.01) |

(52) U.S. Cl.
CPC ............ *C07K 7/64* (2013.01); *C07K 7/06* (2013.01); *C07K 7/56* (2013.01); *C07K 14/665* (2013.01); *G01N 33/9486* (2013.01); *A61K 38/00* (2013.01); *G01N 2333/70571* (2013.01); *G01N 2333/726* (2013.01); *G01N 2500/04* (2013.01)

(58) Field of Classification Search
CPC ........ A61K 38/00; C07K 14/665; C07K 7/06; C07K 7/56; C07K 7/64; G01N 2333/70571; G01N 2333/726; G01N 2500/04; G01N 33/9486
See application file for complete search history.

(56) References Cited

U.S. PATENT DOCUMENTS

| | | |
|---|---|---|
| 5,872,097 A | 2/1999 | Fhölenhag et al. |
| 5,885,958 A | 3/1999 | Zadina et al. |
| 6,303,578 B1 | 10/2001 | Zadina et al. |
| 6,337,319 B1 | 1/2002 | Wang |
| 7,399,762 B2 | 7/2008 | Carroll et al. |
| 2006/0105947 A1 | 5/2006 | Carr et al. |
| 2010/0190718 A1 | 7/2010 | Schiller et al. |

FOREIGN PATENT DOCUMENTS

| | | |
|---|---|---|
| WO | 199842732 A1 | 10/1998 |
| WO | 200205748 A2 | 1/2002 |
| WO | 2010006267 A2 | 1/2010 |
| WO | 2012006497 A2 | 1/2012 |

OTHER PUBLICATIONS

Choh Hao Li, 3-Endorphin: Synthesis of analogs modified at the carboxyl terminus with increased activities, Proc. Nati. Acad. Sci. USA vol. 76, No. 7, pp. 3276-3278, Jul. 1979.*
Luis A. Natividad, From Synapse to Function: A Perspective on the Role of Neuroproteomics in Elucidating Mechanisms of Drug Addiction, Proteomes 2018, 6, 50 , pp. 1-18.*
NIH, National institute on Drug Abuse, Jan. 2019, DrugFacts: Treatment Approaches for Drug Addiction | National Institute on Drug Abuse (NIDA).*
Chang, K.J. et al., Potent Morphiceptin Analogs: Structure Activity Relationships and Morphine-Like Activities, The Journal of Pharmacology and Experimental Therapeutics 227 (2), 403-408 (1983).
Handa, B.K et al., Analogues of β-LPH61-64 Possessing Selective Agonist Activity At μ-Opiate Receptors, European Journal of Pharmacology 70, 531-540 (1981).
Honda, T. et al., Differential Receptor Binding Characteristics of Consecutive Phenylalanines in μ-Opioid Specific Peptide Ligand Endomorphin-2, Biorganic & Medicinal Chemistry 15, 3883-3888 (2007).
Hruby, V.J. et al., Cyclic Enkephalin Analogues with Exceptional Potency and Selectivity for σ-Opioid Receptors, J. Med. Chem. 40, 3957-3962 (1997).
Loew, G. et al., Structure-Activity Studies of Morphiceptin Analogs: Receptor Binding and Molecular Determinants of μ-Affinity and Selectivity, Molecular Pharmacology 29, 546-553 (1986).
Misicka, A. et al., Structure-Activity Relationship of Biphalin. The Synthesis and Biological Activities of News Analogues With Modifications in Positions 3 and 4, Life Sciences 60 (15), 1263-1269 (1997).

(Continued)

*Primary Examiner* — James H Alstrum-Acevedo
*Assistant Examiner* — Erinne R Dabkowski
(74) *Attorney, Agent, or Firm* — Olson & Cepuritis, Ltd.

(57) ABSTRACT

The invention relates to cyclic peptide agonists that bind to the mu (morphine) opioid receptor and their use in the treatment of acute and/or chronic pain. Embodiments of the invention are directed to cyclic analogs of endomorphin. These peptide analogs exhibit decreased tolerance relative to morphine, increased solubility compared to similar tetrapeptide analogs, while maintaining favorable or improved therapeutic ratios of analgesia to side effects.

22 Claims, 23 Drawing Sheets

Specification includes a Sequence Listing.

(56) References Cited

OTHER PUBLICATIONS

Schiller, P.W. et al., Synthesis and Activity Profiles of Novel Cyclic Opioid Peptide Monomers and Dimers, Journal of Medicinal Chemistry 28 (12), 1766-1771 (1985).

Schiller, P.W. et al., Comparison of µ-, σ- And -k-Receptor Binding Sites Through Pharmacologic Evaluation of p-Nitrophenylalanine Analogs of Opioid Peptides, Life Sciences 33, Sup.1, 319-322 (1983).

Schiller, P.W. et al., A Novel Side-Chain-Linked Antiparallel Cyclic Dimer of Enkephalin, FEBS 3039, 191 (2), 231-234 (1985).

Bryant, S.D. et al., DMT and Opioid Peptides: A Potent Alliance, Biopolymers (Peptide Science) 71, 86-102 (2003).

Capasso, A. et al., Bioactivity of New µ and σ Opioid Peptides, Medicinal Chemistry 3, 480-487 (2007).

Czapla, M.A. et al., "Reduced Suppression of CO2-Induced Ventilatory Stimulation by Endomorphins Relative to Morphine", Brain Res., 1059 (2), 159-166 (2005).

Czapla, M., et al., Differential Cardiorespiratory Effects of Endomorphin 1, Endomorphin 2, DAMGO, and Morphine, American Journal of Respiratory and Critical Care Medicine, vol. 162, 994-999 (2000).

Fichna, J. et al., Effect of 2',6'-dimethyl-L-tyrosine (Dmt) on Pharmacological Activity of Cyclic Endomorphin-2 and Morphiceptin Analogs, Bioorganic & Medicinal Chemistry 19, 6977-6981 (2011).

Fiori, S. et al., Preferred Conformation of Endomorphin-1 in Aqueous and Membrane-Mimetic Environments, J. Mol. Biol. 291, 163-175 (1999).

Janecka, A., et al., Synthesis and Antinociceptive Activity of Cyclic Endomorphin-2 and Morphiceptin Analogs, Biochemical Pharmacology 71 (2005), 188-195.

Lenard, N. R. et al., Absence of Conditioned Place Preference or Reinstatement with Bivalent Ligands Containing Mu-Opioid Receptor Agonist and Delta-Opioid Receptor Antagonist Pharmacophores, Eur. J. Pharmacol, 566 (1-3), 75-82 (2007).

Li, T. et al., Bifunctional [2',6'-Dimethyl-L-Tyrosine] Endomorphin-2 analogues Substituted at Position 3 with Alkylated Phenylalanine Derivatives yield Potent Mixed µ-Agonist/σ-Antagonist and Dual µ-Agonist/σ-Agonist Opioid Ligands, Journal of Medicinal Chemistry, vol. 50 (12), 2753-2766 (2007).

Pakkala, M. et al., Activity and Stability of Human Kallikrein-2-Specific Linear and Cyclic Peptide Inhibitors, J. Pept. Sci.13 (2007), 348-353.

Perlikowska, R. et al., Synthesis and Biological Evaluation of Cyclic Endomorphin-2 Analogs, Peptides 31 (2010); 339-345.

Purington, L.C. et al., Pentapeptides Displaying Mu Opioid Receptor Agonist and Delta Opioid Receptor Partial Agonist/Antagonist Properties, J. Med. Chem., 52 (23), 7724-7731 (2009).

Wilson, A.M. et al., Dissociation of Analgesic and Rewarding Effects of Endomorphin-1 in Rats, Peptides, 21 (12), 1871-1874 (2000).

Yamamoto, T. et al., Discovery of a Potent and Efficacious Peptide Derivative for σ/µ Opioid Agonist/Neurokinin 1 Antagonist Activity with a 2',6'-Dimethyl-L-Tyrosine: In vitro, In vivo, and NMR-Based Structural Studies, Journal of Medicinal Chemistry, vol. 54, 2029-2038 (2011).

Zadina, J.E. et al., "A Potent and Selective Endogenous Agonist for the mu-Opiate Receptor", Nature 386 (6624), 499-502 (1997).

* cited by examiner

Tyr-c[D-Lys-Trp-Phe-Glu]-NH₂
(SEQ ID NO:1)

C₄₀H₄₈N₈O₇

MW=752.3646

Tyr-c[D-Glu-Phe-Phe-Lys]-NH₂
(SEQ ID NO:2)

$C_{38}H_{47}N_7O_7$

MW=713.3535

Tyr-c[D-Glu-Phe-Phe-Lys]-Gly-NH₂
(SEQ ID NO:4)

C₄₀H₅₀N₈O₈

MW=770.3752

(A)

(B)

| Receptor Binding | Ki (nM) | | | Selectivity | |
|---|---|---|---|---|---|
| | mu | delta | kappa | delta/mu | kappa/mu |
| Morphine | 0.92 | 242 | 56 | 263 | 61 |
| DAMGO | 0.73 | 589 | 334 | 812 | 461 |
| EM1 | 2.07 | 1215 | >10k | 587 | >5000 |
| EM2 | 1.32 | 5704 | >10k | 4321 | >5000 |
| Analog 1 | 0.63 | 83 | 283 | 132 | 453 |
| Analog 2 | 0.96 | 82 | 242 | 86 | 253 |
| Analog 3 | 0.49 | 83 | 51 | 169 | 102 |
| Analog 4 | 0.68 | 127 | 5119 | 188 | 7584 |

| GTPγS | EC50 (nM) / %efficacy | | | Selectivity | | δ Antagonism | |
|---|---|---|---|---|---|---|---|
| | mu* | delta | kappa | delta/mu | kappa/mu | IC50 | %efficacy |
| Morphine | 3.90 | 1245/ 59% | 2404/ 76% | 319 | 616 | | |
| DAMGO | 1.81 | 3641/ 54% | 13094/ 49% | 2012 | 7234 | | |
| EM1 | 1.82 | >100k | >100k | >50k | >50k | 4287 | 100 |
| EM2 | 8.44 | >100k | >100k | >10k | >10k | 3000 | 88 |
| Analog 1 | 0.43 | >100k | 2179/ 22% | >100k | 5067 | 87 | 92 |
| Analog 2 | 1.50 | 520/ 44% | 12114/ 29% | 347 | 8076 | >100k | - |
| Analog 3 | 0.94 | >100k | 864/ 58% | >100k | 919 | 340 | 88 |
| Analog 4 | 1.01 | >100k | >100k | >100k | >100k | 187 | 75 |

MU OPIOID RECEPTOR AGONIST ANALOGS OF THE ENDOMORPHINS

CROSS-REFERENCE TO RELATED APPLICATIONS

This application is a continuation of U.S. application Ser. No. 14/974,249, filed on Dec. 18, 2015, which is a continuation-in-part of U.S. application Ser. No. 14/268,057, filed on May 2, 2014, which is a continuation of U.S. application Ser. No. 13/477,423, filed on May 22, 2012, now U.S. Pat. No. 8,716,436, which is a continuation-in-part of PCT/US2011/43306, filed on Jul. 8, 2011, which claims the benefit of U.S. Provisional Application Ser. No. 61/363,039, filed on Jul. 9, 2010, each of which is incorporated herein by reference in its entirety.

STATEMENT OF GOVERNMENT SUPPORT

A portion of the work described herein was supported by a Senior Career Research and Merit Award, Grant No. I01BX001489 from the Department of Veteran Affairs, Grant No. DM090595 from the Department of Defense, and Grant No. N00014-09-1-0648 from the Office of Naval Research of the Department of Defense. The United States government has certain rights in this invention.

INCORPORATION OF SEQUENCE LISTING

The biological sequence information in this application is included in an ASCII text file having the file name "TU386CIPSEQ.txt", created on Aug. 24, 2012, and having a file size of 3,011 bytes, which is incorporated herein by reference.

FIELD OF THE INVENTION

The present invention relates to peptide agonists that bind to the mu (morphine) opioid receptor and their use in the treatment of acute and chronic pain.

BACKGROUND OF THE INVENTION

Activation of the mu opioid receptor is among the most effective means of alleviating a wide range of pain conditions. Of the recently cloned opioid receptors e.g., mu opioid receptor ("MOR", Ref. 3,20,21), delta opioid receptor ("DOR", Ref 6,9), and kappa ("KOR", Ref 12-14), the vast majority of clinically used opioids act at the mu receptor. As illustrated in genetically altered "knock-out" mice, the absence of the mu receptor eliminates the analgesic effects of morphine (8), illustrating its central role in opioid-induced pain relief. The unique effectiveness of mu agonists can be attributed to several factors, including their presence in numerous regions of the nervous system that regulate pain processing and activation of multiple mechanisms that limit pain transmission (e.g., inhibiting release of excitatory transmitters from the peripheral nervous system and decreasing cellular excitability in the central nervous system).

Limitations on the use of opioids result from negative side effects, including abuse liability, respiratory depression, and cognitive and motor impairment. Major efforts to develop compounds that maintain analgesic properties while reducing the negative side effects have met with limited success. This is evident from the recent epidemic of prescription drug abuse. Numerous attempts at targeting alternative mechanisms of pain relief to avoid these side effects have generally been met with similar problems, i.e., a profile of adverse effects that are different from opioids, but often sufficiently serious to warrant removal from the market (e.g., COX inhibitors) or lack of approval to enter the market (e.g., TRP receptor antagonists). Over 100 million patients annually in the United States experience acute or chronic pain and frequently do not achieve adequate relief from existing drugs due to limited efficacy or excessive side effects. Elderly patients tend to show greater sensitivity to severe pain and recent guidelines of the American Geriatric Society suggest greater use of opioids and reduction of non-steroidal anti-inflammatory drugs (NSAIDs) (10). Impairment of motor and cognitive function can be more debilitating in the elderly than in younger patients, particularly due to increased risk of fractures (7). Opioids with reduced motor and cognitive impairment are therefore a growing unmet need.

Natural endogenous peptides from bovine and human brain that are highly selective for the mu opioid receptor relative to the delta or kappa receptor have been described (23 and U.S. Pat. No. 6,303,578 which is incorporated herein by reference in its entirety). These peptides are potent analgesics and have shown promise of reduced abuse liability (22) and respiratory depression (4,5), as measured in rodent studies. The limited metabolic stability of the natural peptides led to the development of cyclized, D-amino acid-containing tetrapeptide analogs of the endomorphins (U.S. Pat. No. 5,885,958 which is incorporated herein by reference in its entirety) of sufficient metabolic stability to produce potent analgesia in rodents after peripheral administration. A lead compound from this group reportedly was 3-fold more potent than morphine in alleviating neuropathic pain and showed reduced rewarding properties in animal models that are correlated with abuse potential. While these results are promising, the development of additional compounds showing equal or better properties is desirable. The instant invention addresses this need by providing peptide analogs having unexpectedly better solubility and side-effect profiles than the previously described materials.

SUMMARY OF THE INVENTION

Metabolically stable analogs of the endomorphins, endogenous opioids highly selective for the Mu opioid receptor (MOR) are described herein. Compared to morphine, the pentapeptide and hexapeptide compounds (EM analogs) of Formula I showed dramatically improved analgesia-to-side-effect ratios. At doses providing equal or greater antinociception compared to morphine in the rat, the analogs showed reduced (a) respiratory depression, (b) impairment of motor coordination, (c) tolerance and hyperalgesia, (d) glial p38/CGRP/P2X7 receptor signaling, and (e) reward/abuse potential in both conditioned place preference and self-administration tests. Differential effects on glial activation indicate a mechanism for the relative lack of side effects by the analogs compared to morphine. The results indicate that EM analogs of Formula I provide excellent pain relief mediated by selective MOR activation, but with remarkably safer side effect profiles compared to opioids like morphine.

The EM analogs compounds of Formula I, described below, provide antinociceptive effects equal or greater than morphine with less respiratory depression, motor impairment, tolerance, immune reactivity, and reward/abuse liability, relative to morphine. Opioids, and morphine in particular, induce proinflammatory glial cell, CGRP, or P2X7 receptor activation, which leads to undesirable tolerance to chronic opioid administration, and the need to increase dosages for effective pain relief. The analogs of Formula I do not induce proinflammatory glial cell, CGRP, or P2X7 receptor activation, and thus avoid the tolerance to chronic administration that is associated with opioids. Overall, the EM analogs of Formula I represent a major advance for pain research by surprisingly providing equally effective analgesia compared to morphine, with absent or substantially reduced side effects.

An embodiment of the instant invention is directed to pentapeptide and hexapeptide analogs of endomorphins that differ from the previously described tetrapeptide analogs by having (i) a carboxy-terminal extension with an amidated amino acid, (ii) side-chain to side-chain cyclization, and (iii) in some embodiments, a substitution in position 2. The pentapeptide and hexapeptide analogs of the present invention exhibit increased solubility relative to the tetrapeptides while maintaining favorable therapeutic ratios of analgesia-to-side effects.

The compounds of the present invention are cyclic peptides that act as mu opioid receptor agonists with high affinity. These compounds provide relief of acute pain, chronic pain, or both, and comprise or consist of compounds of Formula I:

(I) H-Tyr-cyclo[$X_1$-$X_2$-$X_3$-$X_4$]-$X_5$. $X_1$ and $X_4$ each independently is an acidic amino acid (i.e., an amino acid comprising a carboxylic acid-substituted side-chain) or a basic amino acid (i.e., an amino acid comprising an amino-substituted side-chain), with the proviso that if $X_1$ is an acidic amino acid (e.g., D-Asp or D-Glu), then $X_4$ is a basic amino acid (e.g., Lys, Orn, Dpr, or Dab), and vice versa. Preferably, $X_1$ is D-Asp, D-Glu, D-Lys, D-Orn, D-Dpr or D-Dab; while $X_4$ preferably is Asp, Glu, Lys, Orn, Dpr or Dab. $X_2$ and $X_3$ each independently is an aromatic amino acid (i.e., an amino acid comprising an aromatic group in the side chain thereof). For example, $X_2$ preferably is Trp, Phe, or N-alkyl-Phe, where the alkyl group preferably comprises 1 to about 6 carbon atoms, i.e., a ($C_1$ to $C_6$) alkyl group. $X_3$ preferably is Phe, D-Phe, or p-Y-Phe where Y is $NO_2$, F, Cl, or Br. $X_5$ is selected from the group consisting of —NHR, Ala-NHR, Arg-NHR, Asn-NHR, Asp-NHR, Cys-NHR, Glu-NHR, Gln-NHR, Gly-NHR, His-NHR, Ile-NHR, Leu-NHR, Met-NHR, Orn-NHR, Phe-NHR, Pro-NHR, Ser-NHR, Thr-NHR, Trp-NHR, Tyr-NHR, and Val-NHR; where R is H or an alkyl group (e.g. a ($C_1$ to $C_{10}$) alkyl group such as methyl, ethyl, propyl, isopropyl, butyl, isobutyl, pentyl, isopentyl, hexyl, isohexyl, heptyl, or isoheptyl). The peptide of Formula I is cyclic (shown as "c[$X_1$-$X_2$-$X_3$-$X_4$]" or "cyclo[$X_1$-$X_2$-$X_3$-$X_4$]" in the formulas described herein) by virtue of an amide linkage between the carboxylic acid and amino substituents of the side chains of amino acid residues $X_1$ and $X_4$. For example, the linkage can be an amide bond formed between the side chain amino group of the D-Lys, D-Orn, D-Dpr, D-Dab, Lys, Orn, Dpr, or Dab with the side chain carboxyl group of D-Asp, D-Glu, Asp, or Glu.

In one embodiment of the invention directed to a peptide of Formula I, $X_5$ is NHR, R is H, and $X_5$ can be —$NH_2$ (i.e., the peptide is an amidated pentapeptide), or Ala-$NH_2$, Arg-$NH_2$, Asn-$NH_2$, Asp-$NH_2$, Cys-$NH_2$, Glu-$NH_2$, Gln-$NH_2$, Gly-$NH_2$, His-$NH_2$, Ile-$NH_2$, Leu-$NH_2$, Met-$NH_2$, Orn-$NH_2$, Phe-$NH_2$, Pro-$NH_2$, Ser-$NH_2$, Thr-$NH_2$, Trp-$NH_2$, Tyr-$NH_2$, or Val-$NH_2$, (i.e., the peptide is an amidated hexapeptide). In one particular embodiment, $X_5$ is $NH_2$. In other particular embodiments, $X_5$ is Ala-$NH_2$, Arg-$NH_2$, Asn-$NH_2$, Asp-$NH_2$, Cys-$NH_2$, Glu-$NH_2$, Gln-$NH_2$, Gly-$NH_2$, His-$NH_2$, Ile-$NH_2$, Leu-$NH_2$, Met-$NH_2$, Orn-$NH_2$, Phe-$NH_2$, Pro-$NH_2$, Ser-$NH_2$, Thr-$NH_2$, Trp-$NH_2$, Tyr-$NH_2$, or Val-$NH_2$.

Another embodiment of the invention is directed to a peptide of Formula I, wherein $X_1$ is D-Asp, D-Glu, D-Lys, or D-Orn; and $X_4$ is Asp, Glu, Lys, or Orn.

Another embodiment of the invention is directed to a compound of Formula I, wherein $X_5$ is NHR and R is a ($C_1$ to $C_{10}$) alkyl.

Another embodiment of the invention is directed to a peptide of Formula I, wherein the aromatic amino acid of $X_2$ is Trp, Phe, or N-alkyl-Phe, and the alkyl group of N-alkyl-Phe is a ($C_1$ to $C_6$) alkyl. In one particular embodiment, $X_2$ is N-methyl-Phe (N-Me-Phe).

Another embodiment of the invention is directed to a peptide of Formula I, wherein the aromatic amino acid residue of either $X_2$ or $X_3$ is Phe, D-Phe, Trp, D-Trp, D-Tyr, N-alkyl-Phe, and the alkyl group of N-alkyl-Phe is ($C_1$ to $C_{10}$) alkyl or p-Y-Phe, wherein Y is $NO_2$, F, Cl, or Br.

Another embodiment of the invention is directed to a peptide of Formula I, wherein the aromatic amino acid of $X_3$ is Phe, D-Phe, or p-Y-Phe, wherein Y is $NO_2$, F, Cl, or Br. In one particular embodiment, $X_3$ is p-Cl-Phe.

Another embodiment of the invention is directed to a peptide of Formula I selected from the group consisting of Tyr-c[D-Lys-Trp-Phe-Glu]-$NH_2$ (SEQ ID NO:1); Tyr-c[D-Glu-Phe-Phe-Lys]-$NH_2$ (SEQ ID NO:2); Tyr-c[D-Lys-Trp-Phe-Glu]-Gly-$NH_2$ (SEQ ID NO:3); Tyr-c[D-Glu-Phe-Phe-Lys]-Gly-$NH_2$ (SEQ ID NO:4); Tyr-c[D-Lys-Trp-Phe-Asp]-$NH_2$ (SEQ ID NO:5); Tyr-c[D-Glu-N-Me-Phe-Phe-Lys]-$NH_2$ (SEQ ID NO:6); and Tyr-c[D-Orn-Phe-p-Cl-Phe-Asp]-Val-$NH_2$ (SEQ ID NO:7).

Another aspect of the invention is directed to a pharmaceutical composition comprising a peptide of Formula I and a pharmaceutically acceptable carrier (e.g., a diluent or excipient).

Yet another aspect of the invention is directed to the use of a peptide of Formula I in a method of treating a patient having a condition that responds to an opioid, or a condition for which opioid treatment is standard in the art. Such a method comprises or consists of administering to the patient an effective amount of a peptide of Formula I of the invention. Particular embodiments of this method can be followed for the purpose of providing at least one effect selected from (i) analgesia (pain relief), (ii) relief from a gastrointestinal disorder such as diarrhea, (iii) therapy for an opioid drug dependence, and (iv) treatment of any condition for which an opioid is indicated. In some embodiments the peptides of Formula I can be used to treat acute or chronic pain. Uses for the peptides of Formula I also include, but are not be limited to, use as antimigraine agents, immunomodulatory agents, immunosuppressive agents or antiarthritic agents. Certain embodiments of the methods of the present invention, such as treatment of pain or opioid drug dependence, are directed to patients having a history of opioid substance abuse. In certain embodiments of the present methods, the peptide is administered parenterally (e.g., intravenous). This invention also relates to a peptide of Formula I for use in one of said methods of treatment.

Another aspect of the invention is directed to a method of activating or regulating a mu-opioid receptor by contacting the mu-opioid receptor with a compound of the invention, as well as the use of the peptide of Formula I in such a treatment.

Another aspect of the invention is directed to a method of measuring the quantity of a mu opioid receptor in a sample using a peptide of Formula I. This method can comprise or consist of the following steps: (i) contacting a sample suspected of containing a mu opioid receptor with a peptide of Formula I to form a compound-receptor complex, (ii) detecting the complex, and (iii) quantifying the amount of complex formed.

Another aspect of the invention is directed to the use of a peptide of Formula I to perform a competitive assay method of detecting the presence of a molecule that binds to a mu opioid receptor. This method can comprise or consist of the following steps: (i) contacting a sample suspected of containing a molecule that binds to a mu opioid receptor with a mu opioid receptor and a peptide of Formula I, wherein the compound and receptor form a compound-receptor complex; (ii) measuring the amount of the complex formed in step (i); and (iii) comparing the amount of complex measured in step (ii) with the amount of a complex formed between the mu opioid receptor and the peptide in the absence of said sample.

Six critical side effects of currently used opioids were surprisingly reduced or absent with the compounds of Formula I: abuse liability, respiratory depression, motor impairment, tolerance, hyperalgesia, and glial activation. This extensive profile of low side effects for peptides shown to cross the blood brain barrier and provide prolonged antinociception is unprecedented. The lack of respiratory depression and motor impairment provides an improved safety profile. The lack of glial activation by a mu agonist, where morphine induces a proinflammatory response, is a novel finding that suggests both a mechanism for the reduced side effects of the analogs and a therapeutic profile with reduced inflammatory complications. The associated reduction in tolerance indicates improved long-term effects. The absence of CPP, and especially SA in the sensitive long-access paradigm, indicates abuse is unlikely. Pain therapy with opioids continues to present troubling questions for doctors and patients who must weigh the risk of causing adverse side effects with effectively alleviating pain. This struggle could be significantly reduced by development of novel opioids with the potent analgesia and low side-effect profile shown by the EM analog compounds of Formula I.

DETAILED DESCRIPTION OF THE INVENTION

Figure 1:
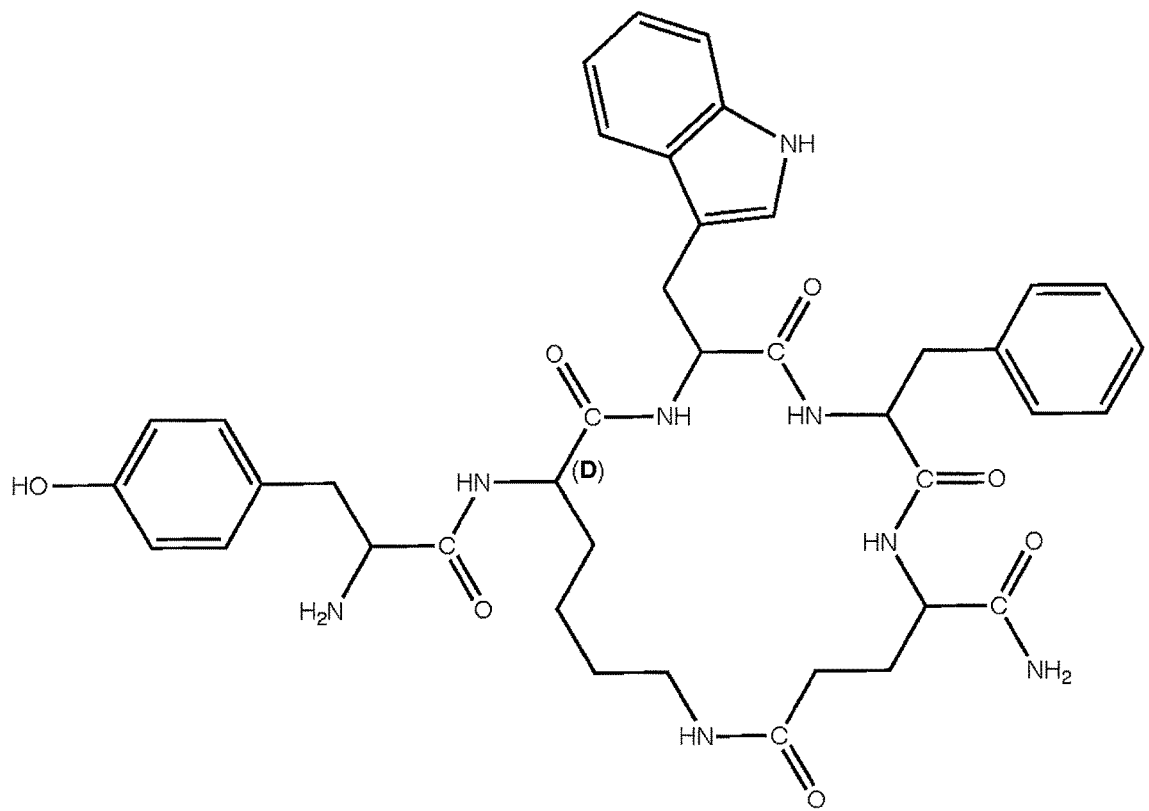
FIG. 1 shows Tyr-c[D-Lys-Trp-Phe-Glu]-NH$_2$ (SEQ ID NO:1), which is described as "Compound 1" in the following disclosure. The structural and basic molecular formulae, as well as the molecular weight (MW), are shown for Compound 1.

Peptides of Formula I, which are cyclic pentapeptide and hexapeptide analogs of endomorphin-1 (Tyr-Pro-Trp-Phe-$NH_2$, SEQ ID NO:8) and endomorphin-2 (Tyr-Pro-Phe-Phe-$NH_2$, SEQ ID NO:9) were prepared. In each case, the cyclic portion of the peptide is formed from amino acid residues 2 through 4, while the Tyr residue (residue 1) is attached to residue 2 as a branch. Non-limiting examples of peptides with the composition of Formula I include Compounds 1-7 below, wherein the side chains of amino acid residues 2 ($X_1$) and 5 ($X_4$) in the sequence are linked by an amide bond between the side-chains thereof. The formulae of Compounds 1, 2, 3, 4, 5, 6, and 7 are shown in Table 1.

TABLE 1

| Compound | H-Tyr- | $X_1$- | $X_2$- | $X_3$- | $X_4$- | $X_5$ | SEQ ID NO: |
|---|---|---|---|---|---|---|---|
| 1 | Tyr- | c[D-Lys | Trp | Phe | Glu] | $NH_2$ | (SEQ ID NO: 1) |
| 2 | Tyr- | c[D-Glu | Phe | Phe | Lys] | $NH_2$ | (SEQ ID NO: 2) |
| 3 | Tyr- | c[D-Lys | Trp | Phe | Glu] | Gly-$NH_2$ | (SEQ ID NO: 3) |
| 4 | Tyr- | c[D-Glu | Phe | Phe | Lys] | Gly-$NH_2$ | (SEQ ID NO: 4) |
| 5 | Tyr- | c[D-Lys | Trp | Phe | Asp] | $NH_2$ | (SEQ ID NO: 5) |
| 6 | Tyr- | c[D-Glu | N-Me-Phe | Phe | Lys] | $NH_2$ | (SEQ ID NO: 6) |
| 7 | Tyr- | c[D-Orn | Phe | p-Cl-Phe | Asp] | Val-$NH_2$ | (SEQ ID NO: 7) |

In some embodiments, the peptides of Formula I includes peptides with an N-alkylated phenylalanine in position 3 ($X_2$). Alkyl groups suitable in the peptides of the present invention include ($C_1$ to $C_{10}$) alkyl groups, preferably ($C_1$ to $C_6$) alkyl groups (e.g., methyl or ethyl). Compound 6 illustrates a cyclic analog whose linear primary amino acid sequence contains an N-methylated phenylalanine in position 3. Other peptides of this invention include compounds wherein the amino acid at position 4 ($X_3$) is p-Y-phenylalanine, wherein Y is $NO_2$, F, Cl or Br, in order to enhance receptor binding and potency. An exemplary peptide (Compound 7), whose linear primary amino acid sequence is provided in SEQ ID NO:7, has a p-chlorophenylalanine (p-Cl-Phe) in position 4.

Figure 2:
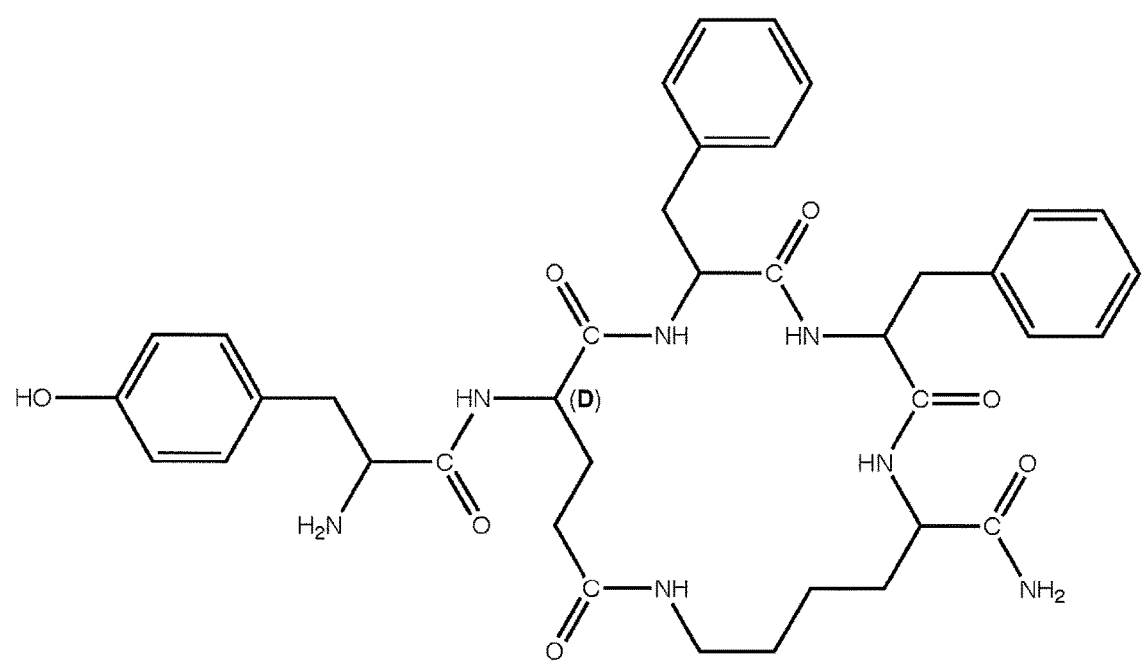
FIG. 2 shows Tyr-c[D-Glu-Phe-Phe-Lys]-NH$_2$ (SEQ ID NO:2), which is described as "Compound 2" in the following disclosure. The structural and basic molecular formulae, as well as the molecular weight (MW), are shown for Compound 2.
Figure 3:
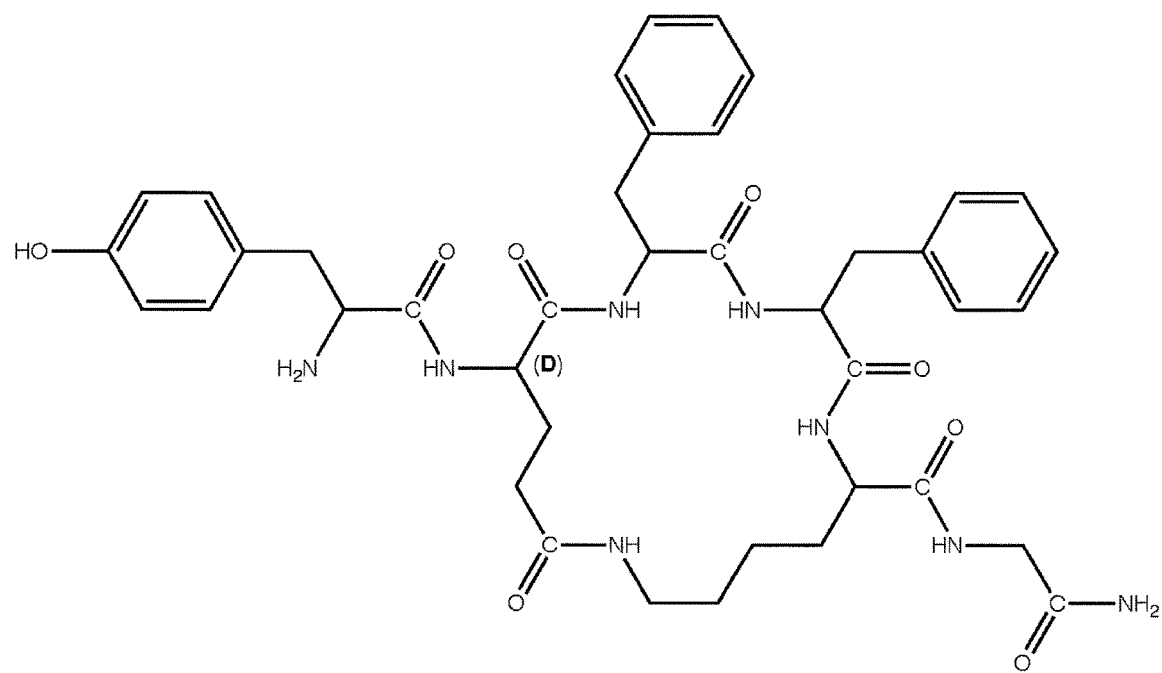
FIG. 3 shows Tyr-c[D-Glu-Phe-Phe-Lys]-Gly-NH$_2$ (SEQ ID NO:4), which is described as "Compound 4" in the following disclosure. The structural and basic molecular formulae, as well as the molecular weight (MW), are shown for Compound 4.

Compounds 1 (FIG. 1), 2 (FIG. 2), 5 and 6 are examples of cyclic pentapeptides, and Compounds 3, 4 (FIG. 3) and 7 are examples of cyclic hexapeptides of the instant invention.

For reference, the abbreviations for amino acids described herein include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), valine (Val), ornithine (Orn), naphthylalanine (Nal), 2,3-diaminopropionic acid (Dpr), and 2,4-diaminobutyric acid (Dab). The L- or D-enantiomeric forms of these and other amino acids can be included in the peptides of Formula I. Other amino acids, or derivatives or unnatural forms thereof such as those listed in the 2009/2010 Aldrich Handbook of Fine Chemicals (incorporated herein by reference in its entirety, particularly those sections therein listing amino acid derivatives and unnatural amino acids) can be used in preparing compounds of the invention.

In Formula I, $X_1$ can be, for example, D-Asp, D-Glu, D-Lys, D-Orn, D-Dpr or D-Dab, and $X_4$ can be, for example, Asp, Glu, Lys, Orn, Dpr or Dab. In general, an amino acid or derivative thereof can be used as $X_1$ or $X_4$ if it contains either an amino group or a carboxyl group in its side chain. In some embodiments, the amino acid used for $X_1$ can be a D-enantiomeric form of such amino acid.

$X_2$ and $X_3$ in Formula I are aromatic amino acids. Examples of such amino acids are unsubstituted or substituted aromatic amino acids selected from the group consisting of phenylalanine, heteroarylalanine, naphthylalanine (Nal), homophenylalanine, histidine, tryptophan, tyrosine, arylglycine, heteroarylglycine, thyroxine, aryl-beta-alanine, and heteroaryl-beta-alanine. Examples of substituted versions of these aromatic amino acids are disclosed in U.S. Pat. No. 7,629,319, which is herein incorporated by reference in its entirety. As used herein, "aromatic amino acid" refers to an α-amino acid comprising an aromatic group (including aromatic hydrocarbon and aromatic heterocyclic groups) in the side-chain thereof.

In some embodiments, $X_2$ in Formula I can be N-alkyl-Phe, where the alkyl group comprises 1 to about 6 carbon atoms. Alternatively, the alkyl group can comprise about 1, 2, 3, 4, 5, 6, 7, 8, 9, or 10 carbons, for example. The alkyl group can be a methyl (i.e., $X_2$ is N-Me-Phe), ethyl, propyl, isopropyl, butyl, isobutyl, pentyl, isopentyl, hexyl, isohexyl, heptyl, or isoheptyl group, or any other branched form thereof, for example. By definition, the alkyl group of N-alkyl-Phe is linked to the α-amino group of phenylalanine. This alpha amino group is involved in an amide bond with the $X_1$ residue in certain peptides of the invention; therefore, the alpha amino group of $X_2$ (when N-alkyl-Phe) as it exists in such peptides is a tertiary amide.

In some embodiments $X_3$ in Formula I is para-Y-Phe (p-Y-Phe), where Y is $NO_2$, F, Cl, or Br, for example. For example, $X_3$ can be p-Cl-Phe. Alternatively, the $NO_2$, F, Cl, or Br groups can be linked in the ortho or meta positions of the phenyl ring of Phe. Any aromatic amino acid incorporated in the compounds of the invention such as at $X_2$ or $X_3$ can have the above groups linked thereto in the ortho, meta, or para positions.

Solubility.

The solubility of the peptides of Formula I (e.g., in saline or physiologic buffer) typically is enhanced relative to the prior art tetrapeptide analogs of the endomorphins. Addition of a hydrophilic amino acid and amidated C-terminus to the relatively hydrophobic tetrapeptide sequences Tyr-cyclo[D-Lys-Trp-Phe] (SEQ ID NO:10) and Tyr-cyclo[D-Lys-Phe-Phe] (SEQ ID NO:11), resulted in an unexpectedly high improvement in solubility while maintaining or improving functionality. For example, Compound 1 was soluble in water, saline and 20% PEG/saline at about 43, 21 and 90 mg/mL, respectively, compared to less than about 2 mg/mL for the previously described compounds. While increases in solubility are associated with improved pharmaceutical delivery properties, higher solubility is also often associated with reduced functional activity (e.g., receptor binding) that may depend on lipophilicity. Surprisingly however, as described in examples below, the functional properties of the compounds of the invention are not diminished, and indeed are generally improved.

Methods of Preparation of the Peptides of Formula I.

The peptides of Formula I can be prepared by conventional solution phase (2) or solid phase (18) methods with the use of proper protecting groups and coupling agents; references 2 and 20 are herein incorporated by reference in their entirety. Such methods generally utilize various protecting groups on the various amino acid residues of the peptides. A suitable deprotection method is employed to remove specified or all of the protecting groups, including splitting off the resin if solid phase synthesis is applied. The peptides can be synthesized, for example, as described below.

Peptides of Formula I were synthesized on Rink Amide resin via Fmoc chemistry. A t-butyl group was used for Tyr, Glu, Asp side chain protection and Boc was used for Lys, Orn and Trp side chain protection. All materials were obtained from EMD Biosciences, Inc (San Diego, Calif.). The peptide was assembled on Rink Amide resin by repetitive removal of the Fmoc protecting group and coupling of protected amino acid. HBTU (O-benzotriazole-N,N,N',N'-tetramethyluronium hexafluorophosphate; CAS #94790-37-1) and HOBT (N-hydroxybenzotriazole; CAS #2592-95-2) were used as coupling reagents in N,N-dimethylformamide (DMF) and diisopropylethylamine (DIPEA) was used as a base. The resin was treated with an aqueous cocktail of trifluoroacetic acid and triisopropylsilane (TFA/TIS/$H_2O$ cocktail) for cleavage and removal of the side chain protecting groups. Crude peptide was precipitated with diethyl ether and collected by filtration.

Cyclization of the linear Fmoc-Tyr-c[$X_1$-$X_2$-$X_3$-$X_4$]-$X_5$ precursors: About 1 mmol of peptide was dissolved in about 1000 mL DMF and about 2 mmol DIPEA was added to the solution, followed by a solution of HBTU (about 1.1 mmol) and HOBT (about 1.1 mmol) in about 100 mL DMF. The reaction mixture was stirred at room temperature overnight. Solvent was removed in vacuo. The resulting solid residue was washed with 5% citric acid, saturated NaCl, saturated NaHCO$_3$, and water. The final solid was washed with diethyl ether and dried under high vacuum.

Preparation of Tyr-c[$X_1$-$X_2$-$X_3$-$X_4$]-$X_5$ peptides. The solids obtained above were dissolved in 20% piperidine/DMF. The mixture was stirred at room temperature for about 1 hour. Solvent was removed in vacuo. Residues were dissolved in 10% aqueous acetonitrile (MeCN/$H_2O$) and lyophilized.

Purification of the crude lyophilized peptides was performed with reverse phase high performance liquid chromatography (RP-HPLC). The HPLC system GOLD 32 KARAT (Beckman) consisting of the programmable solvent module 126 and the diode array detector module 168 was used in the purification and the purity control of the peptides. Reverse phase HPLC was performed using a gradient made from two solvents: (A) 0.1% TFA in water and (B) 0.1% TFA in acetonitrile. For preparative runs, a VYDAC 218TP510 column (250×10 mm; Alltech Associates, Inc.) was used with a gradient of 5-20% solvent B in solvent A over a period of 10 min, 20-25% B over a period of 30 minutes, 25-80% B over a period of 1 minute and isocratic elution over 9 minutes at a flow rate of about 4 mL/min, absorptions being measured at both 214 and 280 nm. The same gradient was used for analytical runs on a VYDAC 218TP54 column (250×4.6 mm) at a flow rate of about 1 mL/min.

Pharmaceutical Preparations.

The instant invention also provides pharmaceutical preparations which contain a pharmaceutically effective amount of the peptides in a pharmaceutically acceptable carrier (e.g., a diluent, complexing agent, additive, excipient, adjuvant and the like). The peptide can be present for example in a salt form, a micro-crystal form, a nano-crystal form, a co-crystal form, a nanoparticle form, a microparticle form, or an amphiphilic form. Salt forms can be, e.g., salts of inorganic acids such as hydrochloride salts, phosphate salts, sulfate salts, bisulfate salts, hemisulfate salts, and the like; or salts of organic acids, such as acetate salts, aspartate salts, citrate salts, fumarate salts, maleate salts, malate salts, lactate salts, hippurate salts, tartrate salts, gluconate salts, succinate salts, and the like. The carrier can be an organic or inorganic carrier, or a combination thereof, which is suitable for external, enteral or parenteral applications. The peptides of the present invention can be compounded, for example, with the usual non-toxic, pharmaceutically acceptable carriers for tablets, pellets, capsules, liposomes, suppositories, intranasal sprays, solutions, emulsions, suspensions, aerosols, targeted chemical delivery systems (15), and any other form suitable for use. Non-limiting examples of carriers that can be used include water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, liquid or aerosol form. In addition auxiliary, stabilizing, thickening and coloring agents and perfumes can be used.

In another aspect, pharmaceutical compositions useful for treating pain and related conditions utilizing the compounds of Formula I are described herein. The pharmaceutical compositions comprise at least one peptide of Formula I in combination with a pharmaceutically acceptable carrier, vehicle, or diluent, such as an aqueous buffer at a physiologically acceptable pH (e.g., pH 7 to 8.5), a polymer-based nanoparticle vehicle, a liposome, and the like. The pharmaceutical compositions can be delivered in any suitable dosage form, such as a liquid, gel, solid, cream, or paste dosage form. In one embodiment, the compositions can be adapted to give sustained release of the peptide.

In some embodiments, the pharmaceutical compositions include, but are not limited to, those forms suitable for oral, rectal, nasal, topical, (including buccal and sublingual), transdermal, vaginal, parenteral (including intramuscular, subcutaneous, and intravenous), spinal (epidural, intrathecal), and central (intracerebroventricular) administration. The compositions can, where appropriate, be conveniently provided in discrete dosage units. The pharmaceutical compositions of the invention can be prepared by any of the methods well known in the pharmaceutical arts. Some preferred modes of administration include intravenous (iv), topical, subcutaneous, oral and spinal.

Pharmaceutical formulations suitable for oral administration include capsules, cachets, or tablets, each containing a predetermined amount of one or more of the peptides, as a powder or granules. In another embodiment, the oral composition is a solution, a suspension, or an emulsion. Alternatively, the peptides can be provided as a bolus, electuary, or paste. Tablets and capsules for oral administration can contain conventional excipients such as binding agents, fillers, lubricants, disintegrants, colorants, flavoring agents, preservatives, or wetting agents. The tablets can be coated according to methods well known in the art, if desired. Oral liquid preparations include, for example, aqueous or oily suspensions, solutions, emulsions, syrups, or elixirs. Alternatively, the compositions can be provided as a dry product for constitution with water or another suitable vehicle before use. Such liquid preparations can contain conventional additives such as suspending agents, emulsifying agents, non-aqueous vehicles (which may include edible oils), preservatives, and the like. The additives, excipients, and the like typically will be included in the compositions for oral administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Pharmaceutical compositions for parenteral, spinal, or central administration (e.g. by bolus injection or continuous infusion) or injection into amniotic fluid can be provided in unit dose form in ampoules, pre-filled syringes, small volume infusion, or in multi-dose containers, and preferably include an added preservative. The compositions for parenteral administration can be suspensions, solutions, or emulsions, and can contain excipients such as suspending agents, stabilizing agents, and dispersing agents. Alternatively, the peptides can be provided in powder form, obtained by aseptic isolation of sterile solid or by lyophilization from solution, for constitution with a suitable vehicle, e.g. sterile, pyrogen-free water, before use. The additives, excipients, and the like typically will be included in the compositions for parenteral administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 100 millimolar, preferably at least about 1 nanomolar to about 10 millimolar.

Pharmaceutical compositions for topical administration of the peptides to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like. The additives, excipients, and the like typically will be included in the compositions for topical administration to the epidermis within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Pharmaceutical compositions suitable for topical administration in the mouth (e.g., buccal or sublingual administration) include lozenges comprising the peptide in a flavored base, such as sucrose, acacia, or tragacanth; pastilles comprising the peptide in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired. The additives, excipients, and the like typically will be included in the compositions of topical oral administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

A pharmaceutical composition suitable for rectal administration comprises a peptide of the present invention in combination with a solid or semisolid (e.g., cream or paste) carrier or vehicle. For example, such rectal compositions can be provided as unit dose suppositories. Suitable carriers or vehicles include cocoa butter and other materials commonly used in the art. The additives, excipients, and the like typically will be included in the compositions of rectal administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

According to one embodiment, pharmaceutical compositions of the present invention suitable for vaginal administration are provided as pessaries, tampons, creams, gels, pastes, foams, or sprays containing a peptide of the invention in combination with carriers as are known in the art. Alternatively, compositions suitable for vaginal administration can be delivered in a liquid or solid dosage form. The additives, excipients, and the like typically will be included in the compositions of vaginal administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Pharmaceutical compositions suitable for intra-nasal administration are also encompassed by the present invention. Such intra-nasal compositions comprise a peptide of the invention in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the peptide. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the peptide. Alternatively, pharmaceutical compositions for administration by inhalation or insufflation can be provided in the form of a dry powder composition, for example, a powder mix of the peptide and a suitable powder base such as lactose or starch. Such powder composition can be provided in unit dosage form, for example, in capsules, cartridges, gelatin packs, or blister packs, from which the powder can be administered with the aid of an inhalator or insufflator. The additives, excipients, and the like typically will be included in the compositions of intra-nasal administration within a range of concentrations suitable for their intended use or function in the composition, and which are well known in the pharmaceutical formulation art. The peptides of the present invention will be included in the compositions within a therapeutically useful and effective concentration range, as determined by routine methods that are well known in the medical and pharmaceutical arts. For example, a typical composition can include one or more of the peptides at a concentration in the range of at least about 0.01 nanomolar to about 1 molar, preferably at least about 1 nanomolar to about 100 millimolar.

Optionally, the pharmaceutical compositions of the present invention can include one or more other therapeutic agent, e.g., as a combination therapy. The additional therapeutic agent will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with a peptide of the present invention.

In another aspect, the present invention provides for the use of the peptides of Formula I for treatment of pain, treatment of discomfort associated with gastrointestinal disorders, and treatment of drug dependence. Methods for providing analgesia (alleviating or reducing pain), relief from gastrointestinal disorders such as diarrhea, and therapy for drug dependence in patients, such as mammals, including humans, comprise administering to a patient suffering from one of the aforementioned conditions an effective amount of a peptide of Formula I. Diarrhea may be caused by a number of sources, such as infectious disease, cholera, or an effect or side-effect of various drugs or therapies, including those used for cancer therapy. Preferably, the peptide is administered parenterally or enterally. The dosage of the effective amount of the peptides can vary depending upon the age and condition of each individual patient to be treated. However, suitable unit dosages typically range from about 0.01 to about 100 mg. For example, a unit dose can be in the range of about 0.2 mg to about 50 mg. Such a unit dose can be administered more than once a day, e.g., two or three times a day.

All of the embodiments of the peptides of Formula I can be in the "isolated" state. For example, an "isolated" peptide is one that has been completely or partially purified. In some instances, the isolated compound will be part of a greater composition, buffer system or reagent mix. In other circumstances, the isolated peptide may be purified to homogeneity. A composition may comprise the peptide or compound at a level of at least about 50, 80, 90, or 95% (on a molar basis or weight basis) of all the other species that are also present therein. Mixtures of the peptides of Formula I may be used in practicing methods provided by the invention.

Additional embodiments of the current invention are directed towards methods of using the peptides of Formula I disclosed herein in medicinal formulations or as therapeutic agents, for example. These methods may involve the use of a single peptide, or multiple peptides in combination (i.e., a mixture). Accordingly, certain embodiments of the invention are drawn to medicaments comprising the peptides of Formula I, and methods of manufacturing such medicaments.

As used herein, the terms "reducing," "inhibiting," "blocking," "preventing", alleviating," or "relieving" when referring to a compound (e.g., a peptide), mean that the compound brings down the occurrence, severity, size, volume, or associated symptoms of a condition, event, or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, or 100% compared to how the condition, event, or activity would normally exist without application of the compound or a composition comprising the compound. The terms "increasing," "elevating," "enhancing," "upregulating", "improving," or "activating" when referring to a compound mean that the compound increases the occurrence or activity of a condition, event, or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, 100%, 150%, 200%, 250%, 300%, 400%, 500%, 750%, or 1000% compared to how the condition, event, or activity would normally exist without application of the compound or a composition comprising the compound.

The following examples are included to demonstrate certain aspects of the invention. It should be appreciated by those of skill in the art that the techniques disclosed in the examples, which represent techniques known to function well in practicing the invention, can be considered to constitute preferred modes for its practice. However, those of skill in the art should, in light of the present disclosure, appreciate that many changes can be made in the specific disclosed embodiments and still obtain a like or similar result without departing from the spirit and scope of the invention. The examples are provided for illustration purposes only and are not intended to be limiting.

Example 1: Binding and Activation of Human Opioid Receptors

The peptides of Formula I showed surprisingly high affinity (subnanomolar) for the human mu opioid receptor with selective binding relative to the delta and kappa opioid receptors. The compounds were tested in standard binding assays using $^3$H-DAMGO (tritiated [D-Ala$^2$, N-Me-Phe$^4$, Gly-ol]-enkephalin; CAS #78123-71-4), $^3$H-DPDPE (CAS#88373-73-3), and $^3$H-U69593 (CAS#96744-75-1) to label mu, delta and kappa receptors, respectively, in membranes from CHO cells expressing human cloned receptors. As shown in Table 2, endomorphin-1 (EM1, SEQ ID NO:8) and endomorphin-2 (EM2, SEQ ID NO:9) are the most selective endogenous mu agonists previously reported. Analogs based on these natural opioids show greater affinity for the mu receptor, albeit with less selectivity. Tetrapeptide endomorphin analogs described earlier (U.S. Pat. No. 5,885, 958; ck1, Tyr-c[D-Lys-Trp-Phe] (SEQ ID NO:10); ck2, Tyr-c[D-Lys-Phe-Phe] (SEQ ID NO:11)) are also shown. Peptides of Formula I, which include an amidated carboxy-terminus (Compounds 1, 2, 5) retained high affinity binding, but increased selectivity for the mu receptor.

TABLE 2

Compound binding to opioid receptors.

| | $K_i$ (nM) | | | Selectivity | |
| --- | --- | --- | --- | --- | --- |
| | Mu | Delta | Kappa | Delta/Mu | Kappa/Mu |
| Morphine | 0.92 | 242 | 56 | 264 | 61 |
| DAMGO | 0.78 | 589 | 334 | 754 | 429 |
| EM1 | 2.07 | 1215 | >10000 | 587 | >5000 |
| EM2 | 1.32 | 5704 | >10000 | 4328 | >5000 |
| ck1 | 0.32 | 28 | 35 | 90 | 111 |
| ck2 | 0.36 | 3 | 12 | 9 | 33 |
| Compound 1 | 0.49 | 132 | 128 | 267 | 260 |
| Compound 2 | 0.73 | 69 | 71 | 94 | 98 |
| Compound 5 | 0.43 | 140 | 29 | 328 | 67 |

Receptor Activation: GTPγS Functional Assay.

Figure 4:
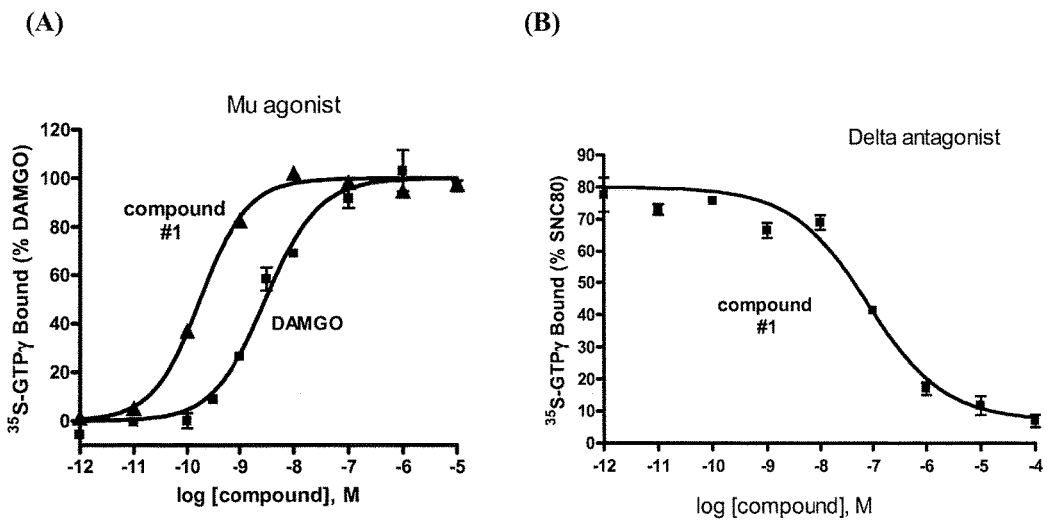
FIG. 4 shows opioid receptor binding activity for Compound 1. (A) mu receptor binding of "Compound 1" (triangles) or DAMGO (squares). (B) Antagonist activity of Compound 1 against binding of SNC80 to delta receptor.

Functional activation of the three opioid receptors was tested in standard assays in which the non-hydrolysable GTP analog, $^{35}$S-GTPγS, was used to quantify activation of cloned human opioid receptors expressed in cell membranes. FIG. 4, Panel A shows that Compound 1 is a full efficacy agonist with significantly greater potency than the reference compound, DAMGO. FIG. 4, Panel B shows that Compound 1 exhibits unexpected full efficacy as a delta antagonist; i.e., it is able to inhibit the delta activation produced by an $ED_{80}$ dose of the reference delta agonist, SNC80 (CAS #156727-74-1). Table 3 shows that all agonists tested are potent activators of the mu receptor, with $EC_{50}$ (median effective concentration) values at low-nanomolar to sub-nanomolar concentrations. All compounds were found to be full efficacy (>90%) agonists at the mu receptor. The endomorphins and the compounds of Formula I of the invention show remarkable selectivity for receptor activation, with delta activation below 50% at concentrations up to 10 μM, reflecting selectivity >100000. Compounds 1 and 3, however, showed full efficacy delta antagonism; Compound 1 exhibited this antagonism at a relatively low concentration.

TABLE 3

Opioid receptor activation by compounds.

| | Agonist $EC_{50}$ (nM) | | | Selectivity | | Delta Antagonist | |
|---|---|---|---|---|---|---|---|
| | mu | delta | kappa | delta/mu | kappa/mu | IC 50 | efficacy |
| MS[a] | 3.90 | 1245 | 2404 | 319 | 616 | | |
| DAMGO | 1.98 | 3641 | 13094 | 1839 | 6613 | | |
| ck1 | 0.21 | 138 | 469.51 | 658 | 2236 | | |
| ck2 | 0.15 | 7 | 206.11 | 44 | 1374 | | |
| EM1 | 1.82 | >100000 | >100000 | >50000 | >50000 | 4287 | 100 |
| EM2 | 8.44 | >100000 | >100000 | >10000 | >10000 | 30000 | 88 |
| Comp. 1 | 0.15 | >100000 | 963.79 | >500000 | 6425 | 105 | 93 |
| Comp. 2 | 0.99 | >100000 | 12114.00 | >100000 | 12236 | 2750 | 51 |
| Comp. 5 | 0.22 | >100000 | 740.34 | >400000 | 3365 | 557 | 100 |

[a]morphine sulfate

Receptor Activation: Beta-Arrestin Recruitment.

Beta-arrestin is an intracellular protein that is recruited to the mu opioid receptor following activation by agonists. It has been shown to activate intracellular signaling pathways that in many cases are independent of well-known G-protein mediated pathways. It has recently been shown that beta-arrestin knockout mice exhibit altered responses to morphine, including increased analgesia and decreased side effects such as tolerance, respiratory depression, and constipation (16). These results indicate that the analgesic and side-effects of morphine are separable by manipulation of cell signaling processes. These findings also provide support for the recent concept known variously as "functional selectivity", "biased agonism", "agonist directed signaling" and other descriptions. According to this concept, agonists capable of producing a different cascade of signaling at a given receptor could produce a different profile of desired and undesired effects relative to other agonists for that receptor. Three of the analogs of this invention were tested and showed patterns of beta-arrestin recruitment (ranging from high potency with low efficacy to moderate potency with significant efficacy) that were different from each other and from morphine. Together with the differential analgesic/side-effect profiles relative to morphine described in previous examples, the beta arrestin results suggest that these compounds exhibit "functional selectivity", favoring analgesia over adverse side-effects.

Beyond the value of high mu agonist selectivity (i.e., exclusion of potential side-effects resulting from activation of multiple receptors), delta antagonism is expected to attenuate opioid-induced tolerance, dependence, and reward. As first shown in 1991 (1) and supported in numerous studies since, delta antagonists can reduce morphine-induced tolerance and dependence, while maintaining or enhancing analgesia. Recent studies (11) have also shown reduced rewarding properties of mu agonist/delta antagonists as reflected in the conditioned place preference (CPP) test described below. The activity of the peptides of Formula I (e.g., Compound 1) as mu agonists/delta antagonists as well as at mu/delta receptor dimers indicate that the peptides will produce effective analgesia with reduced tolerance, dependence, and reward (18).

Example 2: Providing Analgesia of Greater Duration, but with Reduced Respiratory Depression, Relative to Morphine after Intravenous Administration Respiratory depression is a major safety issue in the use of opioids. An opioid providing analgesia as effective as that produced by morphine, but with less respiratory depression, would be a major advance for the safe use of opioid analgesics. Effectiveness after systemic administration, such as intravenous (i.v.) injection, is unusual for peptide-based compounds, and would be critical for the clinical utility thereof. Two peptides (Compounds 1 and 2) were tested for their effects on respiration (minute ventilation) and duration of antinociception relative to morphine. Rats with indwelling jugular catheters were placed in a BUXCO whole body plethysmograph apparatus for determining multiple respiratory parameters. For 20 minutes following i.v. injection of vehicle (saline), baseline minute ventilation was determined. Animals were then injected with morphine or test compound and changes from baseline were determined for 20 minutes, the period of maximal inhibition of minute ventilation by all compounds. The standard tail-flick (TF) test was used to determine antinociception. A baseline test was conducted before placing the animal in the BUXCO chamber, at the end of the 20-minute respiratory test, and at every 20 minutes thereafter until the TF latency returned to below 2× baseline TF. Baseline latencies were 3-4 seconds and a cut-off time ("maximal antinociception") was set at 9 seconds to avoid tissue damage.

Figure 5:
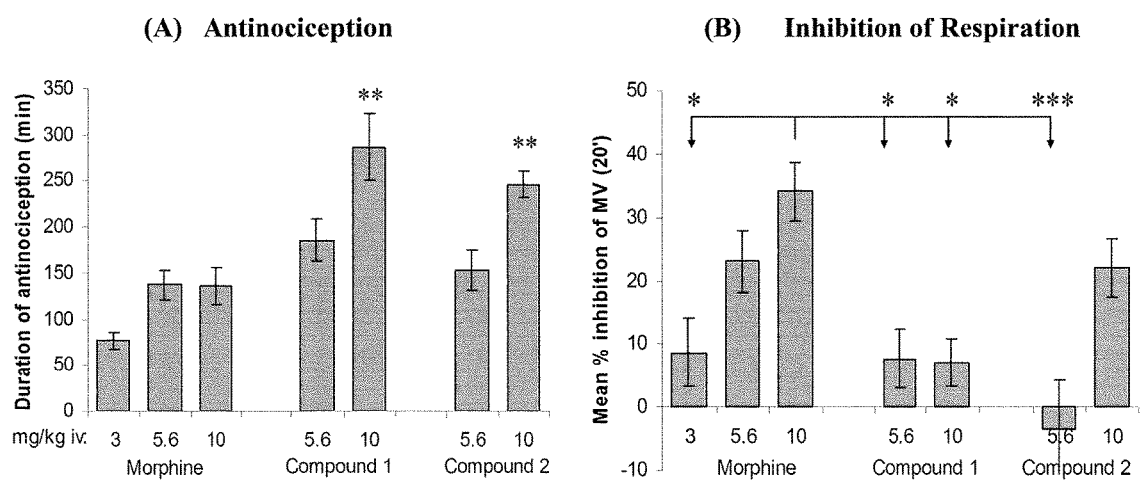
FIG. 5 shows effects of compounds on antinociception and respiration. (A) Effects of Compounds 1 and 2 on antinociception as compared with morphine. **=p<0.01. (B) Effects of Compounds 1 and 2 on respiratory minute volume (MV) over a 20-minute period as compared to morphine. * p<0.05, *** p<0.001.

FIG. 5, Panel A shows that 10 mg/kg doses of Compounds 1 and 2 produced significantly longer antinociception than all other treatments (**=p<0.01) and 5.6 mg/kg doses produced antinociception similar to the 10 mg/kg dose of morphine. Despite the greater antinociceptive effect of Compounds 1 and 2, significantly (* p<0.05) less inhibition of respiration was observed in both doses of Compound 1 and in the 5.6 mg/kg dose of Compound 2 (FIG. 5, Panel B). These results indicate an unexpected and clearly safer therapeutic profile for the peptides of Formula I over the current standard opioid analgesic.

Example 3: Providing Analgesia of Greater Duration than Morphine with Reduced Impairment of Neuromotor Coordination and Cognitive Function Neuromotor and cognitive impairment are characteristics of opioids that are of particular importance in two populations, i.e., military combat troops, where escape from immediate danger can require unimpaired motor and cognitive skills, and the elderly, where these impairments can exacerbate compromised function including impaired balance, which can lead to increased risk of fractures.

Example 3a: Neuromotor Coordination

Figure 6:
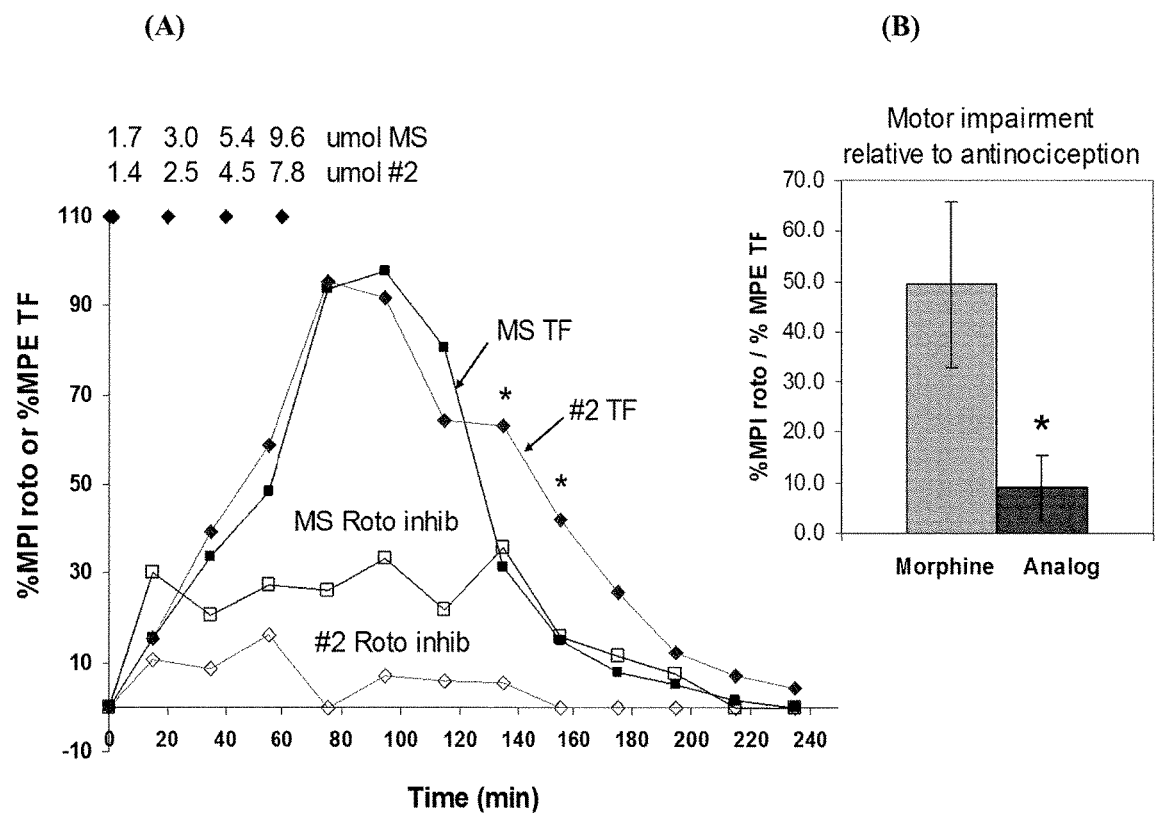
FIG. 6 shows the effects of Compound 2 on antinociception and motor impairment. (A) The effects of Compound 2 (filled triangles) and morphine sulfate (MS, filled squares) on antinociception were measured by the tail flick (TF) test. Also, the effects of Compound 2 (open triangles) and morphine sulfate (open squares) on motor behavior were measured. (*=p<0.05). (B) The bar graph shows the ratio of the area under the curve (AUC) for percent motor impairment relative to the AUC for percent antinociception. This ratio is significantly greater (*p<0.05) for morphine than for Compound 2, consistent with greater motor impairment relative to analgesia for morphine.

FIG. 6, Panel A illustrates that Compound 2 produces significantly greater antinociception, but significantly reduced motor impairment, relative to morphine (MS). Both compounds were administered by cumulative intravenous (i.v.) doses in rats. Increasing quarter-log doses were given every 20 minutes, and a tail flick (TF) test (a test of latency to remove the tail from a hot light beam) followed by a rotorod test were conducted about 15 minutes after each injection. Escalating doses were given until each animal showed greater than 90% maximum possible effect (% MPE) on the TF test, determined as: [(latency to TF minus baseline latency)/(9 sec maximum (cut off) time to avoid tissue damage) minus baseline)]×100. The animal was then placed on a rod that rotated at speeds escalating to 13 revolutions per minute (RPM) over 3 minutes, and the latency to fall from the rod was determined. Only animals that consistently remained on the rod for the full 180 seconds during training in the drug-naïve state were tested. % Maximum Possible Inhibition (% MPI) of motor coordination was determined as 100−(latency to fall/180×100).

The two compounds showed similar onset to maximal antinociception, but Compound 2 produced significantly longer antinociception, as reflected by TF latencies significantly (*=p<0.05) longer than those of the morphine group at 135 and 155 minutes (FIG. 6, Panel A). Despite this greater antinociception, the motor impairment was significantly less than that of morphine (FIG. 6, Panel B, * p<0.05). The impairment of motor behavior by morphine was significantly above that of vehicle controls (* p<0.05) while that of Compound 2 was not.

Example 3b: Cognitive Impairment

A widely used standard test of cognitive function is the Morris Water Maze (MWM). During training, rats learn to find a hidden escape platform based on spatial memory. Average latency to the platform, as well as average distance from the platform (a measure unaffected by swim speed), decrease as the task is acquired and provide indices of spatial memory. After 4 days of training, an injection of morphine produced impairment of spatial memory, as reflected by a significant increase in the latency to, and average distance from, the platform. By contrast, Compound 2, at doses that provide equal or greater antinociception than morphine, did not produce significant impairment. These results indicate an unexpected and superior therapeutic profile of the peptides of Formula I with regard to cognitive function relative to the current standard opioid analgesic.

Example 4: Providing Analgesia of Greater Duration, but Reduced Reward, Relative to Morphine Opioids remain the standard treatment for relief of severe pain, but diversion of pain medications for non-pain use has become a serious national problem (see U.S. Department of Health and Human Services Substance Abuse and Mental Health Services Administration, found at world wide website oas(dot)samhsa(dot)gov/2k9/painRelievers/nonmedicalTrends(dot)pdf). Considerable efforts in academia and industry have focused on "tamper-proof" versions of opioid medications, but there has been little success in developing opioids that provide highly effective analgesia with minimal abuse potential. The conditioned place preference (CPP) paradigm is a widely accepted model for demonstrating rewarding properties of drugs, and all major classes of abused drugs produce CPP, including opioids such as morphine and heroin. Briefly, animals are first allowed, on Day 1, to freely explore a 3-compartment apparatus consisting of a small "start box" and two larger compartments that are perceptually distinct (gray vs. black and white stripes in this example). For the next three days, the animals are given an i.v. injection of drug and confined to one compartment, and vehicle is given in the other. The time at which the drug or vehicle is given (a.m. or p.m.) is counterbalanced, as is the compartment in which the drug is given (preferred or non-preferred, as determined during the baseline test). This unbiased design allows for detection of both drug preference and drug aversion. After three days of conditioning (Days 2, 3 and 4), the animal is allowed free access to all compartments on Day 5 in the drug-free state and the change in absolute time and proportion of time spent in the drug-paired compartment are determined. A significant increase in the time or proportion of time spent in the drug-paired compartment on the post-conditioning test day relative to that on the pre-conditioning baseline test is interpreted as a conditioned place preference, reflective of rewarding properties and potential abuse liability.

Figure 7:
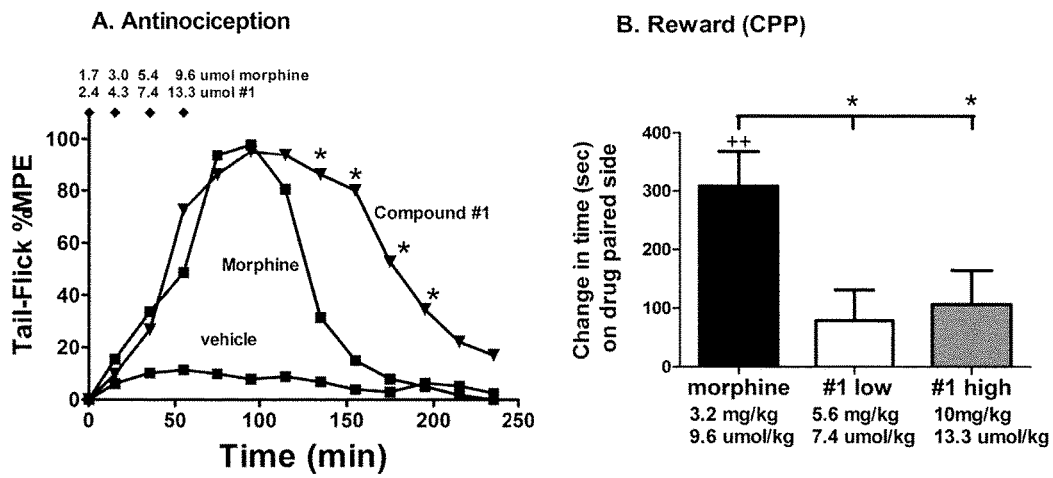
FIG. 7 shows the effects of compounds on drug abuse liability. (A) The effects of Compound 1 (filled triangles), morphine (filled squares), and vehicle (filled circles) on antinociception were measured by the tail flick (TF) test. * p<0.05. (B) The cumulative doses of either morphine or Compound 1 that were shown to produce maximal antinociception as shown in (A) were tested for the ability to induce conditioned place preference (CPP). *** p<0.01.

When the cumulative doses of either morphine or Compound 1 that were shown to produce maximal antinociception (FIG. 7, Panel A) were tested for the ability to induce CPP (FIG. 7, Panel B), morphine produced a significant (*** p<0.01) increase in the time spent on the drug side, while Compound 1 did not, even though significantly (* p<0.05) greater antinociception (FIG. 7, Panel A) was observed with Compound 1 from about 140 to 180 minutes after its injection. Compounds 2 and 5 also showed no significant CPP at doses producing antinociception equal to those of morphine that produced CPP. In a complementary paradigm in which rats were provided access to morphine or EM analogs for self-administration, access to morphine, but not analogs, resulted in significant self-administration. These findings are consistent with less abuse liability for the novel analogs relative to morphine.

Example 5: Alleviation of Chronic Pain

Figure 8:
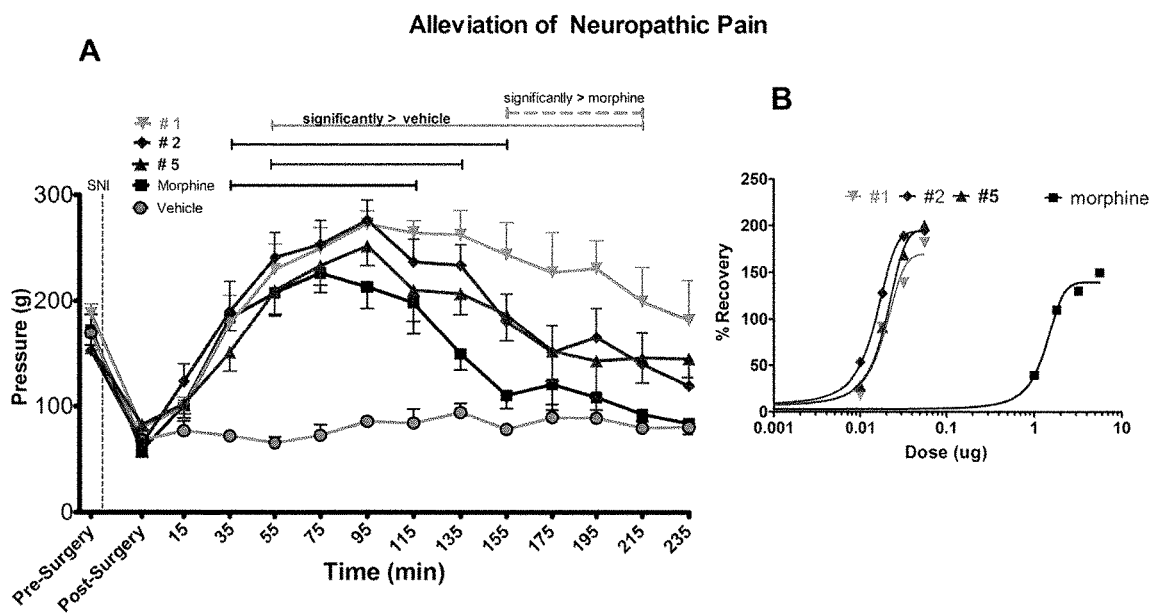
FIG. 8 shows the duration and relative potency of compounds in reversing chronic pain induced by nerve injury (neuropathic pain). (A) The decrease in paw pressure required for withdrawal after nerve injury surgery was reversed by morphine and Compounds 1, 2, and 5 (squares, down triangles, diamonds, and up triangles, respectively). Times at which the reversal was significantly above vehicle (p<0.05 to 0.001) are shown in bars at the top. Scores for Compound 1 were also significantly above those of morphine from 155 to 215 min (dashed bar). Compound 5 showed similar reversal (80 min) relative to morphine, and Compounds 1 and 2 showed significantly longer reversal (120 and 260 min, respectively) relative to morphine. (B) Dose-response curves show that all three analogs are significantly more potent than morphine, as determined by the dose required to fully (100%) reverse hyperalgesia (pre-surgical minus post-surgical pressure).

Chronic pain affects a large proportion of the population. One form of chronic pain, neuropathic pain, is particularly difficult to treat. FIG. 8 shows that Compounds 1, 2 and 5 provide unexpectedly potent relief of neuropathic pain induced by the spared nerve injury (SNI) model in the rat. As demonstrated in FIG. 8, Panel A, prior to SNI surgery ("pre-surgery"), an average pressure of about 177 g applied to the hindpaw with a Randall-Selitto device was required to elicit a paw withdrawal response. About 7 to 10 days post-surgery, the animals showed hyperalgesia, indicated by a reduction in the average pressure (to about 70 g) required to elicit withdrawal. Drugs were administered as intrathecal cumulative doses chosen to produce full alleviation of the hyperalgesia. Times at which the reversal was significantly ($p<0.05$ to $0.001$) above vehicle are shown in bars at the top. Compound 5 showed similar reversal times (about 80 min), and Compounds 1 and 2 showed significantly longer reversal times (about 120 and 260 min, respectively) relative to morphine (about 80 min). Scores for Compound 1 were also significantly above those of morphine from 155-215 min (dashed bar). Dose-response curves (FIG. 8, Panel B) showed that all three analogs are significantly more potent than morphine, as determined by the dose required to fully (100%) reverse the hyperalgesia, i.e., return to the pre-surgical baseline response (pre-surgical minus post-surgical pressure). Compounds 1, 2, and 5 reversed mechanical hypersensitivity at doses about 80-fold to 100-fold lower than morphine (about 0.01 to 0.014 µg compared to about 1.14 µg for morphine). On a molar basis, this represents about 180 to 240 fold greater potency than morphine against neuropathic pain. Similar results were observed after other forms of chronic pain including post-incisional (post-operative) and inflammatory pain induced by Complete Freund's Adjuvant (CFA). The foregoing examples are illustrative, but not exhaustive, as to the types of acute or chronic pain for which the peptides of Formula I are effective.

Example 6. Reduced Tolerance and Glial Activation Relative to Morphine

A major limiting factor for the usefulness of opioid medications is tolerance, which requires increasing doses to maintain an analgesic effect. Reduction of the potential for tolerance would be a very important advantage for a novel analgesic. In addition, several recent studies have shown that repeated opioid exposure sometimes leads to "paradoxical" opioid-induced pain. Increased responsiveness to normally noxious stimuli (hyperalgesia) or normally non-noxious stimuli such as touch (allodynia) have been reported. Explanations for the tolerance and opioid induced hypersensitivity include the possibility that activation of glia, a reflection of an inflammatory response, results in an increased release of substances that activate or sensitize neuronal transmission of nociceptive signals. Specifically, enhanced release of "pro-nociceptive" cytokines and chemokines are thought to mediate the enhanced pain sensitivity sometimes observed after chronic exposure to opioids. In addition, several studies have linked this phenomenon to opioid tolerance based on the concept that increasing doses of opioids are required to overcome the increased pronociceptive effects of the released compounds. Described below are the unexpected findings that: (1) Compounds 1, 2 and 5 produce significantly less tolerance relative than morphine, and (2) that in direct comparison to morphine, and in contrast to morphine and most clinically used opioids, the analogs do not induce an inflammatory glial activation response after chronic administration. In addition to their potential value for reduced escalation of doses required during chronic administration, the analogs of Formula I could be ideal for opioid rotation and for a wide range of situations where ongoing inflammatory conditions may be exacerbated by treatment with morphine. This approach would also be superior to use of an anti-inflammatory agent as an adjuvant to opioid treatment.

Figure 9:
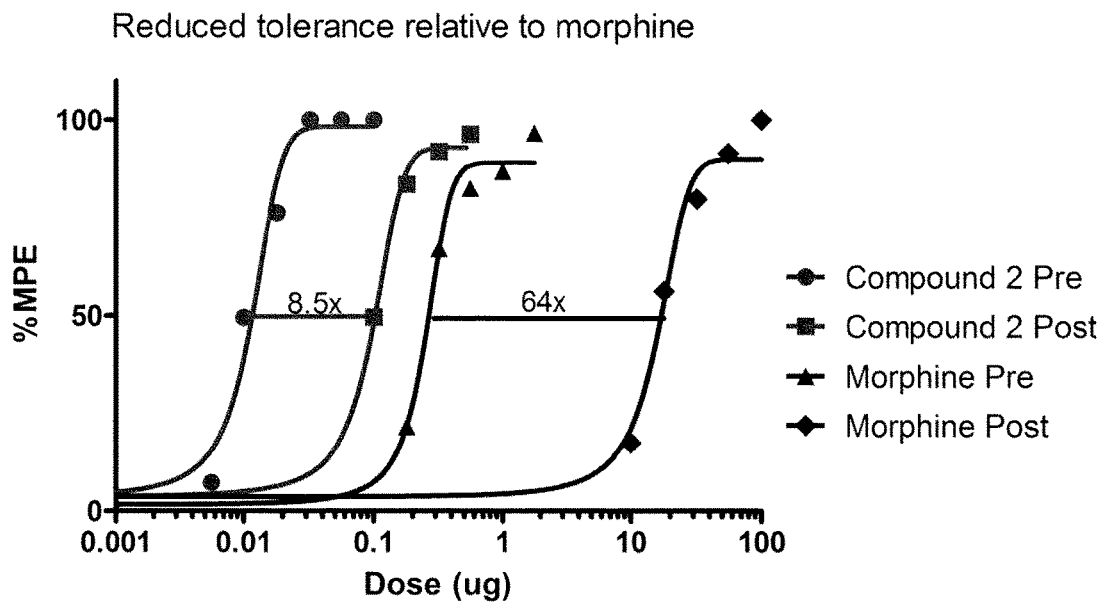
FIG. 9 shows the extent of tolerance produced by intrathecal delivery of morphine or Compound 2 for 1 week via an osmotic minipump. Cumulative dose-response curves (four increasing quarter-log doses) were used and responses expressed as % maximum possible effect (% MPE) in a tail-flick test were determined before and after implantation of a minipump. The shift in ED$_{50}$ after Compound 2 (about 8.5-fold) was significantly less than that after morphine (64 fold), consistent with reduced induction of tolerance by the analog. Similar results were observed with Compounds 1 and 5.

Compounds 1, 2 and 5 all showed greater potency, reduced tolerance and reduced glial activation relative to morphine. For simplicity, only Compound 2 is shown in comparison to morphine in FIG. 9. The experiment was designed to model clinical use of opioids by titrating to full antinociception in each subject, and maintaining steady blood levels, in this case through use of osmotic minipumps. Doses producing matched initial antinociception were determined for morphine and analog by intrathecal injection of the cumulative dosing paradigm described above for the rotorod and neuropathic pain models. Doses were increased until each rat achieved full antinociception (100% MPE). The $ED_{50}$ for all compounds in opioid naïve animals was determined and Compound 2 was found to be over 20-fold more potent ($p<0.001$) than morphine ($ED_{50}=0.01$ µg±0.001 compared to 0.253 µg±0.05 for morphine, n=5-7). This translates on a molar basis to about 40-fold greater potency for the analog. Immediately after the first test, ALZET osmotic minipumps (Durect Corp, Cupertino, Calif.) were implanted subcutaneously and connected to the intrathecal catheter. The primed pumps delivered morphine or analog at 2 µg/hr or 0.056 µg/hr for about 7 days, respectively. The 2 µg/hr morphine dose was chosen based on previous studies in which this dose was shown to produce glial activation in the dorsal horn in a similar paradigm (19). The dose of analog was chosen using a similar ratio to the $ED_{50}$ (about 7× to 8×). A second cumulative dose-response curve was generated on Day 7 after minipump implantation to determine the shift in $ED_{50}$ as an index of relative tolerance. As shown in FIG. 9, the $ED_{50}$ of morphine shifted to 16±3.3 µg (over 60-fold) while that of compound 2 shifted only about 8.5 fold to about 0.11±0.02 µg. Compounds 1 and 5 showed similar results with potencies over 20× greater than morphine and shifts less than 20 fold. These results show that EM analogs cause unexpected and significantly less tolerance than morphine.

Figure 10:
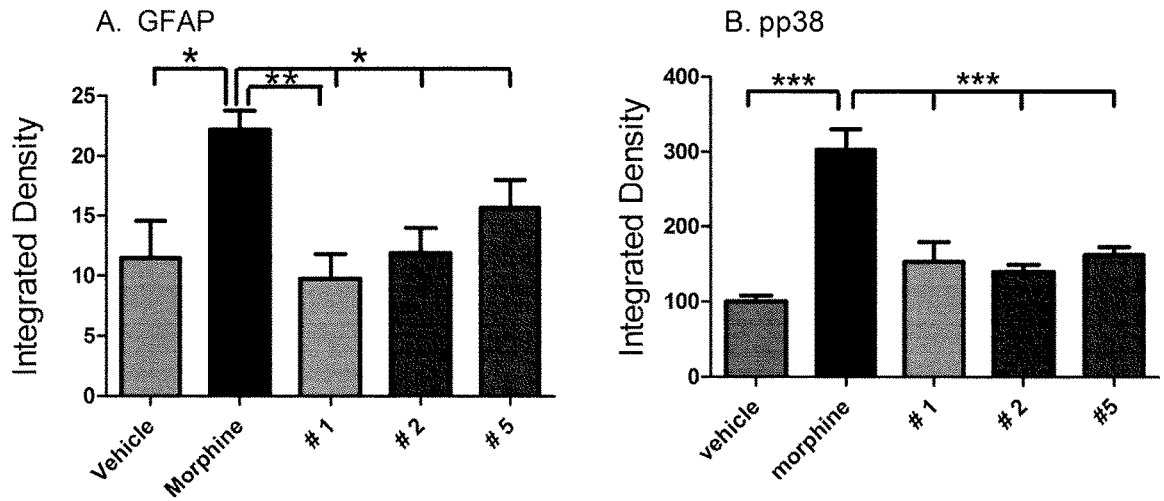
FIG. 10 shows activation of glia after 1 week of treatment with morphine but not analogs. Integrated density of GFAP (A) and pp38 (B) staining in morphine-treated, but not analog-treated rats, is significantly increased relative to those given vehicle. In addition, the density of staining after morphine is significantly greater than that after analogs (*, , *=p<0.05, 0.01, 0.001, respectively; n=5-7).

As shown in FIG. 10, morphine produced significant glial activation, but for all 3 analogs, activation was not significantly different from vehicle and was significantly less than morphine, establishing differential glial effects for morphine compared to EM analogs (Compounds, 1, 2, and 5). Rats used in the above tolerance experiment were perfused after the final behavioral test and analyzed for glial activation as indicated by (A) GFAP staining for astroglia and (B) phospho-p38, a signaling pathway activated in microglia by morphine. Five sections from each of 5-7 animals/group were analyzed for integrated density of staining with the IMAGE J program. Morphine, but none of the analogs, showed significantly greater induction than vehicle. Values for all analogs were significantly below those of morphine (*, , *=$p<0.05$, 0.01, 0.001, respectively, compared to indicated groups). These data provide evidence that, at doses producing equal or greater antinociception, the analogs produce unexpectedly less glial activation and this is associated with reduced tolerance.

Example 7. Evaluation of a Hexapeptide Analog of Formula I Relative to Pentapeptides Chemicals: A series of pentapeptide and hexapeptide compounds of Formula I, i.e., Compounds 1 (SEQ ID NO: 1), 2 (SEQ ID NO; 2), 5 (SEQ ID NO: 5), and 3 (SEQ ID NO: 3) described above (referred to hereinafter in this Example as Analog 1, Analog 2, Analog 3, and Analog 4, respectively) were synthesized by standard solid phase methods at 1 mMol on a Rink amide resin via fluorenylmethyloxycarbonyl (Fmoc) chemistry with purity (>95%) and sequence identity confirmed by HPLC and MS. Analogs selected for full characterization (FIG. 11, Panel A) were synthesized at 2 g scale. Morphine sulfate and beta-funaltrexamine (β-FNA) were supplied by NIDA, naloxone and naloxone methiodide (Nlx-M) were obtained from Sigma (St. Louis, Mo.), naltrindole (NTI) and nor-binaltorphimine (nBNI) from Tocris (Ellisville, Mo.), and Tyr-D-Ala$^2$-N-MePhe$^4$-Gly-ol (DAMGO) from Bachem (King of Prussia, Pa.).

Receptor binding assays were conducted using cloned human receptors in CHO-K1 cell membranes and the following ligands for mu, delta, and kappa opioid receptors (MOR, DOR KOR), respectively: $^3$H-DAMGO, $^3$H-DPDPE and $^3$H-U69593. Membranes, radioligands at their Kd concentrations, and varying concentrations of test compounds were incubated in 50 mM Tris pH 7.4, 5 mM MgCl$_2$, 10 μg/mL saponin, for 60 min at 25° C., filtered over GF/B filters and counted in MICROSCINT 20 scintillation cocktail (Packard).

Activation of receptors was determined in GTPγS assays. CHO-K1 cell membranes, as described above, were mixed with GDP (1 μM for MOR, 10 μM for DOR and KOR) for 15 min on ice followed by incubation with $^{35}$S-GTPγS (0.1 nM) and scintillation proximity assay (SPA) beads in 20 mM HEPES (pH 7.4) containing 10 mM saponin, MgCl$_2$ (1 mM for MOR and DOR, 30 mM for KOR) and 100 mM NaCl. After shaking for 2 min and centrifugation (2000 rpm, 10 min), samples were incubated for 1 hour (hr) and counted. Percent efficacy was calculated relative to activation by reference compounds DAMGO, SNC80, and U-50488 for mu, delta and kappa receptors. All test compounds showed >95% efficacy at MOR. DOR antagonism was assessed by inhibition of the activation produced by SNC80 at its EC$_{50}$.

Stability in 37° C. Plasma and Saline.

To test analog degradation by human and rat plasma enzymes in vitro, pooled normal human plasma was obtained from Innovative Research (Novi Mich., cat. #IPLA-N) and rat aortic blood was drawn in a 10 ml syringe rinsed with heparin, incubated at room temperature 1 hr and centrifuged (2000 g×15', 4° C.). Analogs were incubated at 200 μg/ml in fresh plasma 37° C. Aliquots (75 μL=7.5 μg) of the mixture were withdrawn at various times and immediately added to 75 μL ice cold 0.1M HCl, and centrifuged at 30,000 g, 20 min, 4° C. Aliquots (100 μL, about 5 μg) of the supernatant were frozen pending HPLC analysis. Samples were diluted with 100 μL 0.1% TFA in water and analyzed on a Beckman System GOLD HPLC with a VYDAC 218TP54 C18 column using eluents comprising 0.1% TFA in water/acetonitrile (AcN) mixtures. The samples were run at 1 mL/min in gradients of 5-20% AcN/10 min, 20-25% AcN/30 min, 25-60% AcN/1 min, 60% AcN/9 min, and 60-80% AcN/1 min with an absorbance detector and absorbance was plotted as a function of elution time. Intact peptide was calculated from area under the absorbance curve at the appropriate retention time relative to a standard curve generated with the same conditions. Degradation was calculated by linear regression of n log A/A$_0$ at 280 nm absorbance. To test analog stability as an injectable solution at physiological temperature, Analog 4 was sterile-filtered and incubated at 37° C. in sterile saline (10 μg/100 μL). Aliquots were removed at various times and analyzed by HPLC. Confirmation of peptide MW/integrity was conducted on an Applied Biosystems VOYAGER-DE PRO mass spectrometer.

Animals and Surgery:

Male CD-1 mice (22-25 g) and Sprague-Dawley rats (250-400 g, Charles River, Wilmington, Mass.) were housed in a 12-h light/dark cycle. All experiments were approved by the Tulane Institutional Animal Care and Use Committee and conducted according to the NIH Guide for the Care and Use of Laboratory Animals. All efforts were made to minimize animal suffering, and to reduce the number of animals used. No alternatives to in vivo techniques are available. Drug injections to rats were given as described previously through indwelling jugular vein (i.v.) (55) or intrathecal (i.t.) catheters (60). Mice received subcutaneous (s.c.) injections at the nape of the neck or oral administration by gavage.

Antinociception was determined in a standard tail flick (TF) test wherein the latency to withdraw the tail from a heat source was automatically measured (IITC, Woodland Hills, Calif.). Baseline latencies were 3-4 sec with a cutoff time of 9 sec to prevent tissue damage. Percent Maximum Possible Effect (% MPE) was determined as [(latency-baseline latency)/(9-baseline latency)]*100. Equi-antinociceptive asymptotic doses of morphine and analogs producing >95 MPE were used in the CPP test. Doses of morphine and Analog 4 were tested at 0.25 log lower than the maximal antinociceptive dose (producing 60-80% MPE), and 0.25 log higher than the maximal antinociceptive dose. Antinociception after a 20 min respiratory test was scored as duration of analgesia, defined as time that MPE was greater than 50%. Bolus injections were used except for the rotorod (i.v.) and tolerance (i.t.) tests, where cumulative dosing was used (44) with minor modifications. Doses were increased in 0.25 log increments with injections every 20 min, followed 15 minutes later by TF and rotorod tests, or a TF test alone in the tolerance experiment.

Blood-Brain Barrier Penetration:

Intracerebroventricular (icy) administration of the opioid antagonist naloxone-methiodide (Nlx-M) was used to test the central effects of peripherally injected analogs. Rats were placed in a stereotaxic apparatus under isoflurane/oxygen anesthetic (4-5% induction, and 1.5-2.5% for maintenance). Infusions of Nlx-M (10 μg/5 μL, icy) or vehicle (5 μL, icy) were made to the right lateral ventricle (1.5 mm lateral, 0.7 mm posterior, and 3.5 mm ventral to the bregma) using a 5 μL syringe. The 10 μg icy dose of Nlx-M was chosen based on reports (24,33) showing the effectiveness of this icy dose in antagonizing systemic morphine. Injection was made over 1 min and the syringe was held in place for 1 additional min to ensure adequate diffusion. About 20 min after the icy injection, the analogs were injected (i.v.) and TF latencies were measured 15, 30, 45, 60, 90, 120, 180, 240, 300, and 360 mins after injection.

Respiratory depression was measured in unanesthetized free-moving rats in a whole body plethysmography system (Buxco, Wilmington, N.C.) as previously described (29). Rats were given saline (1 mL/kg) through an i.v. jugular PE-50 catheter connected via swivel spring leash to a syringe outside the chamber. Minute ventilation (MV, tidal volume×respiratory rate) was determined for 20 min (vehicle baseline), then morphine or an EM analog was injected. Change in MV (% vehicle baseline) was determined over 20 min, the period of maximal effect. A TF test was then conducted at 20 min intervals until antinociceptive scores fell below 50% MPE, defined as the duration of antinociception. Duration of antinociception, an index of total antinociception, was used to assess antinociception relative to respiratory depression for morphine and analogs.

Motor coordination was tested on a ROTOMEX-5 rotorod apparatus (Columbus Instruments, Columbus, Ohio). Cumulative doses were given as described in the antinociception section to produce >90% MPE on the TF test. Only rats remaining on the rotorod for 180 seconds during training were tested, allowing determination of % Maximum Possible Inhibition (% MPI) of motor coordination as [100−(latency to fall/180×100)]. Antinociceptive $ED_{50}$ values were calculated by nonlinear regression. An index of motor impairment relative to antinociception was calculated from the area under the curve (AUC) for MPI/AUC for MPE.

Tolerance was assessed by determining $ED_{50}$s before and after i.t. drug infusions for 7 days. Cumulative dosing with quarter-log increases every 20 min were followed by a tail-flick test 15 min after injection. Immediately after the test in naïve rats, osmotic minipumps (ALZET model 2001, Durect Corp, Cupertino, Calif.) filled with vehicle, morphine, or analog and primed in 0.9% saline at 37° C. for 16 h, were implanted s.c. and connected to a PE-8 (0.008 inch I.D.) i.t. catheter. The pumps delivered 8× the $ED_{50}$/hr (2 μg/hr for morphine, 0.056 μg-0.075 μg/hr for analog) for 7 days (53). A second dose-response curve was generated on day 7. $ED_{50}$ values are presented along with the shift in $ED_{50}$ that provides an index of relative tolerance.

Hyperalgesia relative to morphine was determined at baseline and on day 7 with separate TF scores in which the heat intensity was set to evoke a baseline response >10 sec (cutoff 20 sec) to detect decreased latencies (increased sensitivity).

Immunohistochemistry: Animals from the tolerance experiment were deeply anesthetized with ketamine/xylazine (85/10 mg/kg) and perfused transcardially with 0.1M PBS followed by 4% paraformaldehyde. Spinal cords were post-fixed overnight at 4° C., cryoprotected in 30% sucrose/0.1 M PBS for 48 hr, and sectioned on a freezing microtome at 40 μm. After 2 washes in PBS and blocking with 5% normal goat serum/0.3% Triton X-100, sections were incubated in primary antibody; GFAP (1:1000, ab7779, Abcam, Cambridge, Mass.), Iba1 (1:1000, #019-19741, Wako, Richmond, Va.), pp38 (1:100, #4511, Cell Signaling Technology, Danvers, Mass.), OX-42 (1:100, #CBL1512, Millipore, Temecula, Calif.), or CGRP (1:1000, T-4032, Peninsula Labs, San Carlos, Calif.) for 24 h at 4° C. on a slow rocker. The tissue was then washed twice, re-blocked, incubated in donkey anti-rabbit secondary antibody conjugated to ALEXA 488 dye (1:500 for GFAP, Iba1, CGRP, and 1:200 for pp38, #A21206 Invitrogen, Eugene, Oreg.) or ALEXA 594 dye (1:500, #A21203, Invitrogen) for 2 hours (hrs) at room temperature (RT), washed, and slide-mounted with PROLONG GOLD antifade reagent (Life Technologies, Grand Island, N.Y.). GFAP- and Iba1-immunoreactivities in lamina I-V of dorsal horn segments L4-L5 were quantified on a NIKON microscope with a HAMMAMATSU camera and NIH IMAGEJ software. Images containing lamina I-II of the spinal dorsal horn were analyzed for CGRP and OX-42 integrated density using IMAGEJ software (50). A blinded observer determined integrated density by thresholding the images using the default IMAGEJ algorithm to reduce background and include positively stained cells. Integrated density in the Region of Interest (ROI) is equal to the product of area and mean gray value. The mean gray value represents the sum of the intensity values/number of pixels for all pixels above the threshold in the ROI. This method controls for differences in background between slices and subjects. For quantification of pp38, an observer blinded to treatment manually counted punctate immunoreactive cells. For co-labeling experiments, primary antibody against P2X7 receptors (P2X7R; 1:100, #APR-008, Alamone Labs, Jerusalem, Israel) was incubated with OX-42 overnight. Tissue was washed and re-blocked as described above, and finally incubated with appropriate secondary antibodies ALEXA 488 dye (1:500) and ALEXA 594 dye (1:500) before washing and mounting. Quantification of P2X7R and OX-42 co-labeling was performed using NIKON projection images constructed from 1 μm thick image stacks from lamina I-II. The number of OX-42 positive cells and P2X7R/OX-42 co-labeled cells were counted to determine percent co-labeling (27). A total of 5-6 rats per group and 4-6 slices/rat were quantified for all experiments. Representative confocal images were generated on a LEICA SP2 AOBS microscope.

Conditioned Place Preference (CPP):

Animals were allowed to freely explore an apparatus with a smaller "start box" and two larger distinct compartments (gray vs. black and white stripes of equal luminance; TSE Systems, Chesterfield, Mo.). Mean time in each compartment for 2 morning and 2 afternoon sessions of 20 min each was determined as baseline. For the next three days, the animals were given an i.v. injection of drug and immediately confined to one compartment for 30 min, and vehicle was given in the other. The time at which the drug or vehicle was given (a.m. or p.m.) was counterbalanced, as was the compartment in which the drug was given (preferred or non-preferred, as determined during the baseline test). The unbiased apparatus and design allows for detection of both drug preference and aversion. After three days of conditioning, the animals were allowed free access to all compartments in the drug-free state for 20 min in the morning and afternoon. The mean change in time spent in the drug-paired compartment was determined, and a significant increase on the post-conditioning test relative to that on the pre-conditioning test was interpreted as a CPP, reflective of rewarding properties and potential abuse liability. Equi-antinociceptive asymptotic doses of morphine and analogs producing ≥95% MPE were used in the CPP test. Doses of morphine and Analog 4 were also tested at 0.25 log lower (producing 60-80% MPE), and 0.25 log higher than the maximal antinociceptive dose.

Self-administration (SA) tests were conducted in SA chambers (MED Associates, St. Albans, Vt.) containing an inactive lever and an active lever that regulated a computer-controlled infusion pump outside each chamber. Infusions delivered through TYGON tubing in a balanced arm swivel and metal spring leash allowed the animal free movement and protected the infusion line. The protocol involved 7 sessions of 12-hour access to saline or drug during the dark cycle (55). At the start of each 12-hour session, all rats received one priming injection equivalent to the same dose available during the session. The initial requirement of 1 active lever press per infusion (fixed ratio 1, FR1) was escalated on days 3, 5 and 7 to FR2, 3 and 5, respectively. When the FR requirement was completed, an infusion occurred along with a 10 sec time out period when the stimulus lamp turned off and no additional infusions were possible. Pressings on the active lever that resulted in an infusion or occurred during the 10-sec time out period were analyzed and compared to inactive lever responding. Active lever pressings/12 h, number of infusions/12 h, and intake (mg/kg/12 h) were analyzed from data averaged from the FR3-5 sessions to compare SA at high FR workload requirements to obtain infusion. In 12-hour variable dose studies, SA sessions were conducted for 12 hours per day using a descending dose paradigm in which 0.75, 0.3, 0.1, and 0 mg/kg/infusion of morphine or analogs were available on days 1-2, 3-4, 5-7, and 8-10, respectively.

Alleviation of chronic pain by the analogs was tested in the spared nerve injury (SNI) model. At the site of the trifurcation of the left sciatic nerve, the common peroneal and tibial branches were tightly ligated and transected, leaving the sural branch intact. Pain sensitivity was assessed by applying pressure to the lateral edge of the hindpaw with a Randall-Selitto device. A baseline measure was taken before surgery and at 7 to 10 days postsurgery. Drugs were then administered intrathecally in cumulative doses chosen to produce full alleviation of the hyperalgesia. Duration of pain alleviation (>vehicle) was assessed at 20 min intervals.

Data Analysis:

Data were analyzed by analysis of variance (ANOVA) followed, when appropriate, by Bonferroni, Newman-Kuels, or Dunnett post-tests using GRAPHPAD PRISM software (GraphPad, San Diego, Calif.). Cumulative antinociceptive data from the tolerance study was analyzed by non-linear regression to generate $ED_{50}$ values. Drug tolerance $ED_{50}$ values were determined after acute and chronic administration. Immunohistochemical analysis of cell counts, integrated density, or co-labeling was conducted by blinded observers. Drugs were coded during in vivo experiments and tested by blinded observers. All data is presented as the mean±S.E. with 95% confidence limits. Differences were considered statistically significant when $p<0.05$.

Results

EM Analogs Bind Selectively with High Affinity and Efficacy at Mu Opioid Receptors.

Figure 11:
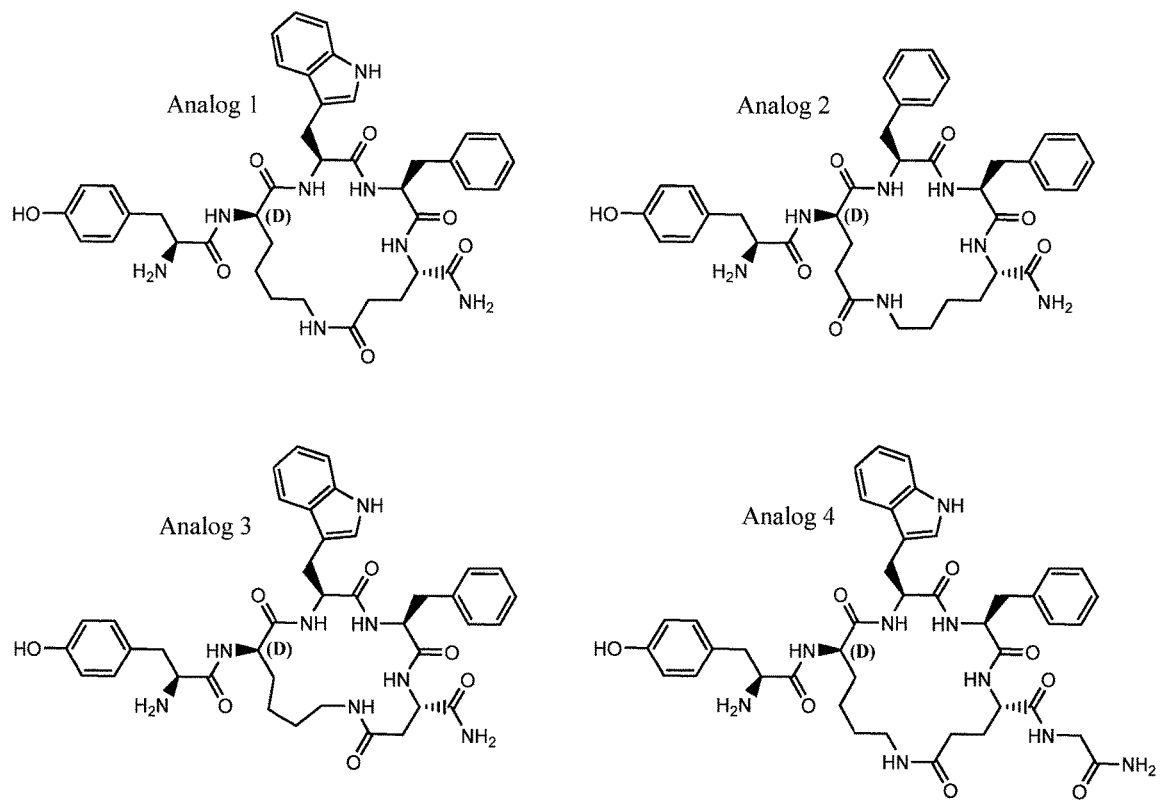
FIG. 11 shows EM analog structures and receptor selectivity. (A) Chemical structures of cyclized, D-amino acid-containing analogs: Tyr-c[D-Lys-Trp-Phe-Glu]-NH$_2$ (SEQ ID NO: 1, ZH850, Analog 1), Tyr-c[D-Glu-Phe-Phe-Lys]-NH$_2$ (SEQ ID NO: 2, ZH831, Analog 2), Tyr-c-[D-Lys-Trp-Phe-Asp]-NH$_2$ (SEQ ID NO: 5, ZH809, Analog 3) and Tyr-c[D-Lys-Trp-Phe-Glu]-Gly-NH$_2$ (SEQ ID NO: 3, ZH853, Analog 4). (B) In vitro opioid receptor selectivity of binding and activation by analogs and reference compounds morphine, DAMGO and EMs to cloned human mu, delta and kappa opioid receptors. Values represent means of 2-4 independent assays in duplicate. (C) In vivo selectivity illustrated by antagonism of analog-induced antinociception by naloxone, but not by delta (NTI) or kappa (nBNI) antagonists. AUC was calculated from antinociceptive % MPE scores. To provide similar AUC values, Analogs 1 and 2 were given at 3.2 mg/kg while Analogs 3 and 4 were given at 5.6 and 1.8 mg/kg respectively. Differences among treatments ($F_{3,18}=8.30$, $F_{3,17}=9.34$, $F_{3,16}=17.33$, $F_{3,20}=18.93$, $p<0.001$ for Analogs 1-4, respectively) were attributable to a highly significant reduction of antinociception by naloxone (***$p<0.001$), while NTI and nBNI treatment did not affect antinociceptive scores (n=5-7).
Figure 11:
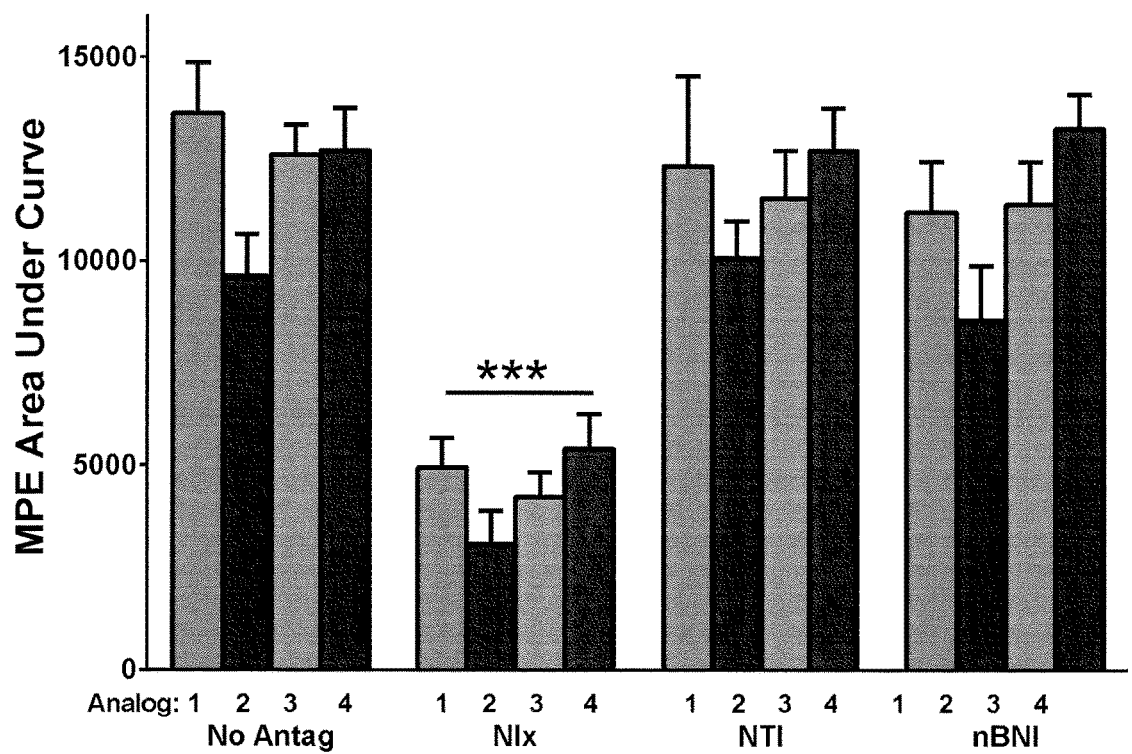

Analog structures are shown in FIG. 11, Panel A. Binding assays with cloned human opioid receptors showed that all four analogs had selectivity and subnanomolar affinity for MOR (FIG. 11, Panel B). Analog 4 showed the highest selectivity. In $^{35}$S-GTPγS assays the analogs showed full agonism at MOR, had greater potency than morphine, DAMGO and EMs, and remarkable selectivity for MOR activation (>100000 and >3000-fold higher concentrations were required for delta or kappa activation). Interestingly, Analogs 1, 3 and 4 showed high efficacy delta antagonism at sub-micromolar concentrations. In vivo selectivity was also demonstrated: FIG. 11, Panel C shows that antinociceptive effects of all four analogs were significantly blocked by naloxone (1 mg/kg), but not by antagonists for DOR (NTI) or KOR (nor-BNI) at doses (1 mg/kg) known to antagonize selective agonists for those receptors after i.v. injection in the rat (26,30).

EM Analogs Show High Solubility and Stability.

Figure 12:
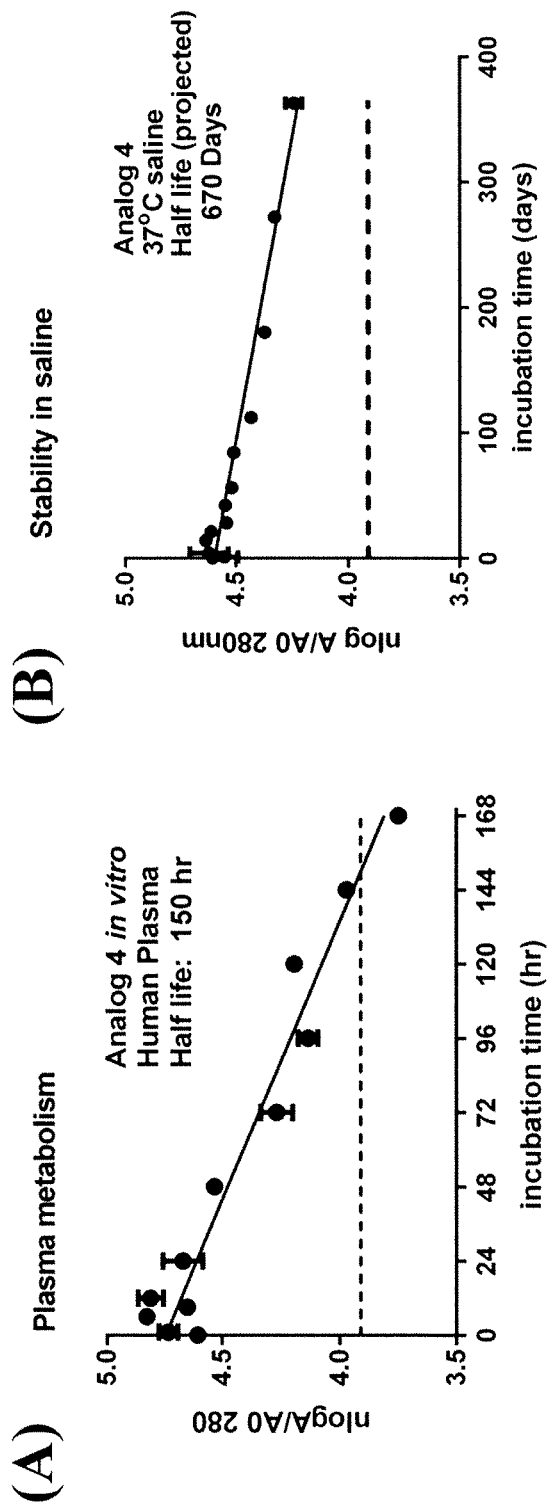
FIG. 12 demonstrates Analog 4 stability and antinociceptive effectiveness after peripheral administration. (A, B): Analog 4 was incubated at 37° C. in human (A) or rat (not shown) plasma or physiological saline (B) and stability was analyzed at various time points by HPLC. Means±SEM of duplicate samples at each point are plotted. Dashed lines represent the 50% degradation point. Linear regressions were significant for plasma and saline ($F_{1,32}=216$, $F_{1,26}=242$, $p<0.0001$) with $R^2$ of 0.87 and 0.86, respectively. (C-E): Dose-dependent TF antinociception after i.v., s.c., and oral administration of Analog 4. Two-way ANOVA showed a significant effect of dose ($F_{3,276}=252.4$, $F_{4,310}=76.00$, $F_{3,182}=117.00$) time ($F_{12,276}=17.7$, $F_{10,310}=20.4$, $F_{10,182}=26.5$) and interaction ($F_{36,276}=4.3$, $F_{40,310}=4.1$, $F_{30,182}=4.8$), all $p<0.0001$ for i.v., s.c., and oral, respectively. (D) The MOR antagonist β-FNA blocked the effects of Analog 4 (3.2 mg/kg, s.c. [$F_{2,192}=53.51$, $p<0.0001$]). Time points at which Analog 4 produced significant differences from vehicle are shown at the top of each graph (, *, ****=$p<0.01$, 0.001, 0.0001 for highest dose vs vehicle; +, ++, +++, ++++=$p<0.01$, 0.001, 0.0001 for middle dose vs vehicle, #=$p<0.05$ for lowest dose vs. vehicle. n=5-11).
Figure 12:
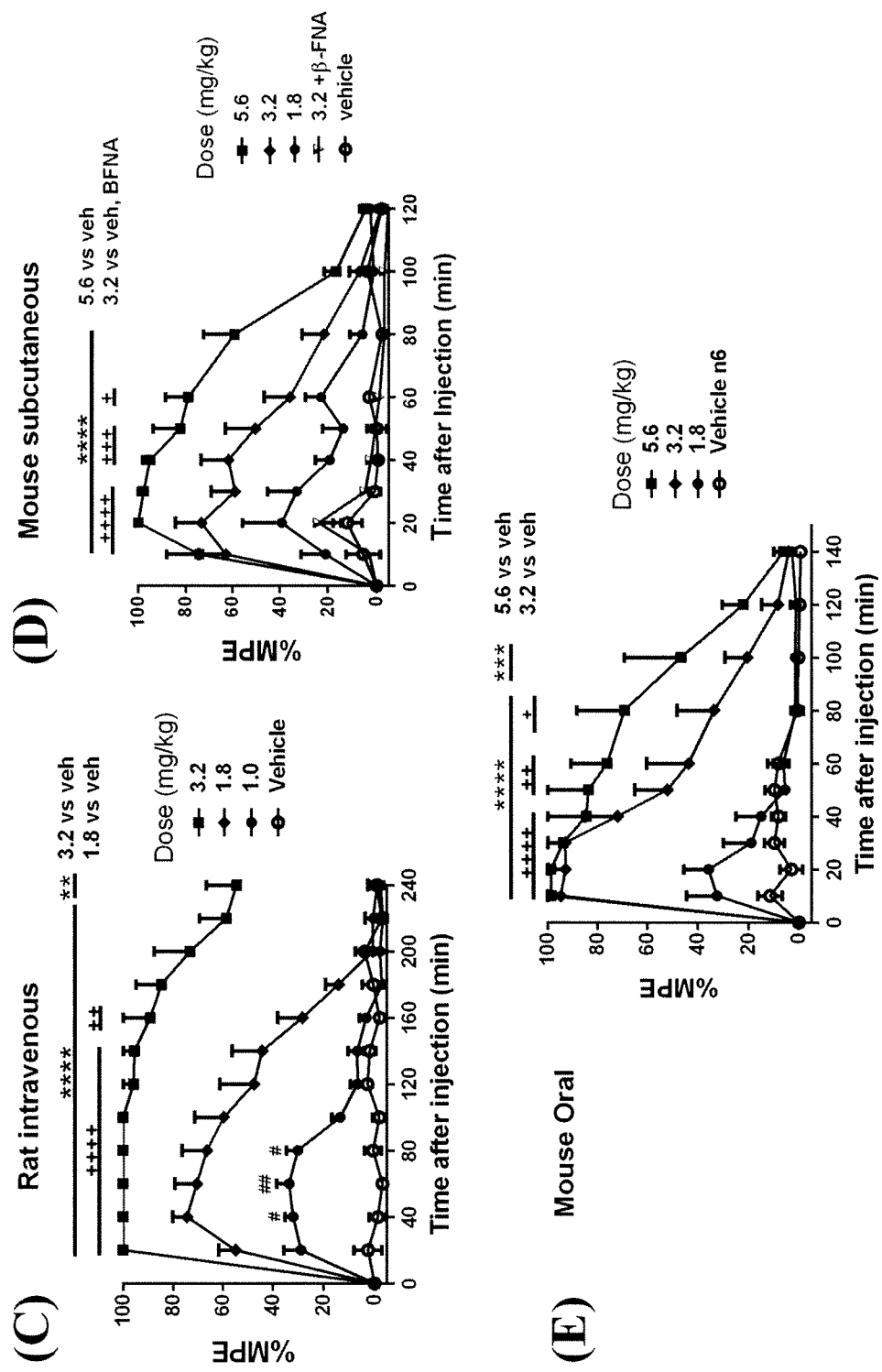

The EM analogs showed favorable solubility (40, 20, 20 and 50 mg/mL in water, 15, 15, 12, and 20 mg/mL in saline, and 90, 70, 50, and 50 mg/mL in 20% PEG400/saline for Analogs 1-4, respectively), and stable plasma half-life in vitro. While the parent endomorphins were metabolized rapidly in rat plasma with a half-life of 5 min, Analogs 1-4 showed half-lives of 14, 46, 14, and 81 hr. The longer value for Analog 4 relative to Analog 1 indicates that the glycine extension surprisingly enhances stability. Analog 4 also was tested in human plasma and showed a half-life of about 150 hours (FIG. 12, Panel A). Stability in saline at 37° C. was >1 year (FIG. 12. Panel B), indicating a highly favorable "shelf life" and usefulness for long-term infusion.

EM Analogs Produce Potent, Long Lasting and Mu-Selective Antinociception after Peripheral Administration.

Figure 13:
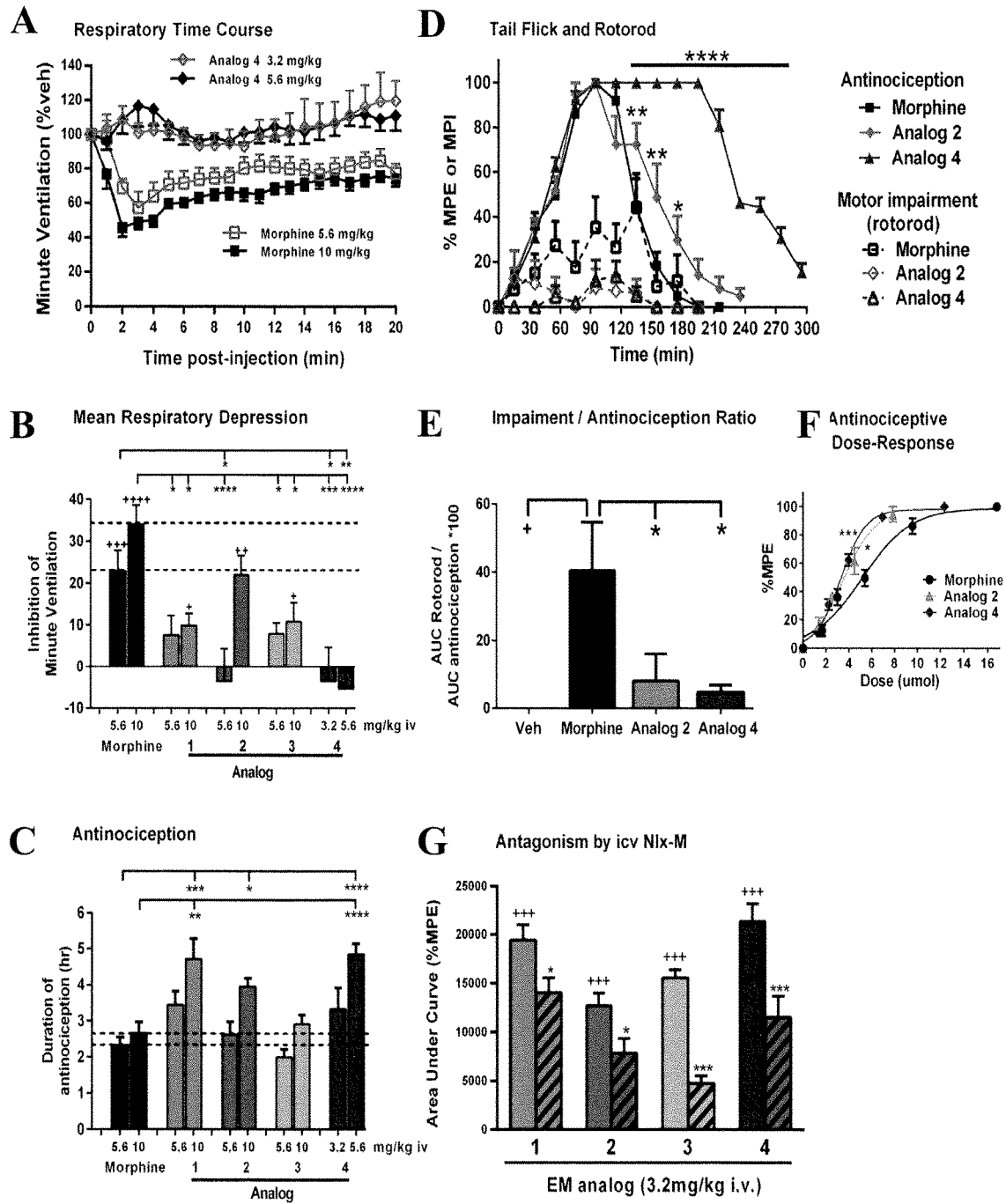
FIG. 13 illustrates reduced impairment of respiration and motor coordination with BBB penetration. (A) Time course of change in minute ventilation (MV) after morphine (5.6, 10 mg/kg i.v.) or EM Analog 4 at doses (3.2, 5.6 mg/kg i.v) producing greater duration of antinociception. (B) Mean % inhibition over 20 min showed significant differences after various drug doses ($F_{9,58}=6.19$, $p<0.0001$). (C) Duration of antinociception varied among drug groups ($F_{9,65}=8.70$, $p<0.001$) with Analog 4 producing almost twice the duration of morphine. Dashed lines illustrate the range of morphine responses for reference. (D) For motor coordination, morphine (squares), Analog 2 (diamonds) or Analog 4 (triangles) were administered in cumulative doses increasing every 20 min followed 15 min later by TF and rotorod tests. % MPE values for antinociception (TF, filled symbols) and % maximum possible inhibition (% MPI) values for rotorod inhibition (open symbols) were determined. Differences in antinociception ($F_{3,327}=348.9$, $F_{15,327}=93.51$, $p<0.0001$, for drug and time, respectively) reflected significantly longer and greater total antinociception for Analogs 2 and 4 relative to morphine, and differences in motor impairment ($F_{3,231}=15.19$, $F_{10,231}=2.34$, $p<0.0001$, 0.05, for drug and time, respectively) reflected less total impairment. (E) Significantly different motor impairment AUC/antinociceptive AUC ratios ($F_{3,21}=4.43$, $p<0.05$) were found and (F) dose-response curves showed that, on a molar basis, Analogs 2 and 4 were significantly more potent than morphine ($ED_{50}=3.5\pm0.39$, $3.3\pm0.13$, and $5.2\pm0.41$ μmol for Analog 2, Analog 4, and morphine respectively). (G) Antinociception after peripheral administration of the analogs was reduced by central administration of the opioid antagonist Nlx-M ($F_{11,43}=23.01$, $p<0.0001$) suggesting blood-brain-barrier penetration. TF data were converted to area under the curve (AUC). +, ++, +++, ++++$p<0.05$, 0.01, 0.001, 0.0001 relative to vehicle; *, , *, ****$p<0.05$, 0.01, 0.001, 0.0001 relative to morphine, n=5-8.

The stability of the analogs translated to effectiveness after peripheral administration as shown by potent and long lasting antinociception after intravenous (i.v.), subcutaneous (s.c.), and oral administration. FIG. 12, Panels C-E illustrate these results for Analog 4. At doses producing maximal % MPE, the durations of antinociception for i.v. (FIG. 12, Panel C) s.c., (FIG. 12, Panel D) and oral (FIG. 12, Panel E) administration were 240, 80, and 100 min, respectively. The duration of antinociception after i.v. injection in rat for morphine and all analogs is shown in FIG. 13, Panel C. FIG. 12, Panel D shows that the mu-selective antagonist β-FNA eliminated antinociception induced by s.c. administration of Analog 4 in mouse, consistent with the MOR-selective receptor binding data.

Respiratory Depression is Reduced or Absent after EM Analogs at Doses Producing Equal or Greater Duration of Antinociception Relative to Morphine.

Changes in MV over the 20 minute period of maximal drug effect are illustrated for morphine and Analog 4 in FIG. 13, Panel A, and average changes for all compounds in FIG. 13, Panel B. Duration of antinociception determined from TF tests conducted at 20 min intervals thereafter are shown in FIG. 13, Panel C. Morphine produced significant inhibition of MV at 5.6 and 10 mg/kg (FIG. 13, Panel A,B) along with about 2-3 hr of antinociception (FIG. 13, Panel C). By contrast, after EM analogs, respiratory inhibition was below, and duration of antinociception (2-6 h) was at or above, that produced by morphine (dashed lines). The rank order for duration of antinociception was Analog 4>1>3>2>morphine. Analog 4 showed the clearest separation with no respiratory depression in the presence of significantly longer antinociception induced by lower doses. The results indicate that the EM analogs are clearly more effective and safer analgesics than morphine.

Motor Coordination is Impaired by Morphine but not EM Analogs.

Impairment of motor coordination relative to antinociception was tested in rotorod and TF tests. Analogs 2 and 4 produced significantly longer and greater total antinociception than morphine (FIG. 13, Panel D), were significantly more potent (FIG. 13, Panel F), and did not produce significant motor impairment (FIG. 13, Panel D,E). Morphine showed significantly more impairment than vehicle and the analogs (FIG. 13, Panel D,E). Analog 4 provided the greatest duration of antinociception and the least motor impairment. Vehicle animals remained on the rotorod for the 3 min maximum (no inhibition) and vehicle TF values (not shown for clarity) were below 10% MPE at all time-points, indicating that the testing sequence did not produce stress- or rotorod-induced antinociception. Differences in motor impairment ratio (FIG. 13, Panel E) were significant with morphine (40.6±14.2) scores significantly greater than those of vehicle (0.0), Analog 2 (8.0±8.0) and Analog 4 (4.7±2.0), indicating a 5-fold and 8.6-fold better therapeutic ratio for Analogs 2 and 4 relative to morphine.

Cognitive Function is Impaired by Morphine, but not Analog 4.

Tests of cognitive function (spatial memory) in the Morris Water Maze (MWM) revealed that Analog 4 shows a highly favorable profile relative to morphine. After 4 days of training, an injection of morphine produced impairment of spatial memory, as reflected by a significant increase in the latency to, and average distance from, the platform. By contrast, Analog 4 did not produce significant impairment, even at doses that provided 2-3 times greater duration of antinociception than morphine. These results indicate an unexpected and superior therapeutic profile of the peptides of Formula I with regard to cognitive function relative to the current standard opioid analgesic.

EM Analogs Access and Activate CNS Receptors.

FIG. 13, Panel G shows that i.c.v. low-dose (10 μg) injection of the blood-brain barrier impermeable antagonist naloxone methiodide (Nlx-M) significantly inhibited i.v.

analog-induced antinociception (p<0.05). These results indicate that full antinociceptive effects require activation of CNS opioid receptors and that the relative lack of respiratory and motor impairment by the analogs is not due to lack of CNS entry.

EM Analogs Produce Less Tolerance and Hyperalgesia than Morphine.

Figure 14:
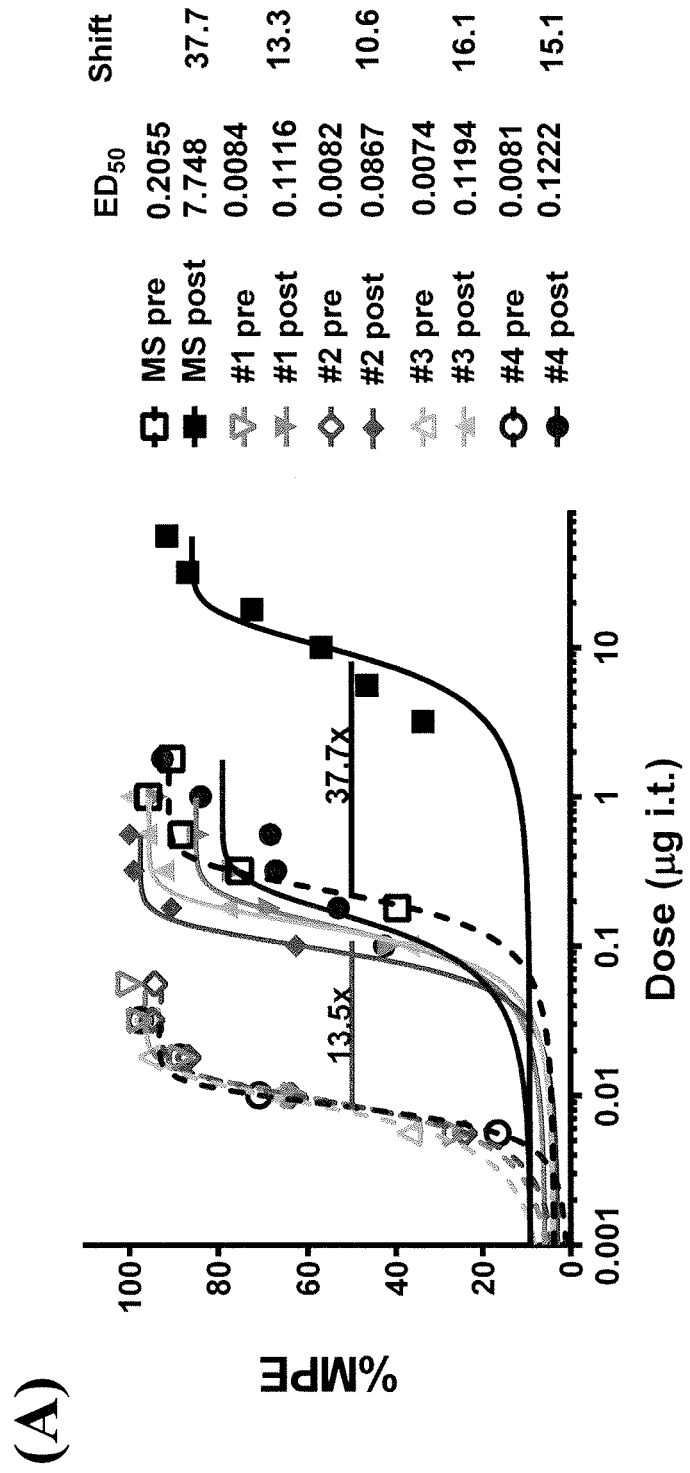
FIG. 14 illustrates reduced tolerance, glial and CGRP activation after EM analogs relative to morphine. (A) Tail-flick dose-response curves were determined before (pre, open symbols) and after (post, closed symbols) 7 days of intrathecal (i.t.) drug delivery, and shifts in $ED_{50}$ were determined as an index of relative tolerance. The acute potencies of the analogs were 30-fold greater than that of morphine before chronic infusions. The $ED_{50}$ of morphine shifted 37.7-fold while those of the analogs shifted on average 13.5-fold reflecting significantly less tolerance ($F_{1,114}=135$, $p<0.0001$). (B) Photomicrographs of representative samples of dorsal horn immunostaining for the astrocytic marker GFAP, the microglial marker Iba1, and the MAPK signaling kinase associated with microglial activation pp38 [20x; insets: 63× (GFAP, Iba1) and 40× (pp38), Scale bar=100 μm]. (C) Significant differences in immunostaining were observed for all three markers ($F_{5,25}=3.61$, $p<0.05$, $F_{5,24}=4.71$, $p<0.01$, $F_{5,25}=16.83$, $p<0.0001$ for GFAP, Iba1 and pp38, respectively). All three were activated by morphine, but none were activated by the analogs. Values for all analogs were significantly below those of morphine for Iba1 and pp38. (D) Representative photomicrographs (Scale bar=50 μm) of CGRP expression. (E) Quantification showing increased CGRP immunostaining after chronic morphine, but not analogs ($F_{5,24}=4.50$, $p<0.01$). CGRP levels after the analogs were significantly reduced compared to morphine. (F,G) Upregulation of P2X7 receptors in microglial cells. (F) Representative photomicrographs (Scale bar=20 μm); and (G) quantification showing chronic morphine upregulated P2X7 receptors ($t_7=2.50$, $p<0.05$), OX-42-labeled microglial cells ($F_{2,16}=3.96$, $p<0.05$), and especially microglial cells containing P2X7 receptors (merge) ($F_{2,12}=15.61$, $p<0.001$). By contrast, Analog 4 did not alter OX-42 levels or microglial co-labeling with P2X7 receptors. +, ++, ++++=$p<0.05$, 0.01, 0.0001 significantly different from vehicle; *, , *=$p<0.05$, 0.01, 0.001, compared to morphine. Tolerance: n=6-12; IHC: n=5-6 rats, 4-6 sections per rat.
Figure 14:
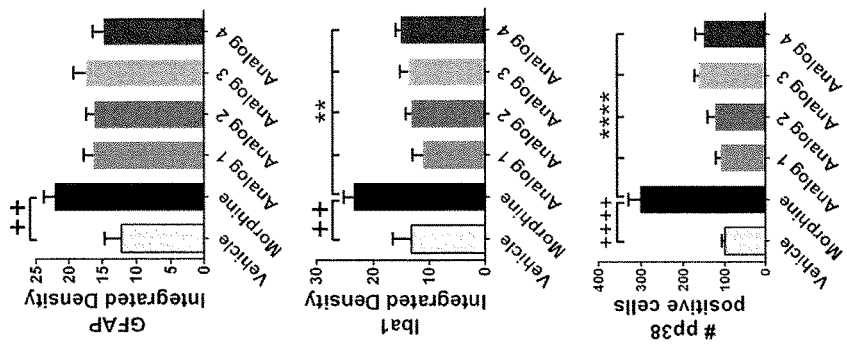
Figure 14:
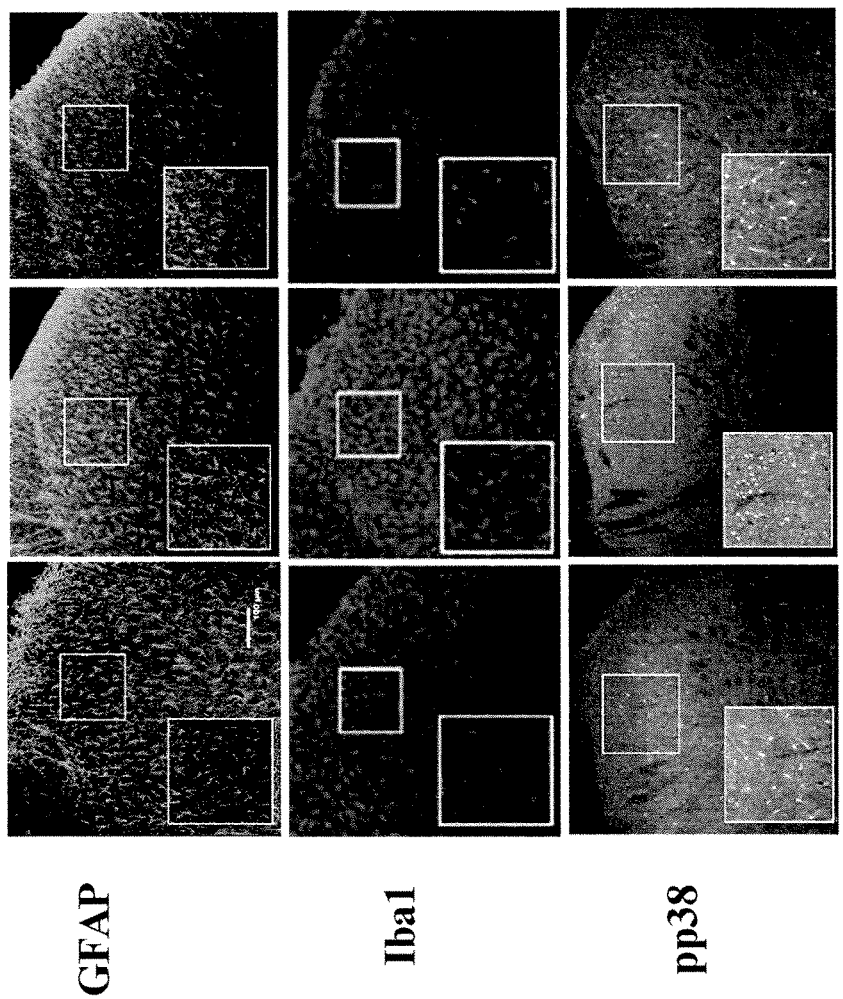
Figure 14:
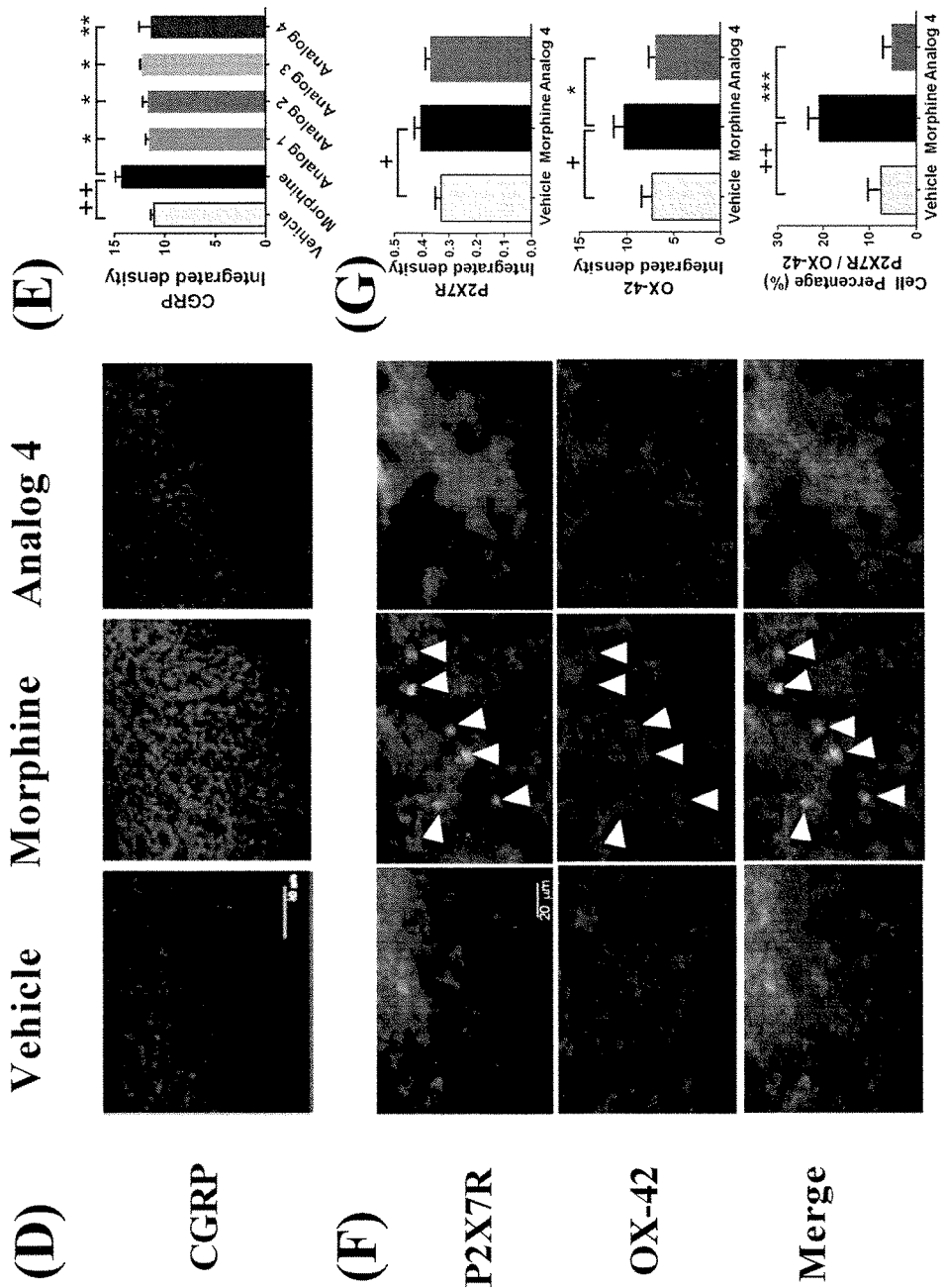
Figure 15:
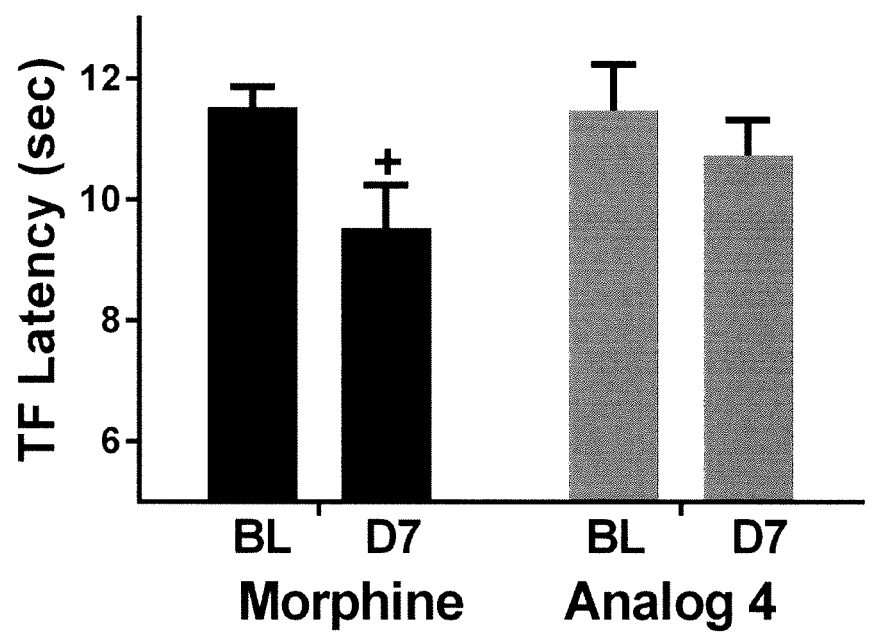
FIG. 15 demonstrates that chronic morphine, but not Analog 4, induces thermal hyperalgesia. Tail flick latencies were measured on day 1 (baseline, BL) and after 7 day infusion (D7) of morphine or Analog 4. Heat settings for baseline latencies were set to 10 sec to allow assessment of increased thermal sensitivity with a cutoff of 20 sec. Latencies were significantly reduced after 7 day infusion of morphine, but not Analog 4. [+=$p<0.05$ relative to BL, n=12 (morphine), 8 (Analog 4)].

Tolerance and glial activation were tested in a well-characterized model (53,19). Cumulative intrathecal (i.t.) dosing of naïve rats showed that EM analogs were initially 30-fold (60-fold on a molar basis) more potent than morphine (FIG. 14, Panel A). After 7 days of infusion, the $ED_{50}$ of morphine shifted 38-fold. By contrast, EM analogs, tested at doses matched for antinociception, surprisingly produced a shift of only 14-fold, demonstrating substantially less tolerance. Analog 4 was selected for comparison to morphine for hyperalgesia. FIG. 15 shows that 7-day treatment with morphine, but not EM Analog 4, induced hyperalgesia.

Activation of Glial Cells by Morphine, but not EM Analogs.

Glial activation was assessed using markers for astrocytes (GFAP), microglia (Iba-1 and OX-42), and the activated microglial MAP kinase phospho-p38 (pp38) (FIG. 14, Panels B,C). Expression of all 3 markers was significantly increased after morphine, but not after any of the analogs. Expression of Iba-1 and pp38 after analogs was significantly below that of morphine.

Upregulation of CGRP by Morphine, but not EM Analogs.

CGRP induction has been implicated in glial activation and tolerance (56). FIG. 14, Panels D,E show CGRP staining was strongly upregulated in the dorsal horn of the spinal cord by chronic infusion of morphine, but not by any of the EM analogs.

Upregulation of P2X7 Receptors by Morphine, but not EM Analog 4.

Because upregulation of microglial P2X7R has been implicated in tolerance (27,62) changes in this marker after morphine and Analog 4 administration were tested. Morphine, but not Analog 4, upregulated P2X7 receptors in microglial cells (FIG. 14, Panels F,G). Activated microglia contained high levels of P2X7 receptor expression, confirmed by increased microglial OX-42 that strongly co-labeled with P2X7 receptors. The high proportion of co-localization of upregulated P2X7 and activated microglia after morphine (21% vs 5% after Analog 4 or vehicle) suggests increased ATP-P2X7-neurotrophin-cytokine mediated effects of morphine, but not Analog 4. In summary, EM analogs produced more potent acute antinociception and, after chronic administration at equi-effective doses, induced substantially less tolerance and did not promote glial reactivity, CGRP upregulation or P2X7 induction compared to morphine.

Figure 16:
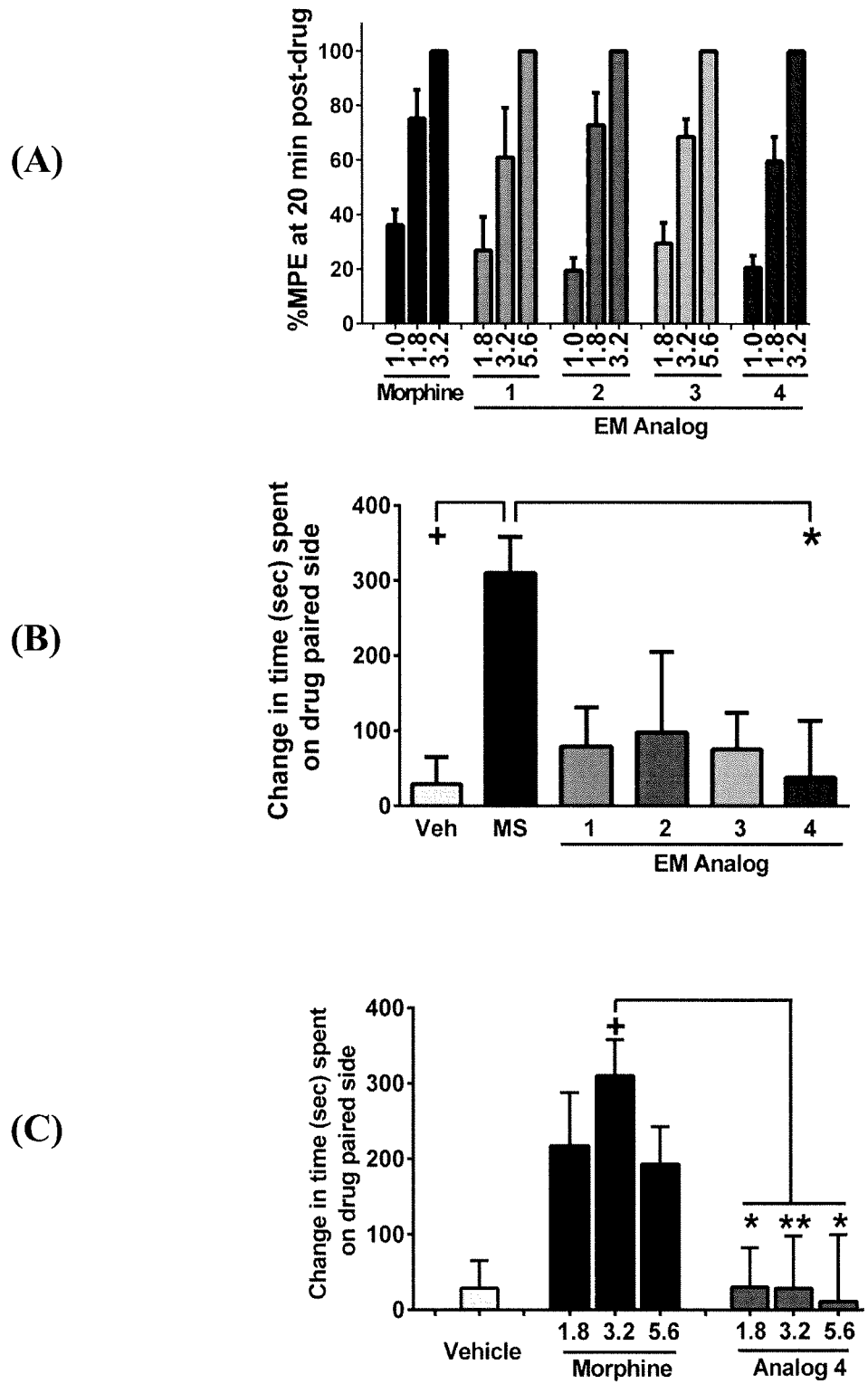
FIG. 16 illustrates tests for abuse liability. (A) Doses of morphine and EM analogs providing equal antinociception 20 min after injection. (B) Conditioned place behavior at equi-antinociceptive doses showed morphine produced a significant increase in time spent in the drug-paired box (CPP), while rats given EM analogs were not significantly different from controls ($F_{5,51}=3.25$, $p<0.05$). (C) CPP for morphine occurred in a classic inverted-U dose-response fashion, whereas analogs did not produce CPP ($F_{6,57}=3.97$, $p<0.01$). (D) Self-administration: Rats elevated lever pressings when required to obtain a sub-antinociceptive dose of morphine ($F_{1,18}=20.33$, $p<0.001$), but not for infusions ("inf") of the analogs, and only Analog 2 showed a small but significant increase on the active "drug lever" vs. inactive lever on the final trial ($F_{5,272}=36.11$, $p<0.0001$). (E) Active (filled bars) and inactive (open bars) lever pressings averaged across sessions 5-7 (FR3-5) from Panel D. Active lever pressings for morphine, but not analogs, were significantly greater than the inactive lever and vehicle ($F_{11,78}$=10.16, p<0.0001). (F) A variable dose experiment showed that as the available dose was lowered, rats worked harder to obtain morphine, but not analog infusions ($F_{4,240}$=32.05, p<0.0001). (G) Lever pressings for antinociceptive doses of morphine were significantly greater than the inactive lever (morphine 1 mg/kg/inf: $F_{1,55}$=18.33, p<0.0001; 3 mg/kg/inf: $F_{1,49}$=21.66, p<0.0001), while these doses of Analog 4 did not produce self-administrations. (H) Number of infusions and intake per 12 h shows that Analog 4 was not self-administered at any dose compared to morphine. (I) Active lever pressings show rats increased workload effort for morphine infusions at a range of doses ($F_6$, 42=5.395, p<0.001) while no escalation was made for Analog 4 ($F_{3,25}$=2.05, p=0.1321). +, ++, +++p<0.05, 0.01, 0.001 relative to vehicle; *, , * p<0.05, 0.01, 0.001 relative to morphine; #, ##p<0.05, 0.01 relative to the inactive lever. n=8 rats/group for CPP; n=5-10 rats/group SA.
Figure 16:
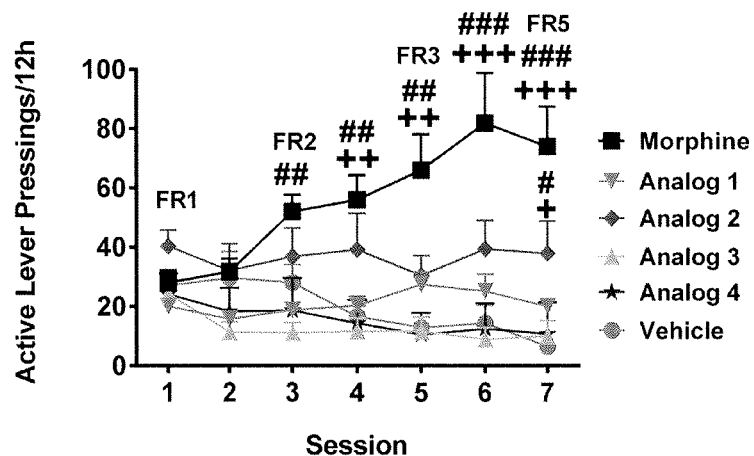
Figure 16:
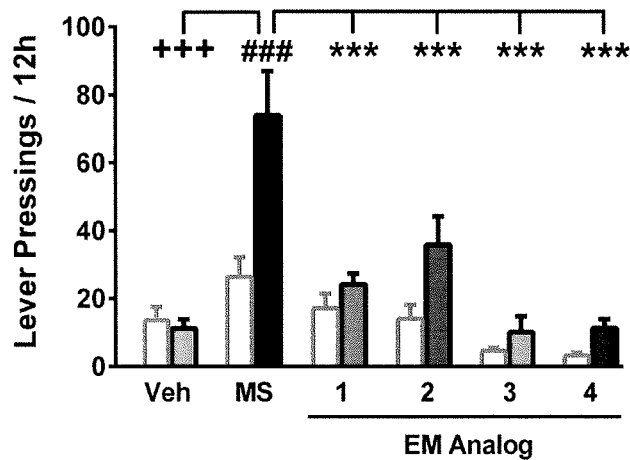
Figure 16:
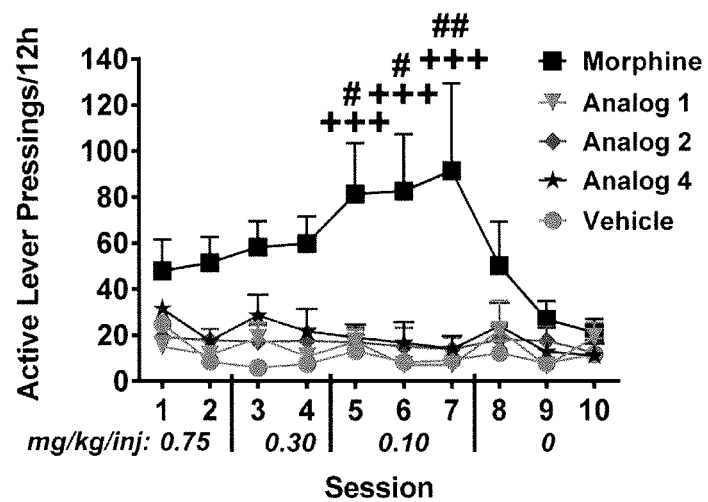
Figure 16:
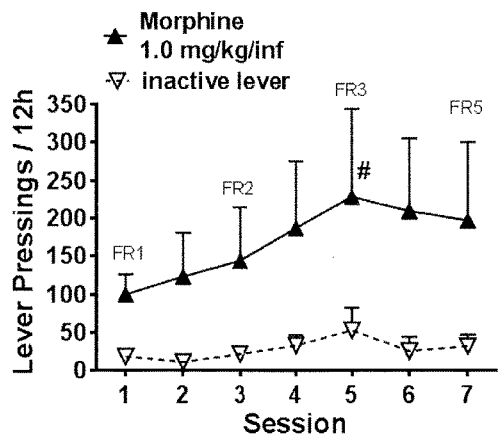
Figure 16:
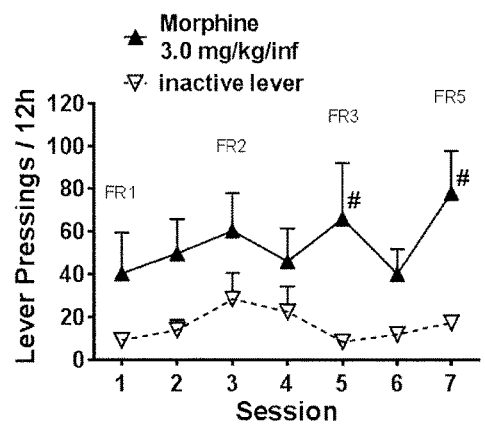
Figure 16:
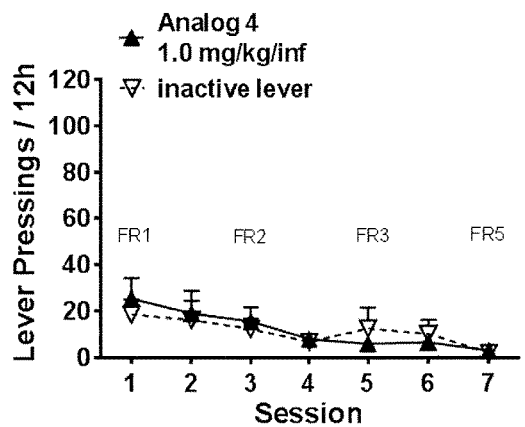
Figure 16:
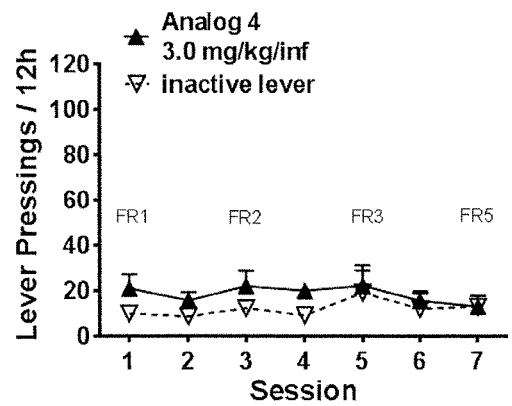
Figure 16:
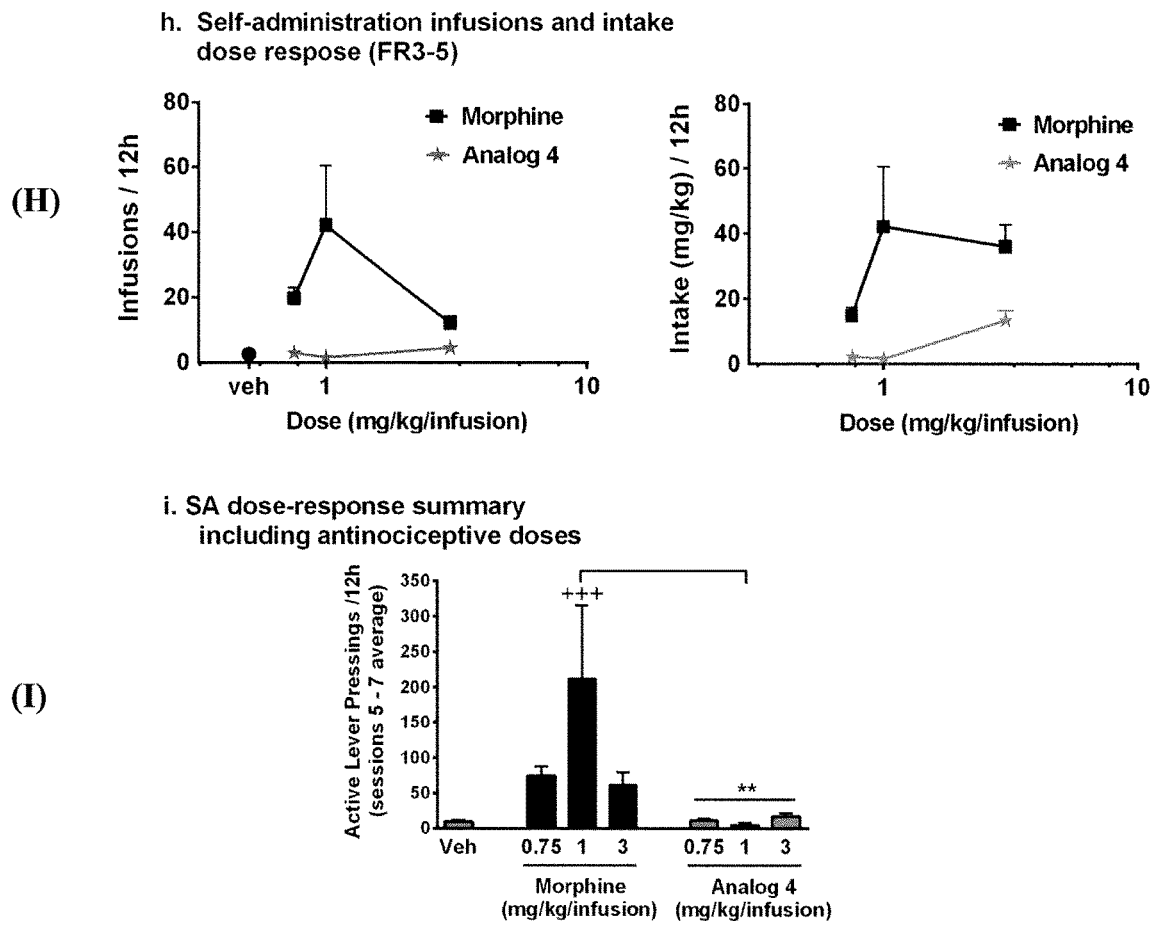

Abuse liability was tested in two complementary paradigms, CPP and SA. CPP was compared using equally asymptotic antinociceptive doses that produced full antinociception (>95% MPE) 20 min after injection (FIG. 16, Panel A), corresponding to the period of confinement to the conditioning side. These doses were determined as 3.2 mg/kg i.v. for morphine, 5.6, 3.2, 5.6, and 3.2 mg/kg for EM Analogs 1, 2, 3, and 4, respectively. FIG. 16, Panels B and C show that after 3 days of conditioning, morphine, but not the analogs, produced a significant increase in the time spent on the drug-paired side, a place preference. None of the compounds showed place aversion (decreased time on the drug-paired side). Morphine and EM Analog 4 were also tested at 0.25 log higher, and 0.25 log lower doses, but only morphine produced CPP. (FIG. 16, Panel C).

While CPP has an advantage of testing for reward associations in the drug-free state, SA more directly models drug consumption. Rats were allowed to bar press for i.v. morphine, EM analogs or vehicle for 12 h/day for 7 days with an escalating fixed ratio schedule. As the effort required to receive the drug increased from 1 to 5 presses per infusion (FIG. 16, Panel D), rats significantly escalated bar pressings for morphine, but not for the analogs (0.75 mg/kg/infusion). FIG. 16, Panel E compares active drug lever presses to an inactive lever during high-effort sessions with FR requirements set at 3-5 (e.g. 3-5 presses required for 1 infusion). Morphine produced significantly higher active lever pressings than vehicle or the inactive lever, while pressings for all analogs were significantly reduced by comparison. As doses were gradually lowered (0.75, 0.3, and 0.1 mg/kg/infusion) across sessions, rats self-administering morphine increased responding, while rats given access to EM analogs did not escalate lever pressings (FIG. 16, Panel F). At comparably antinociceptive infusion doses (FIG. 16, Panels G-I) of morphine and EM Analog 4, the same pattern emerged; pressings for morphine (1 and 3 mg/kg/infusion) were significantly elevated over the inactive lever, whereas none of the doses of EM Analog 4 (1 and 3 mg/kg/infusion) were self-administered (FIG. 16, Panels G-I). Thus, in CPP and SA models, the EM analogs showed significantly reduced reward properties relative to morphine, consistent with low abuse liability.

Support for the concept that Analog 4 could also be useful for treating subjects with a history of abuse was demonstrated in a drug discrimination paradigm. Rats were trained to discriminate morphine injections from vehicle to receive food pellets. When challenged with Analog 4, rats responded on the morphine lever, indicating they could discriminate the EM analog as more similar to morphine than vehicle. In combination with the lack of self-administrations by Analog 4, these data convey a compelling case for a compound that effectively substitutes for morphine, but does not produce reward, indicating strong potential for opioid addiction pharmacotherapy.

EM Analogs Provide Potent and Prolonged Alleviation of Chronic Pain.

Figure 17:
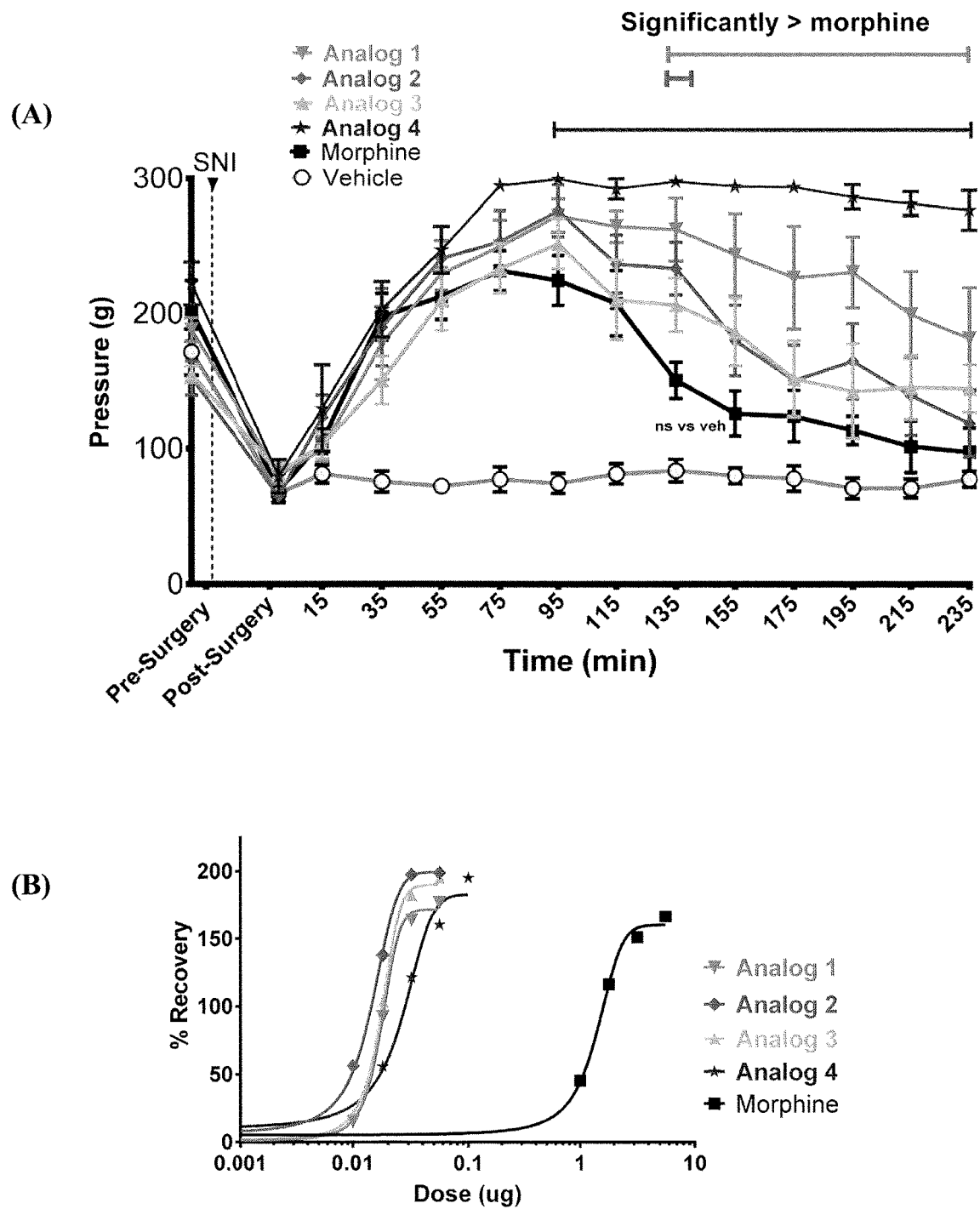
FIG. 17 shows that EM analogs provide potent and prolonged relief of neuropathic pain induced by the spared nerve injury (SNI) model in the rat. As demonstrated in Panel A, prior to SNI surgery ("pre-surgery"), an average pressure of about 182 g applied to the hindpaw with a Randall-Selitto device was required to elicit a paw withdrawal response. At 7 to 10 days post-surgery, the animals showed hyperalgesia, indicated by a reduction in the average pressure (to about 74 g) required to elicit withdrawal. Drugs were administered as intrathecal cumulative doses chosen to produce full alleviation of the hyperalgesia. Pressure tolerance (pain alleviation) was significantly greater than vehicle until 135 min after injection for morphine, and 235 min or more for the analogs (p<0.05-0.0001). In addition, scores for analog 2 were significantly above those of morphine at 135 min, from 135-235 min for Analog 1, and from 95-235 min for Analog 4 (bars above time points, p<0.05-0.0001). 'ns vs veh'=time at which morphine scores were no longer significantly different than vehicle. Dose-response curves (Panel B) showed that all analogs are significantly more potent than morphine, as determined by the dose required to fully (100%) reverse the hyperalgesia, i.e., return to the pre-surgical baseline response (pre-surgical minus post-surgical pressure). While potency differences among the analogs were not significant (p>0.05), the analogs reversed mechanical hypersensitivity at doses about 80-fold lower than morphine (average of 0.02 vs 1.61 μg for morphine, p<0.0001), n=6-11.

As shown in FIG. 17, Panel A, Analogs 1-3, and especially Analog 4, provide unexpectedly potent and long-lasting relief of neuropathic pain induced by the spared nerve injury (SNI) model in the rat. Alleviation of mechanical hypersensitivity (scores significantly greater than those after vehicle) lasted just over 2 hours (about 135 min) after morphine and 4 hours or more (>235 min) after administration of the EM analogs. An increase, relative to morphine, in duration of relief was significant at 135 min for Analog 2, at 100 min for Analog 1 (135-155 min), and at least about 140 min (95-235+ min) for Analog 4. Although potency differences among the analogs were not significant, the analogs were on average 80-fold more potent than morphine (p<0.0001). On a molar basis, this represents an average of 180-fold greater potency. The analogs, especially Analog 4, also produced more potent and longer duration of relief than morphine after other forms of chronic pain including post-incisional (post-operative) and inflammatory pain induced by Complete Freund's Adjuvant (CFA). The foregoing examples are illustrative, but not exhaustive, as to the types of acute or chronic pain for which the peptides of Formula I are effective.

Figure 18:
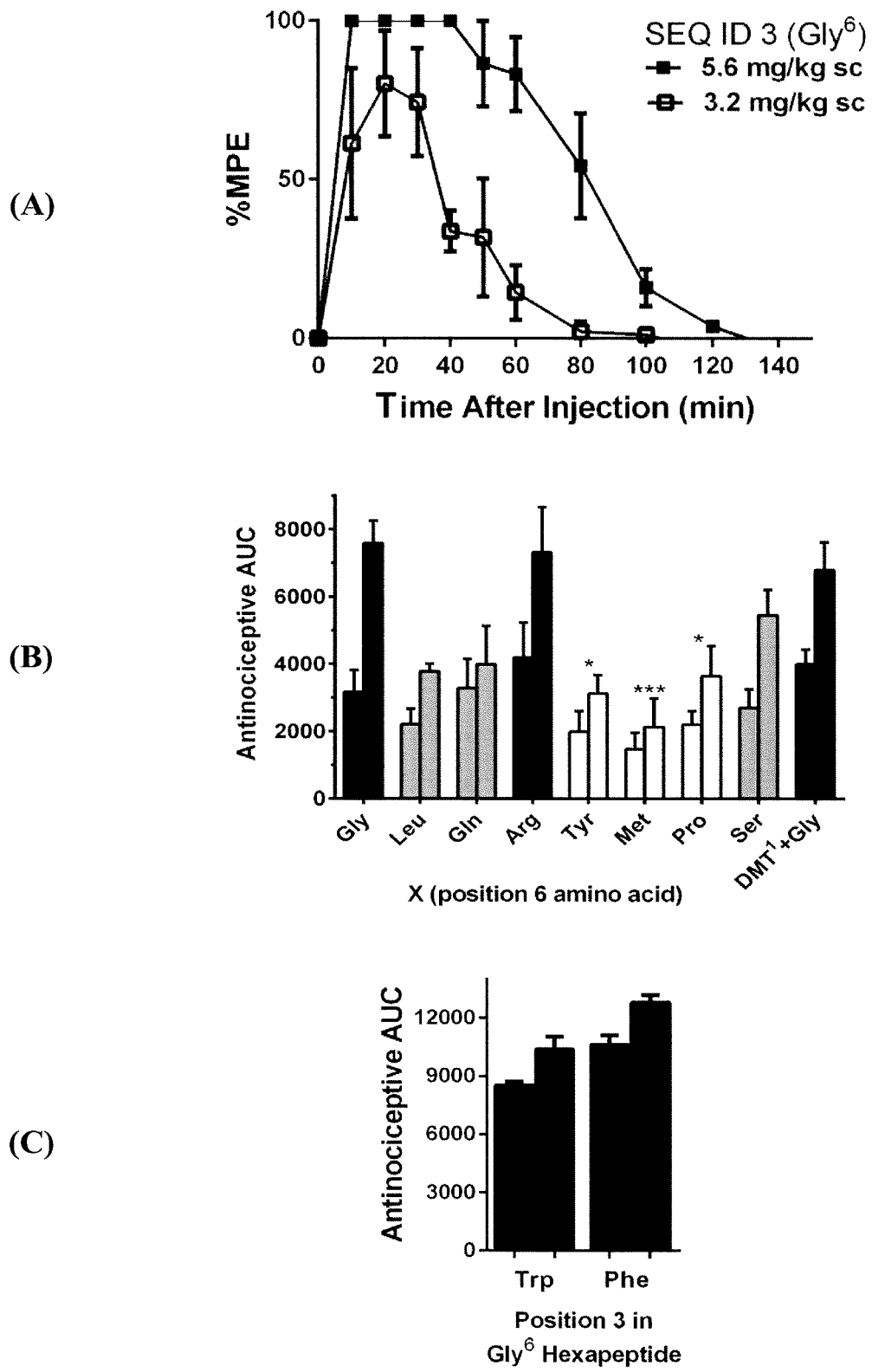
FIG. 18 illustrates the antinociceptive effects of several hexapeptides of the Formula I in which the L-amino acid (AA) in $X_5$ is varied. Antinociception was measured in the tail flick test following subcutaneous injection to mice. All compounds were compared at 3.2 and 5.6 mg/kg; results from 9 peptides with $X_2$=Trp are shown, along with the listed amino acid substituted in position 6 ($X_5$). The Gly-containing peptide (Analog 4, SEQ ID NO: 3) provided potent antinociception after peripheral injection. Panel A shows the time course of antinociception induced by Analog 4, expressed as maximum possible effect (% MPE, as described for FIG. 6). The 5.6 mg/kg dose maintained antinociception >50% MPE for 80 min. The area under the curve (AUC) for the 3.2 and 5.6 mg/kg doses are plotted in Panel B along with those of the other analogs. Two peptides (dark bars) produced potent antinociception similar to the Analog 4, i.e., a peptide with substitution of a basic AA (Arg) in position 6, and a peptide with substitution of 2,6-dimethyl-L-tyrosine (DMT) in place of Tyr in position one ($DMT^1$-Gly). Significant reduction of potency was observed by substitution of Tyr, Met, and Pro in position 6 (white bars), relative to Analog 4, although the compounds were still active, while Leu, Gln, and Ser showed intermediate potency (grey bars). Some preference for smaller moieties within a class is indicated by the greater potency of Ser vs Tyr for hydroxyl AAs, and for Gly vs Leu for aliphatic AAs. Positive charge appears preferable to negative charge as reflected in the greater potency of Arg vs Gln. Panel C: In addition to $Trp^3$ hexapeptides, a $Phe^3$ $Gly^6$ hexapeptide was compared to the reference $Trp^3$-$Gly^6$ peptide (SEQ ID NO: 3). For this comparison, HCl salt forms of the peptides were tested while those in A and B were acetate salts. The analogs with an HCl (C) salt form provided a greater area under the curve relative to acetate salt (A,B), and the $Phe^3$ analog was fully effective (C); *, ***=p<0.05, 0.001 main effect of drug relative to $Gly^6$ analog, n=5. The results indicate that both Tyr and DMT are effective in position 1, preferential amino acids in position 6 are Gly and Arg, and that to a lesser extent, several additional amino acids in position 6 can induce antinociception.

As a result of the success of Analog 4 in the multiple tests described here, several additional hexapeptides of Formula I and a variant with 2,6-dimethyltyrosine (DMT) in place of the Tyr residue at position 1 were synthesized and tested for antinociception in the tail flick test following subcutaneous injection to mice. FIG. 18 illustrates that both Tyr and DMT were effective in position 1, preferential amino acids in position 6 were Gly (Analog 4) and Arg. Several additional amino acids in position 6 induced antinociception to a lesser extent compared to Gly and Arg.

Discussion

The EM analogs tested here provide potent antinociception (FIG. 12, Panels C-E, FIG. 13, Panel D, FIG. 14, Panel A, and FIG. 15, Panel A) with reduction or absence of six major side effects of currently used opioids: abuse liability, respiratory depression, impairment of motor coordination, tolerance, hyperalgesia, and glial activation. While all analogs proved superior to morphine against the side effects tested, some differences indicate that they may provide new tools for understanding analgesia vs. side-effects and their separation for clinical application. First, Analog 2 (SEQ ID NO: 2) (an EM2 analog) showed low motor impairment relative to that produced by morphine and two analogs of EM1, i.e., Analog 1 (SEQ ID NO: 1) and Analog 3 (SEQ ID NO: 5). The latter analogs, however, showed preferable profiles in respiratory and abuse liability tests. Analog 4 (SEQ ID NO: 3), based on the EM1 structure, showed that remarkably low motor impairment, as well as favorable respiratory and abuse liability profiles, could be achieved in a single molecule. Analog 4 proved unexpectedly superior in tests of respiratory depression, motor impairment (FIG. 13), and abuse liability (FIG. 14), while producing the most potent antinociceptive effects (FIG. 13, Panels C and D). All four analogs produced far less tolerance than morphine (FIG. 14, Panel A) and did not induce glial cell (FIG. 14, Panel B) or CGRP (FIG. 14, Panel D) activation. While morphine upregulated microglial P2X7 receptors, Analog 4 did not (FIG. 14, Panel F). Compared to currently available opioids, the prolonged antinociception and lack of adverse effects from the analogs shown here is unprecedented.

Analogs of Endomorphins.

The parent compounds of these analogs, the endomorphins (EMs) (23), showed early promise for a profile of potent analgesia with reduced side effects (29,22). The linear native peptides, however, are metabolically labile. While "constant renewal" methods such as viral vector-based delivery of these peptides have provided prolonged pain relief (47,59), structural modifications are required for more stable drug-like compounds. Numerous analogs of EMs have been developed with the goal of optimizing drug-like properties and avoiding side-effects (37,40,41,42,52). The approach described herein has focused on cyclization combined with D-amino acid substitution in a cyclic pentapeptide or hexapeptide side chain-to-side chain structure. This strategy permits amidation or extension of the C-terminus, and provides greater solubility and improved pharmacological profiles relative to linear peptide or side chain to C-terminus cyclic structures that were described previously. The resulting compounds of Formula I show high solubility, stability and favorable bioavailability as suggested by activity after peripheral (including oral) administration (FIG. 12) and penetration of the blood-brain barrier, as shown by central antagonism of antinociception produced by peripheral administration of the analogs (FIG. 13, Panel G). These advantageous drug characteristics are accompanied by the favorable spectrum of antinociception/side effect profiles described above.

Opioid-induced respiratory depression can be deadly, but the analogs described herein (especially Analogs 1 and 4) did not impair respiration even at equi- or greater-antinociceptive doses compared to morphine. Analog 4 showed no significant respiratory depression at doses producing significantly longer antinociception than morphine. Analogs 2 and 4 also did not produce impairment of motor coordination, while rats given morphine were significantly impaired at equi-antinociceptive doses. Older adults who take opioids for pain have an increased risk for falls and accidents. Opioids such as those shown here, that alleviate pain without producing motor deficits, would be particularly useful for this population.

The analogs described herein produced significantly less tolerance than morphine even though the antinociceptive effects were matched. Numerous mechanisms have been postulated for opioid tolerance. Some mechanisms of relevance to the current study include effects of agonist efficacy, mu agonist/delta antagonist properties, and glial activation. Stevens et al. (53) showed that sufentanyl produced less tolerance than morphine at comparably effective doses. They suggested that high efficacy agonists have a lower receptor reserve requirement for maintaining antinociception, and therefore show less tolerance. The analogs described herein are consistent with this hypothesis, since they are high efficacy agonists and show reduced tolerance. Combining a delta (DOR) antagonist with a MOR agonist reduces tolerance (1). This profile for Analogs 1, 3 and 4 (FIG. 11, Panel B) could contribute to the relative lack of tolerance. However, since the delta antagonist effect of the analogs is of high efficacy but low potency, further studies would be required to establish the relative potency ratio of the MOR agonism/DOR antagonism required to affect tolerance. In addition, Analog 2 showed reduced tolerance despite a lack of DOR antagonism, indicating the likely involvement of multiple mechanisms and the importance of in vivo tests for assessing this complex process.

A potentially important contributing mechanism to the reduced tolerance produced by the analogs described herein is differential glial activation. Many studies show that morphine activates glia through a variety of mechanisms, resulting in production of proinflammatory cytokines [IL-1, IL-6, IL-18, TNFα (27,39,49)] and PG, ATP, NO, and ROS (57), which are also "pronociceptive" and contribute to morphine tolerance and hyperalgesia (28,39,49,51,19,57,58). Phosphorylation of microglial p38 (pp38), which induces many of these pronociceptive molecules (38), plays a key role in tolerance paradigms (28,34,38,56).

While morphine-induced glial activation is well-established, the mechanism is the subject of considerable debate. Three leading hypotheses are (1) activation of a non-opioid site on microglial TLR4/MD-2 receptors (38,58), (2) direct action at MOR on microglia that stimulates purinergic (P2X) receptor signaling (31,35,62), and (3) the release of proinflammatory CGRP that activates glial-neuron inflammatory crosstalk (56). All three of these proposed mechanisms ultimately converge onto the p38 pathway to induce the release of pronociceptive molecules, so a crucial finding here is that chronic exposure to the analogs did not change pp38 levels while morphine significantly upregulated pp38. In addition, EM Analog 4 unexpectedly did not change CGRP levels or P2X7 receptor (P2X7R) expression, in contrast to morphine which robustly increased the "activated" microglia phenotype that strongly co-labeled with P2X7Rs. This is consistent with studies showing direct CGRP (56) and P2X7R (27,62) involvement in the development of tolerance to morphine. Hence, the reduced tolerance and hyperalgesia after EM analogs may be partly due to less glial reactivity. The present study is the first to our knowledge in which MOR-selective agonists did not induce glial, pp38, CGRP or P2X7R activation, while morphine, at the same antinociceptive effectiveness, produced significant activation.

Morphine-induced glial reactivity raises a host of issues concerning exacerbation of conditions associated with inflammation, including post-operative-induced (34), nerve injury-induced (34,43,49) and inflammation-induced (43) pain, traumatic brain injury (45), neurodegenerative diseases (32), and advancing age (25). Pain therapy in these conditions would be best served by opioids shown here that do not exacerbate inflammatory responses. The discovery of opioid induced proinflammatory responses has led to efforts to develop anti-inflammatory medications as adjuncts to opioid treatment to enhance analgesia and reduce tolerance. The compounds of Formula I provide a clearly preferable approach, in that immune modulators would not be required.

In addition to tolerance, differential glial activation may contribute to the differences between the analogs and morphine in other side effects. The microglial cell inhibitor minocycline blocked the respiratory depressive effects of morphine at similar doses and time frame used here (36), but see (63). Several studies have linked glial reactivity to morphine-induced reward behaviors. Morphine-induced CPP was associated with increased expression of Iba1 and pp38 in the nucleus accumbens (NAc) (61). Systemic (36) and intra-accumbens (61) minocycline blocked morphine-induced CPP, and intra-NAc injection of media from cultured astrocytes potentiated CPP for morphine (46).

Although numerous EM analogs have been developed, abuse liability effects have not been reported previously. Because of the importance of this side-effect, the analog compounds described herein were tested in both conditioned place preference (CPP) and self-administration (SA) paradigms. Tested at a range of physiologically relevant doses, Analog 4 did not produce CPP or aversive behaviors. Morphine promoted reward effects under long-term access SA conditions, the most sensitive SA paradigm (55), while the analogs did not. A recent review of rat self-administration studies showed that they were concordant with at least one of two human clinical indicators of abuse liability in 64 of 71 (90.1%) drug cases (48). Based on this correlation, the likelihood of abuse in humans is low for the analogs. Circumventing abuse liability is a major advance, since most available opioids produce rewarding effects in CPP and/or SA models (48,54).

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

The following references are referred to in this application and are incorporated herein by reference in their entirety:

(1) Abdelhamid E. E., Sultana M., Portoghese P. S. and Takemori A. E. (1991) Selective blockage of delta opioid receptors prevents the development of morphine tolerance and dependence in mice. J. Pharmacol. Exp. Ther. 258, 299-303.

(2) Bodanszky M. (1993) Peptide Chemistry: A Practical Textbook. Springer-Verlag, New York.

(3) Chen Y., Mestek A., Liu J., Hurley J. A. and Yu L. (1993) Molecular cloning and functional expression of a m-opioid receptor from rat brain. Mol. Pharmacol. 44, 8-12.

(4) Czapla M. A., Gozal D., Alea O. A., Beckerman R. C. and Zadina J. E. (2000) Differential cardiorespiratory effects of endomorphin 1, endomorphin 2, DAMGO, and morphine. Am. J. Respir. Crit Care Med 162, 994-999.

(5) Czapla M. A. and Zadina J. E. (2005) Reduced suppression of CO2-induced ventilatory stimulation by endomorphins relative to morphine. Brain Res. 1059, 159-166.

(6) Evans C. J., Keith D. E., Jr., Morrison H., Magendzo K. and Edwards R. H. (1992) Cloning of a delta opioid receptor by functional expression. Science 258, 1952-1955.

(7) Gianni W., Ceci M., Bustacchini S., Corsonello A., Abbatecola A. M., Brancati A. M., Assisi A., Scuteri A., Cipriani L. and Lattanzio F. (2009) Opioids for the treatment of chronic non-cancer pain in older people. Drugs Aging 26 Suppl 1, 63-73.

(8) Kieffer B. L. (1999) Opioids: first lessons from knockout mice. Trends Pharmacol. Sci 20, 19-26.

(9) Kieffer B. L., Befort K., Gaveriaux-Ruff C. and Hirth C. G. (1992) The d-opioid receptor: isolation of a cDNA by expression cloning and pharmacological characterization. Proc. Natl. Acad. Sci USA 89, 12048-12052.

(10) Kuehn B. M. (2009) New pain guideline for older patients: avoid NSAIDs, consider opioids. JAMA 302, 19.

(11) Lenard N. R., Daniels D. J., Portoghese P. S. and Roerig S. C. (2007) Absence of conditioned place preference or reinstatement with bivalent ligands containing mu-opioid receptor agonist and delta-opioid receptor antagonist pharmacophores. Eur. J. Pharmacol. 566, 75-82.

(12) Meng F., Xie G. X., Thompson R. C., Mansour A., Goldstein A., Watson S. J. and Akil H. (1993) Cloning and pharmacological characterization of a rat k opioid receptor. Proc. Natl. Acad. Sci USA 90, 9954-9958.

(13) Minami M., Toya T., Katao Y., Maekawa K., Nakamura S., Onogi T., Kaneko S. and Satoh M. (1993) Cloning and expression of a cDNA for the rat k-opioid receptor. FEBS Lett. 329, 291-295.

(14) Nishi M., Takeshima H., Fukuda K., Kato S. and Mori K. (1993) cDNA cloning and pharmacological characterization of an opioid receptor with high affinities for k-subtype-selective ligands. FEBS Lett. 330, 77-80.

(15) Prokai-Tatrai K., Prokai L. and Bodor N. (1996) Brain-targeted delivery of a leucine-enkephalin analogue by retrometabolic design. J. Med Chem. 39, 4775-4782.

(16) Raehal, K M, J K L Walker, and L M Bohn (2005) Morphine Side Effects in (3-Arrestin 2 Knockout Mice. J. Pharmacol. Exp. Ther. 314, 1195-1201.

(17) Rozenfeld R. and Devi L. A. (2010) Receptor heteromerization and drug discovery. Trends Pharmacol. Sci 31, 124-130.

(18) Stewart J. M. and Young J. D. (1984) Solid Phase Peptide Synthesis. Pierce Chemical Company.

(19) Tawfik V. L., LaCroix-Fralish M. L., Nutile-McMenemy N., DeLeo J. A. (2005) Transcriptional and translational regulation of glial activation by morphine in a rodent model of neuropathic pain. J. Pharmacol. Exp. Ther. 313, 1239-1247.

(20) Thompson R. C., Mansour A., Akil H. and Watson S. J. (1993) Cloning and pharmacological characterization of a rat m opioid receptor. Neuron 11, 903-913.

(21) Wang J. B., Johnson P. S., Persico A. M., Hawkins A. L., Griffin C. A. and Uhl G. R. (1994) Human m opiate receptor. cDNA and genomic clones, pharmacologic characterization and chromosomal assignment. FEBS Lett. 338, 217-222.

(22) Wilson A. M., Soignier R. D., Zadina J. E., Kastin A. J., Nores W. L., Olson R. D. and Olson G. A. (2000) Dissociation of analgesic and rewarding effects of endomorphin-1 in rats. Peptides 21, 1871-1874.

(23) Zadina J. E., Hackler L., Ge L. J. and Kastin A. J. (1997) A potent and selective endogenous agonist for the m-opiate receptor. Nature 386, 499-502.

(24) Al-Khrasani, M., Lacko, E., Riba, P., Kiraly, K., Sobor, M., Timar, J., Mousa, S., Schafer, M., Furst, S., 2012. The central versus peripheral antinociceptive effects of mu-opioid receptor agonists in the new model of rat visceral pain. Brain Research Bulletin 87, 238-243.

(25) Barrientos, R. M., Frank, M. G., Watkins, L. R., Maier, S. F., 2010. Memory impairments in healthy aging: Role of aging-induced microglial sensitization. Aging and Disease 1, 212-231.

(26) Catheline, G., Kayser, V., Idanpaan-Heikkila, J. J., Guilbaud, G., 1996. The antinociceptive activity of k- but not d-opioid receptor agonists is maintained in morphine-tolerant neuropathic rats. European Journal of Pharmacology 318, 273-281.

(27) Chen, M. L., Cao, H., Chu, Y. X., Cheng, L. Z., Liang, L. L., Zhang, Y. Q., Zhao, Z. Q., 2012. Role of P2X7 receptor-mediated IL-18/IL-18R signaling in morphine tolerance: multiple glial-neuronal dialogues in the rat spinal cord. Journal of Pain 13, 945-958.

(28) Cui, Y., Chen, Y., Zhi, J. L., Guo, R. X., Feng, J. Q., Chen, P. X., 2006. Activation of p38 mitogen-activated protein kinase in spinal microglia mediates morphine antinociceptive tolerance. Brain Research 1069, 235-243.

(29) Czapla, M. A., Gozal, D., Alea, O. A., Beckerman, R. C., Zadina, J. E., 2000. Differential cardiorespiratory effects of endomorphin 1, endomorphin 2, DAMGO, and morphine. American Journal of Respiratory and Critical Care Medicine 162, 994-999.

(30) Desmeules, J. A., Kayser, V., Gacel, G., Guilbaud, G., Rogues, B. P., 1993. The highly selective d agonist BUBU induces an analgesic effect in normal and arthritic rat and this action is not affected by repeated administration of low doses of morphine. Brain Research 611, 243-248.

(31) Ferrini, F., Trang, T., Mattioli, T. A., Laffray, S., Del'Guidice, T., Lorenzo, L. E., Castonguay, A., Doyon, N., Zhang, W., Godin, A. G., Mohr, D., Beggs, S., Vandal, K., Beaulieu, J. M., Cahill, C. M., Salter, M. W., De Koninck, Y., 2013. Morphine hyperalgesia gated through microglia-mediated disruption of neuronal Cl-homeostasis. Nature Neuroscience 16, 183-192.

(32) Frank-Cannon, T. C., Alto, L. T., McAlpine, F. E., Tansey, M. G., 2009. Does neuroinflammation fan the flame in neurodegenerative diseases? Molecular Neurodegeneration 4, 47.

(33) He, L., Kim, J., Ou, C., McFadden, W., van Rijn, R. M., Whistler, J. L., 2009. Methadone antinociception is dependent on peripheral opioid receptors. Journal of Pain 10, 369-379.

(34) Horvath, R. J., Landry, R. P., Romero-Sandoval, E. A., DeLeo, J. A., 2010a. Morphine tolerance attenuates the resolution of postoperative pain and enhances spinal microglial p38 and extracellular receptor kinase phosphorylation. Neuroscience 169, 843-854.

(35) Horvath, R. J., Romero-Sandoval, E. A., De Leo, J. A., 2010b. Inhibition of microglial P2X4 receptors attenuates morphine tolerance, Iba1, GFAP and m opioid receptor protein expression while enhancing perivascular microglial ED2. Pain 150, 401-413.

(36) Hutchinson, M. R., Northcutt, A. L., Chao, L. W., Kearney, J. J., Zhang, Y., Berkelhammer, D. L., Loram, L. C., Rozeske, R. R., Bland, S. T., Maier, S. F., Gleeson, T. T., Watkins, L. R., 2008. Minocycline suppresses morphine-induced respiratory depression, suppresses morphine-induced reward, and enhances systemic morphine-induced analgesia. Brain, Behavior, and Immunity 22, 1248-1256.

(37) Janecka, A., Gentilucci, L., 2014. Cyclic endomorphin analogs in targeting opioid receptors to achieve pain relief. Future Medicinal Chemistry 6, 2093-2101.

(38) Ji, R. R., 2010. Targeting microglial purinergic signaling to improve morphine analgesia. Pain 150, 377-378.

(39) Johnston, I. N., Milligan, E. D., Wieseler-Frank, J., Frank, M. G., Zapata, V., Campisi, J., Langer, S., Martin, D., Green, P., Fleshner, M., Leinwand, L., Maier, S. F., Watkins, L. R., 2004. A role for proinflammatory cytokines and fractalkine in analgesia, tolerance, and subsequent pain facilitation induced by chronic intrathecal morphine. Journal of Neuroscience 24, 7353-7365.

(40) Keresztes, A., Borics, A., Toth, G., 2010. Recent advances in endomorphin engineering. Chem Med Chem 5, 1176-1196.

(41) Lazarus, L. H., Okada, Y., 2012. Engineering endomorphin drugs: state of the art. Expert Opinion on Therapeutic Patents 22, 1-14.

(42) Liu, W. X., Wang, R., 2012. Endomorphins: potential roles and therapeutic indications in the development of opioid peptide analgesic drugs. Medicinal Research Reviews 32, 536-580.

(43) Loram, L. C., Grace, P. M., Strand, K. A., Taylor, F. R., Ellis, A., Berkelhammer, D., Bowlin, M., Skarda, B., Maier, S. F., Watkins, L. R., 2012. Prior exposure to repeated morphine potentiates mechanical allodynia induced by peripheral inflammation and neuropathy. Brain, Behavior, and Immunity 26, 1256-1264.

(44) Morgan, M. M., Fossum, E. N., Stalding, B. M., King, M. M., 2006. Morphine antinociceptive potency on chemical, mechanical, and thermal nociceptive tests in the rat. Journal of Pain 7, 358-366.

(45) Morganti-Kossmann, M. C., Satgunaseelan, L., Bye, N., Kossmann, T., 2007. Modulation of immune response by head injury. Injury 38, 1392-1400.

(46) Narita, M., Suzuki, M., Kuzumaki, N., Miyatake, M., Suzuki, T., 2008. Implication of activated astrocytes in the development of drug dependence: differences between methamphetamine and morphine. Annals of the New York Academy of Sciences 1141, 96-104.

(47) Nasirinezhad, F., Gajavelli, S., Priddy, B., Jergova, S., Zadina, J., Sagen, J., 2015. Viral vectors encoding endomorphins and serine histogranin attenuate neuropathic pain symptoms after spinal cord injury in rats. Molecular Pain 11, 2.

(48) O'Connor, E. C., Chapman, K., Butler, P., Mead, A. N., 2011. The predictive validity of the rat self-administration model for abuse liability. Neuroscience and Biobehavioral Reviews 35, 912-938.
(49) Raghavendra, V., Rutkowski, M. D., DeLeo, J. A., 2002. The role of spinal neuroimmune activation in morphine tolerance/hyperalgesia in neuropathic and sham-operated rats. Journal of Neuroscience 22, 9980-9989.
(50) Smith, R. R., Martin-Schild, S., Kastin, A. J., Zadina, J. E., 2001. Decreases in endomorphin-2-like immunoreactivity concomitant with chronic pain after nerve injury. Neuroscience 105, 773-778.
(51) Song, P., Zhao, Z. Q., 2001. The involvement of glial cells in the development of morphine tolerance. Neuroscience Research 39, 281-286.
(52) Spetea, M., Asim, M. F., Wolber, G., Schmidhammer, H., 2013. The m opioid receptor and ligands acting at the m opioid receptor, as therapeutics and potential therapeutics. Current Pharmaceutical Design 19, 7415-7434.
(53) Stevens, C. W., Yaksh, T. L., 1989. Potency of infused spinal antinociceptive agents is inversely related to magnitude of tolerance after continuous infusion. Journal of Pharmacology and Experimental Therapeutics 250, 1-8.
(54) Tzschentke, T. M., 2007. Measuring reward with the conditioned place preference (CPP) paradigm: update of the last decade. Addiction Biology 12, 227-462.
(55) Wade, C. L., Vendruscolo, L. F., Schlosburg, J. E., Hernandez, D. O., Koob, G. F., 2015. Compulsive-like responding for opioid analgesics in rats with extended access. Neuropsychopharmacology 40, 421-428.
(56) Wang, Z., Ma, W., Chabot, J. G., Quirion, R., 2010. Calcitonin gene-related peptide as a regulator of neuronal CaMKII-CREB, microglial p38-NFkB and astroglial ERK-Stat1/3 cascades mediating the development of tolerance to morphine-induced analgesia. Pain 151, 194-205.
(57) Watkins, L. R., Hutchinson, M. R., Johnston, I. N., Maier, S. F., 2005. Glia: novel counter-regulators of opioid analgesia. Trends in Neurosciences 28, 661-669.
(58) Watkins, L. R., Hutchinson, M. R., Rice, K. C., Maier, S. F., 2009. The "toll" of opioid-induced glial activation: improving the clinical efficacy of opioids by targeting glia. Trends in Pharmacological Sciences 30, 581-591.
(59) Wolfe, D., Hao, S., Hu, J., Srinivasan, R., Goss, J., Mata, M., Fink, D. J., Glorioso, J. C., 2007. Engineering an endomorphin-2 gene for use in neuropathic pain therapy. Pain 133, 29-38.
(60) Yaksh, T. L., Rudy, T. A., 1976. Chronic catheterization of the spinal subarachnoid space. Physiology and Behavior 17, 1031-1036.
(61) Zhang, X. Q., Cui, Y., Cui, Y., Chen, Y., Na, X. D., Chen, F. Y., Wei, X. H., Li, Y. Y., Liu, X. G., Xin, W. J., 2012. Activation of p38 signaling in the microglia in the nucleus accumbens contributes to the acquisition and maintenance of morphine-induced conditioned place preference. Brain, Behavior, and Immunity 26, 318-325.
(62) Zhou, D., Chen, M. L., Zhang, Y. Q., Zhao, Z. Q., 2010. Involvement of spinal microglial P2X7 receptor in generation of tolerance to morphine analgesia in rats. Journal of Neuroscience 30, 8042-8047.
(63) Zwicker, J. D., Zhang, Y., Ren, J., Hutchinson, M. R., Rice, K. C., Watkins, L. R., Greer, J. J., Funk, G. D., 2014. Glial TLR4 signaling does not contribute to opioid-induced depression of respiration. Journal of Applied Physiology 117, 857-868.

What is claimed is:

1. A cyclic peptide of Formula I:

$$\text{H-Tyr-cyclo}[X_1\text{-}X_2\text{-}X_3\text{-}X_4]\text{-}X_5 \quad (I),$$ and salts thereof, wherein $X_1$ is a basic D-amino acid;
$X_2$ is Trp;
$X_3$ is an aromatic amino acid;
$X_4$ is an acidic amino acid;
$X_5$ is selected from the group consisting of Ala-NHR, Arg-NHR, Asn-NHR, Asp-NHR, Cys-NHR, Glu-NHR, Gln-NHR, Gly-NHR, His-NHR, Ile-NHR, Leu-NHR, Met-NHR, Orn-NHR, Phe-NHR, Pro-NHR, Ser-NHR, Thr-NHR, Trp-NHR, Tyr-NHR, and Val-NHR, wherein R is H or an alkyl group; and there is an amide bond between an amino group and a carboxylic acid group on side chains of amino acids $X_1$ and $X_4$.

2. The cyclic peptide of claim 1, wherein $X_1$ is selected from the group consisting of D-Lys and D-Orn.

3. The cyclic peptide of claim 1, wherein $X_4$ is selected from the group consisting of D-Asp, D-Glu, Asp, and Glu.

4. The cyclic peptide of claim 1, wherein $X_1$ is selected from the group consisting of D-Lys and D-Orn; and $X_4$ is selected from the group consisting of D-Asp, D-Glu, Asp, and Glu.

5. The cyclic peptide of claim 1, wherein $X_3$ is selected from the group consisting of Phe, D-Phe, and p-Y-Phe, wherein Y is $NO_2$, F, Cl, or Br.

6. The cyclic peptide of claim 1, wherein $X_3$ is Phe.

7. The cyclic peptide of claim 1, wherein $X_3$ is p-Cl-Phe.

8. The cyclic peptide of claim 1, wherein R is H.

9. The cyclic peptide of claim 1, wherein R is H and $X_5$ is Gly-$NH_2$.

10. The cyclic peptide of claim 1, wherein the alkyl group is a methyl, ethyl, propyl, isopropyl, butyl, isobutyl, pentyl, isopentyl, hexyl, isohexyl, heptyl, or isoheptyl group.

11. The cyclic peptide of claim 1, wherein the peptide is Tyr-cyclo[D-Lys-Trp-Phe-Glu]-Gly-$NH_2$ (SEQ ID NO: 3).

12. The cyclic peptide of claim 1, wherein $X_5$ is Arg-$NH_2$.

13. The cyclic peptide of claim 1, wherein $X_1$ is D-Lys.

14. The cyclic peptide of claim 1, wherein $X_1$ is D-Orn.

15. The cyclic peptide of claim 1, wherein $X_4$ is Glu.

16. The cyclic peptide of claim 1, wherein $X_4$ is Asp.

17. A pharmaceutical composition comprising a pharmaceutically acceptable carrier and the cyclic peptide of claim 1.

18. The pharmaceutical composition of claim 17, wherein the cyclic peptide is in the form of an acetate salt.

19. The pharmaceutical composition of claim 18, wherein the cyclic peptide is Tyr-cyclo[D-Lys-Trp-Phe-Glu]-Gly-$NH_2$ (SEQ ID NO: 3).

20. A method of treating pain comprising administering to a subject in need thereof an analgesic amount of the cyclic peptide of claim 1.

21. The method of claim 20, wherein the cyclic peptide is Tyr-cyclo[D-Lys-Trp-Phe-Glu]-Gly-$NH_2$ (SEQ ID NO: 3).

22. A method of treating pain comprising intravenously administering to a subject in need thereof an analgesic amount of the pharmaceutical composition of claims 18.

* * * * *

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: Cyclic endomorphin analog; residues 2-5 form a
      cyclic structure
<221> NAME/KEY: VARIANT
<222> LOCATION: 2
<223> OTHER INFORMATION: Xaa = D-Lys

<400> SEQUENCE: 1

Tyr Xaa Trp Phe Glu
1               5

<210> SEQ ID NO 2
<211> LENGTH: 5
<212> TYPE: PRT
<213> ORGANISM: Artificial Sequence
<220> FEATURE:
<223> OTHER INFORMATION: Cyclic endomorphin analog; residues 2-5 form a
      cyclic structure
<221> NAME/KEY: VARIANT
<222> LOCATION: 2
<223> OTHER INFORMATION: Xaa = D-Glu

<400> SEQUENCE: 2

Tyr Xaa Phe Phe Lys
1               5
```

```
<210> SEQ ID NO 3
<211> LENGTH: 6
<212> TYPE: PRT
<213> ORGANISM: Artificial Sequence
<220> FEATURE:
<223> OTHER INFORMATION: Cyclic endomorphin analog; residues 2-5 form a
      cyclic structure
<221> NAME/KEY: VARIANT
<222> LOCATION: 2
<223> OTHER INFORMATION: Xaa = D-Lys

<400> SEQUENCE: 3

Tyr Xaa Trp Phe Glu Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Cyclic endomorphin analog; residues 2-5 form a
      cyclic structure
<221> NAME/KEY: VARIANT
<222> LOCATION: 2
<223> OTHER INFORMATION: Xaa = D-Glu

<400> SEQUENCE: 4

Tyr Xaa Phe Phe Lys Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Cyclic endomorphin analog; residues 2-5 form a
      cyclic structure
<221> NAME/KEY: VARIANT
<222> LOCATION: 2
<223> OTHER INFORMATION: Xaa = D-Lys

<400> SEQUENCE: 5

Tyr Xaa Trp Phe Asp
1               5

<210> SEQ ID NO 6
<211> LENGTH: 5
<212> TYPE: PRT
<213> ORGANISM: Artificial Sequence
<220> FEATURE:
<223> OTHER INFORMATION: Cyclic endomorphin analog; residues 2-5 form a
      cyclic structure
<221> NAME/KEY: VARIANT
<222> LOCATION: 2
<223> OTHER INFORMATION: Xaa = D-Glu
<221> NAME/KEY: VARIANT
<222> LOCATION: 4
<223> OTHER INFORMATION: Xaa = N-methyl-Phe

<400> SEQUENCE: 6

Tyr Xaa Phe Xaa Lys
1               5

<210> SEQ ID NO 7
<211> LENGTH: 6
<212> TYPE: PRT
<213> ORGANISM: Artificial Sequence
<220> FEATURE:
<223> OTHER INFORMATION: Cyclic endomorphin analog; residues 2-5 form a
      cyclic structure
<221> NAME/KEY: VARIANT
```

```
<222> LOCATION: 2
<223> OTHER INFORMATION: Xaa = D-Orn
<221> NAME/KEY: VARIANT
<222> LOCATION: 4
<223> OTHER INFORMATION: Xaa = p-Cl-Phe

<400> SEQUENCE: 7

Tyr Xaa Phe Xaa Asp Val
1               5

<210> SEQ ID NO 8
<211> LENGTH: 4
<212> TYPE: PRT
<213> ORGANISM: Homo sapiens

<400> SEQUENCE: 8

Tyr Pro Trp Phe
1

<210> SEQ ID NO 9
<211> LENGTH: 4
<212> TYPE: PRT
<213> ORGANISM: Homo sapiens

<400> SEQUENCE: 9

Tyr Pro Phe Phe
1

<210> SEQ ID NO 10
<211> LENGTH: 4
<212> TYPE: PRT
<213> ORGANISM: Artificial Sequence
<220> FEATURE:
<223> OTHER INFORMATION: Cyclic tetrapeptide; residues 2-4 form a cyclic
      structure
<221> NAME/KEY: VARIANT
<222> LOCATION: 2
<223> OTHER INFORMATION: Xaa = D-Lys

<400> SEQUENCE: 10

Tyr Xaa Trp Phe
1

<210> SEQ ID NO 11
<211> LENGTH: 4
<212> TYPE: PRT
<213> ORGANISM: Artificial Sequence
<220> FEATURE:
<223> OTHER INFORMATION: Cyclic tetrapeptide; residues 2-4 form a cyclic
      structure
<221> NAME/KEY: VARIANT
<222> LOCATION: 2
<223> OTHER INFORMATION: Xaa = D-Lys

<400> SEQUENCE: 11

Tyr Xaa Phe Phe
1
```